(12) United States Patent
Nagano et al.

(10) Patent No.: US 9,714,260 B2
(45) Date of Patent: Jul. 25, 2017

(54) ASYMMETRICAL SI RHODAMINE AND RHODOL SYNTHESIS

(71) Applicant: THE UNIVERSITY OF TOKYO, Tokyo (JP)

(72) Inventors: Tetsuo Nagano, Tokyo (JP); Kenjiro Hanaoka, Tokyo (JP); Takahiro Egawa, Tokyo (JP); Yu Kushida, Tokyo (JP); Koji Numasawa, Tokyo (JP); Takuya Myochin, Tokyo (JP); Wen Piao, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/759,306

(22) PCT Filed: Jan. 7, 2014

(86) PCT No.: PCT/JP2014/050088
§ 371 (c)(1),
(2) Date: Jul. 6, 2015

(87) PCT Pub. No.: WO2014/106957
PCT Pub. Date: Jul. 10, 2014

(65) Prior Publication Data
US 2015/0353585 A1  Dec. 10, 2015

(30) Foreign Application Priority Data

Jan. 7, 2013 (JP) ................ 2013-000663
Mar. 4, 2013 (JP) ................ 2013-042330

(51) Int. Cl.
| | |
|---|---|
| C07F 7/08 | (2006.01) |
| C07C 209/68 | (2006.01) |
| C07C 213/08 | (2006.01) |
| C09B 11/24 | (2006.01) |
| C09B 11/28 | (2006.01) |
| C09B 69/00 | (2006.01) |

(52) U.S. Cl.
CPC .......... *C07F 7/0816* (2013.01); *C07C 209/68* (2013.01); *C07C 213/08* (2013.01); *C09B 11/24* (2013.01); *C09B 11/28* (2013.01); *C09B 69/008* (2013.01)

(58) Field of Classification Search
CPC ....................................................... C07F 7/08
USPC ....................................................... 556/406
See application file for complete search history.

(56) References Cited

U.S. PATENT DOCUMENTS

| 9,329,184 | B2 * | 5/2016 | Nagano | G01N 33/582 |
| 2013/0196362 | A1 | 8/2013 | Yang et al. | |
| 2016/0102336 | A1 * | 4/2016 | Nagano | C12Q 1/37 |
| | | | | 435/23 |

FOREIGN PATENT DOCUMENTS

| CN | 1810812 A | 8/2006 | |
| WO | 99/01447 A | 1/1999 | |
| WO | 2007/100061 A1 | 9/2007 | |
| WO | 2010/126077 A1 | 11/2010 | |
| WO | 2012/083064 A1 | 6/2012 | |
| WO | WO 2012083064 A1 * | 6/2012 | ......... G01N 21/6428 |
| WO | 2012/111818 A1 | 8/2012 | |
| WO | 2013/029650 A1 | 3/2013 | |
| WO | 2013/113279 A | 8/2013 | |

OTHER PUBLICATIONS

Koide et al., ACS Chemical Biology, 2011, 6(6), 600-608.*
Koide et al., J. Am. Chem. Soc. 2012, 134, 5029-5031.*
Extended European Search Report issued with respect to Application No. 14735268.6, dated Aug. 8, 2016.
Grazvyas Lukinavicius et al., "A near-infrared fluorophore for live-cell super-resolution microscopy of cellular proteins", Nature Chemistry, vol. 5, 2013, pp. 132-139.
Takuya Myochin et al., "Design Strategy for a Near-Infrared Fluorescence Probe for Matrix Metalloproteinase Utilizing Highly Cell Permeable Boron Dipyrromethene", Journal of the American Chemical Society, 2012, 134, pp. 13730-13737.
Yu Kushida et al., "Red fluorescent scaffold for highly sensitive protease activity probes", Bioorganic & Medicinal chemistry Letters 22, 2012, pp. 3908-3911.
Yuichiro Koide et al., "Development of an Si-Rhodamine-Based Far-Red to Near-Infrared Fluorescence Probe Selective for Hypochlorous Acid and Its Applications for Biological Imaging", Journal of the American Chemical Society, 2011, 133, pp. 5680-5682.
"Best", Pacifichem 2010, Dec. 19, 2010, pp. 2335.
Koide et al., "Evolution of Group 14 Rhodamines as Platforms for Near-Infrared Fluorescence Probes Utilizing Photoinduced Electron Transfer", ACS Chemical Biology, 2011, pp. 600-608, 6 (6).

(Continued)

*Primary Examiner* — Sudhakar Katakam
*Assistant Examiner* — Kofi Adzamli
(74) *Attorney, Agent, or Firm* — Greenblum & Bernstein, P.L.C.

(57) ABSTRACT

[Problem] To provide: a compound resulting from substituting with a silicon atom the oxygen atom at position 10 of a xanthene ring site of a rhodamine of which amino groups at position 3 and position 6 have an asymmetrical structure; a method for producing the compound; and a fluorescent probe that uses the compound.
[Solution] The compound represented by general formula (I) or a salt thereof.

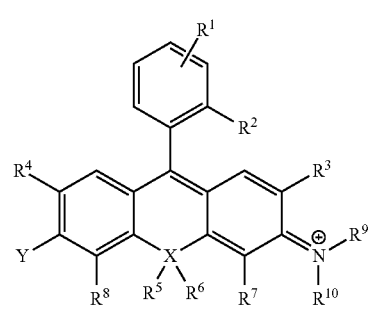

29 Claims, 15 Drawing Sheets

(56) References Cited

OTHER PUBLICATIONS

Koide et al., "Development of NIR Fluorescent Dyes Based on Si-rhodamine for in Vivo Imaging", Journal of American Chemical Society, 2012, pp. 5029-5031, 134 (11).
International Search Report issued with respect to application No. PCT/JP2014/050088, mail dated is Mar. 25, 2014.
Koide et al., "Evolution of Novel Rhodamines as a Platform for a Far-red to NR Emitting Fluorescence Probes", JSMI Report, 2009, p. 8-9.
International Preliminary Report on Patentability issued with respect to application No. PCT/JP2014/050088, mail dated is Jul. 7, 2015.

\* cited by examiner

ASYMMETRICAL SI RHODAMINE AND RHODOL SYNTHESIS

TECHNICAL FIELD

The present invention relates to a novel fluorescent probe, and more specifically relates to: a compound resulting from substituting with a silicon atom the oxygen atom at position 10 of a xanthene ring site of a rhodamine of which amino groups at position 3 and position 6 have an asymmetrical structure; a method for producing the compound; and a fluorescent probe that uses the compound. The present invention also relates to: a compound resulting from substituting with an amino group the hydroxy group of the xanthene ring in the compound resulting from substituting with a silicon atom the oxygen atom at position 10 of a xanthene ring of fluorescein; a method for producing the compound; and a fluorescent probe that uses the compound.

BACKGROUND ART

Rhodamine is a fluorescent dye, long known in the same fashion as fluorescein. Both have high fluorescence quantum yield in water and have therefore been widely applied in the field of biology as a fluorescent tag. Living-cell imaging that employs a fluorescent probe is frequently used in recent years, and rhodamine is also widely used as a mother nucleus of a fluorescent probe that plays a major role in living-cell imaging techniques.

Reported examples of fluorescent probes having a rhodamine skeleton include those used for detecting nitrogen monoxide (Patent Reference 1) and hypochlorous acid (Patent Reference 2). Also, already reported are a compound (TMDHS: 2,7-N,N,N',N'-tetramethyl-9-dimethyl-10-hydro-9-silaanthracene) resulting from substituting with a silicon atom the oxygen atom of pyronin, which is the basic skeleton of rhodamine, and application of the compound to a fluorescent probe (Non-patent References 1 and 2).

In fluorescent probes having TMDHS as a basic skeleton, intramolecular photo-induced electron transfer (PET) and the open or closed ring of a spiro ring are essentially used to turn fluorescence on or off. However, TMDHS or other compounds resulting from substituting with a silicon atom the oxygen atom of pyronin as reported in the past have the amino group at positions 2 and 7 substituted with a methyl group or other substituent group other than a hydrogen atom. There have yet to be any reports of a rhodamine analogue resulting from substituting with a silicon atom the oxygen atom of a compound in which the substituent group of amino groups at position 3 and position 6 has an asymmetrical structure in rhodamine, nor have there been any reports of a fluorescent probe that uses such a rhodamine analogue.

Several fluorescent probes for detecting active oxygen that are used in near-infrared fluorescent imaging have been developed, but these present problems in regard to the small increase in fluorescence after active oxygen has been detected and poor selectivity in relation to the active oxygen species.

PRIOR ART REFERENCES

Patent References

Patent Reference 1: International Publication WO 1999/001447
Patent Reference 2: International Publication WO 2007/100061

Non-Patent References

Non-Patent Reference 1: Best, Q., et al., Pacifichem 2010, Presentation No. 2335, 19 Dec. 2010

Non-Patent Reference 2: Koide Yuichiro, et al., 4th Meeting of the Japanese Society for Molecular Imaging, Presentation No. P8-9, 14 May 2009

SUMMARY OF THE INVENTION

Problems to be Solved by the Invention

An object of the present invention is to provide a novel fluorescent probe. More specifically, an object of the present invention is to provide: a compound resulting from substituting with a silicon atom the oxygen atom at position 10 of a xanthene ring site of a rhodamine of which amino groups at position 3 and position 6 have an asymmetrical structure; a method for producing the compound; and a fluorescent probe that uses the compound.

Still another object of the present invention is to provide: a compound resulting from substituting with an amino group the hydroxy group of the xanthene ring in the compound resulting from substituting with a silicon atom the oxygen atom at position 10 of a xanthenes ring of fluorescein; a method for producing the compound; and a fluorescent probe that uses the compound.

Yet another object of the present invention is to provide a near-infrared fluorescent probe for excellent active-oxygen detection with the aid of a compound resulting from substituting with a silicon atom the oxygen atom at position 10 of a xanthene ring site of a rhodamine of which amino groups at position 3 and position 6 have an asymmetrical structure.

Means Used to Solve the Above-Mentioned Problems

As a result of thoroughgoing studies to solve the above-described problems, the present inventors found that it is possible to manufacture an asymmetrical N,N-diallylamino-N',N'-dialkylamino-Si-xanthone compound by reacting, e.g., 3-bromo-N,N-diallylaniline as a starting material with a 3-bromobenzene amine compound, and, when the compound and a halobenzene derivative have been reacted and the allyl group thereafter desorbed, to manufacture a compound resulting from substituting with a silicon atom the oxygen atom at position 10 of a xanthene ring site of a rhodamine of which amino groups at position 3 and position 6 are asymmetrical (in the present specification, this compound may hereinafter be referred to as "asymmetrical Si rhodamine").

The present inventors also found that, with the manufacturing method described above, since the reactivity of 3-halo-N,N-diallyl aniline and the 3-halobenzene amine compound are different, it is difficult to obtain an asymmetrical product (4-(2-bromo-4-(dimethylamino)benzyl)-N,N-diallyl-3-bromobenzene amine) with high yield because a byproduct having a symmetrical substituent group is generated. In view of the above, after further thoroughgoing research, the present inventors found that it is possible to manufacture an asymmetrical Si rhodamine with high yield by converting 3-bromo-N,N-diallyl aniline to 3-bromo-N,N-diallyl-4-hydroxymethyl aniline, and then reacting this compound with a 3-bromobenzene amine compound to thereby proceed via 3-bromo-N,N-diallyl-4-(2-bromo-4-(dialkylamino)benzyl) aniline.

The present inventors also found that a compound (in the present specification, this compound may hereinafter be referred to as "rhodol") resulting from substituting with an amino group the hydroxy group of a xanthene ring can be efficiently synthesized starting from a compound (Tokyo- Magenta) resulting from substituting with a silicon atom the oxygen atom at position 10 of a xanthene ring site of fluorescein.

The present inventors also found that it is possible to provide a near-infrared fluorescent probe for excellent active-oxygen detection by bonding an aromatic ring to the nitrogen atom of a xanthene ring.

In other words, the present invention is;
[1] A compound expressed by general formula (I) below or a salt thereof.

[Chemical Formula 1]

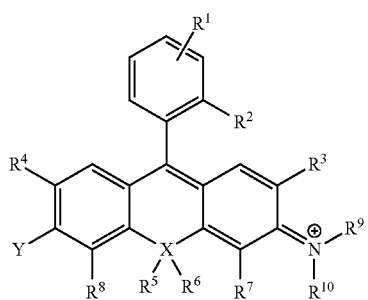

(I)

(where:
$R^1$ is a hydrogen atom or 1-4 of the same or different monovalent substituents present on a benzene ring;
$R^2$ is a monovalent substituent;
$R^3$ and $R^4$ are, each independently, a hydrogen atom, $C_{1-6}$ alkyl group, or halogen atom;
$R^5$ and $R^6$ are, each independently, a $C_{1-6}$ alkyl group or aryl group;
$R^7$ and $R^8$ are, each independently, a hydrogen atom, $C_{1-6}$ alkyl group, or halogen atom;
$R^9$ and $R^{10}$ are, each independently, a hydrogen atom, $C_{1-6}$ alkyl group, or monovalent substituent cleaved by contact with a measured substance;
$R^9$ or $R^{10}$ optionally forms, together with $R^3$ or $R^7$, a 5-7-member heterocyclyl or heteroaryl containing a nitrogen atom to which $R^9$ or $R^{10}$ binds, and optionally contains 1-3 additional heteroatoms selected from the group consisting of oxygen atoms, nitrogen atoms, and sulfur atoms as ring-constituting members; the heterocyclyl or heteroaryl optionally being substituted by a $C_{1-6}$ alkyl, $C_{2-6}$ alkenyl, $C_{2-6}$ alkynyl, $C_{6-10}$ aralkyl, or $C_{6-10}$ alkyl-substituted alkenyl group;
Y is selected from
(1) —$NR^{11}R^{12}$
(2) —$OR^{13}$ or
(3) —N=N—$R^{14}$
where:
$R^{11}$ is a hydrogen atom, $C_{1-6}$ alkyl group, or monovalent substituent cleaved by contact with a measured substance;
$R^{12}$ is a hydrogen atom, $C_{1-6}$ alkyl group, or acyl group;
$R^{11}$ and $R^{12}$ optionally form a 5-7-member heterocyclyl containing a nitrogen atom to which $R^{11}$ and $R^{12}$ bind, and optionally contain 1-3 additional heteroatoms selected from the group consisting of oxygen atoms, nitrogen atoms, and sulfur atoms as ring-constituting members; the heterocyclyl optionally being substituted by a $C_{1-6}$ alkyl group;
$R^{13}$ is a hydrogen atom or monovalent substituent cleaved by contact with a measured substance; and
$R^{14}$ is an aryl group; and
X is a silicon, germanium, or tin atom;
when Y is —$NR^{11}R^{12}$, (i) $R^9$ and $R^{10}$ not being monovalent substituents cleaved by contact with a measured substance, and (ii) when $R^{11}$ and $R^{12}$ are hydrogen atoms, $R^9$ and $R^{10}$ not both being hydrogen atoms;

when Y is —$OR^{13}$ and $R^{13}$ is a hydrogen atom, $R^9$ or $R^{10}$ optionally being a monovalent substituent cleaved by contact with a measured substance; and
when Y is —N=N—$R^{14}$, $R^9$ and $R^{10}$ not being a monovalent substituent cleaved by contact with a measured substance)

[2] The compound or salt thereof according to [1] represented by general formula (Ia) below, Y being —$NR^{11}R^{12}$.

[Chemical Formula 2]

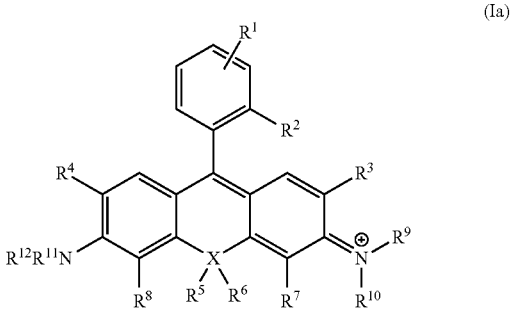

(Ia)

(where:
$R^1$ to $R^{12}$ and X are as defined in general formula (I), but (i) $R^9$ and $R^{10}$ are not monovalent substituents cleaved by contact with a measured substance, and (ii) when $R^{11}$ and $R^{12}$ are hydrogen atoms, $R^9$ and $R^{10}$ are not both hydrogen atoms)

[3] The compound or salt thereof according to [2], wherein $R^9$ or $R^{10}$ forms, together with $R^3$ or $R^7$, a 5-7-member heterocyclyl or heteroaryl containing a nitrogen atom to which $R^9$ or $R^{10}$ binds (the heterocyclyl or heteroaryl optionally contains 1-3 additional heteroatoms selected from the group consisting of oxygen atoms, nitrogen atoms, and sulfur atoms as ring-constituting members; the heterocyclyl or heteroaryl optionally being substituted by a $C_{1-6}$ alkyl, $C_{2-6}$ alkenyl, $C_{2-6}$ alkynyl, $C_{6-10}$ aralkyl group, or $C_{6-10}$ alkyl-substituted alkenyl group)

[4] The compound or salt thereof according to [3], wherein $R^9$ forms, together with $R^3$, a 5-7-member heterocyclyl or heteroaryl containing a nitrogen atom to which $R^9$ binds.

[5] The compound or salt thereof according to [4], represented by general formula (Ia-1) below.

[Chemical Formula 3]

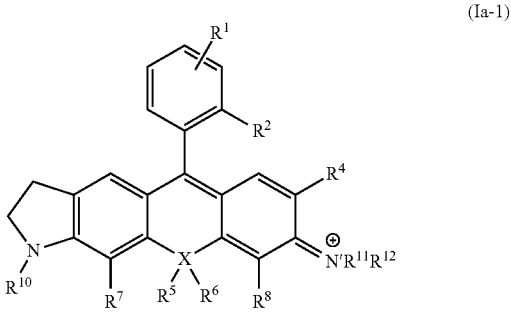

(Ia-1)

(where $R^1$-$R^2$, $R^4$-$R^8$, $R^{10}$-$R^{12}$, and X are as defined in general formula (Ia))

[6] The compound or salt thereof according to [2] to [5], wherein $R^{11}$ and $R^{12}$ forms a 5-7-member heterocyclyl containing a nitrogen atom to which $R^{11}$ and $R^{12}$ bind (the heterocyclyl optionally contains 1-3 additional heteroatoms selected from the group consisting of oxygen atoms, nitrogen atoms, and sulfur atoms as ring-constituting members; the heterocyclyl optionally being substituted by a $C_{1-6}$ alkyl group)

[7] The compound or salt thereof according to [6], wherein $R^{11}$ and $R^{12}$ form a piperazine ring together with a nitrogen atom to which $R^{11}$ and $R^{12}$ bind.

[8] The compound or salt thereof according to [7], represented by general formula (Ia-2) below.

[Chemical Formula 4]

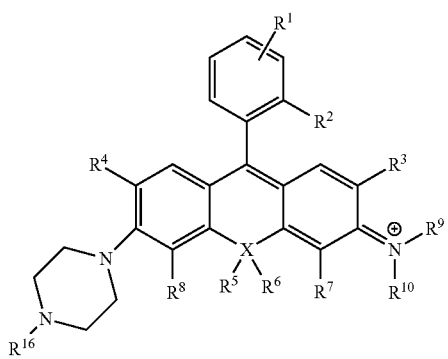

(Ia-2)

(where $R^1$-$R^{10}$ and X are as defined in general formula (Ia), and $R^{15}$ is a $C_{1-6}$ alkyl group)

[9] The compound or salt thereof according to any one of [1] to [5], wherein $R^{11}$ is a monovalent substituent cleaved by contact with an enzyme selected from the group consisting of peptidase, protease, lactamase, glycohydrolase, transferase, and oxidoreductase.

[10] The compound or salt thereof according to [9], wherein $R^{11}$ is a monovalent substituent cleaved by contact with an enzyme selected from the group consisting of peptidase, protease, and lactamase.

[11] The compound or salt thereof according to [9] or [10], wherein the peptidase or protease is an enzyme selected from the group consisting of caspase, prostate-specific antigen, leucine aminopeptidase, and γ-glutamyl transpeptidase.

[12] The compound or salt thereof according to [2], wherein the substituent constituting $R^{11}$ is an aromatic ring, and forms, together with $R^3$ and $R^9$, a 5-7-member heterocyclyl or heteroaryl containing a nitrogen atom to which $R^9$ binds, and $R^{12}$ is a $C_{1-6}$ alkyl group.

[13] The compound or salt thereof according to [12], represented by general formula (Ia-3) below.

[Compound 5]

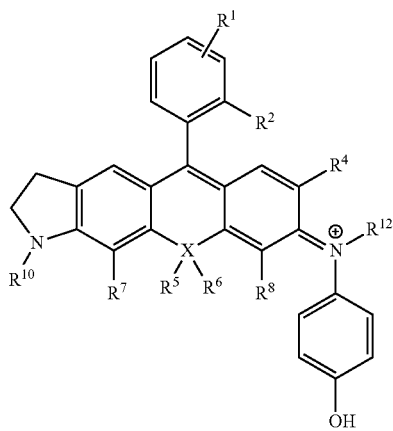

(Ia-3)

(where $R^1$-$R^2$, $R^4$-$R^8$, $R^{10}$, $R^{12}$ and X are as defined in general formula (Ia))

[14] The compound or salt thereof according to [13], represented by formula (1) below.

[Compound 6]

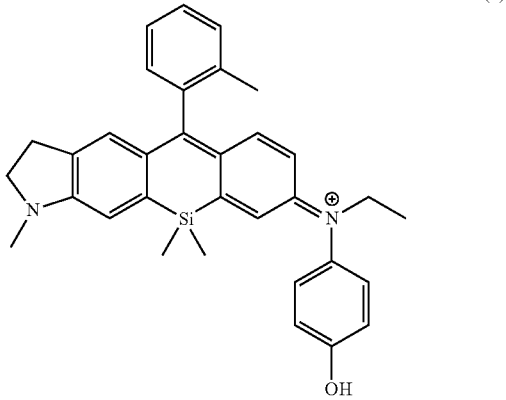

(1)

[15] The compound or salt thereof according to [1], represented by general formula (Ib) below, Y being —$OR^{13}$.

[Chemical Formula 7]

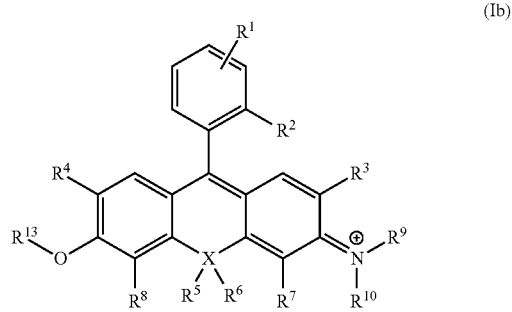

(Ib)

(where $R^1$-$R^{10}$, $R^{13}$, and X are as defined in formula (I))

[16] The compound or salt thereof according to [15], wherein $R^{13}$, $R^9$, or $R^{10}$ is a monovalent substituent cleaved by contact with an enzyme selected from the group consisting of peptidase, protease, lactamase, glycohydrolase, transferase, and oxidoreductase.

[17] The compound or salt thereof according to [16], wherein $R^{13}$, $R^9$, or $R^{10}$ is a monovalent substituent cleaved by contact with an enzyme selected from the group consisting of peptidase, protease, and lactamase.

[18] The compound or salt thereof according to [13] or [14], wherein the peptidase or protease is an enzyme selected from the group consisting of caspase, prostate-specific antigen, leucine aminopeptidase, and γ-glutamyl transpeptidase.

[19] The compound or salt thereof according to [1], represented by general formula (Ic) below, Y being —N=N—$R^{14}$.

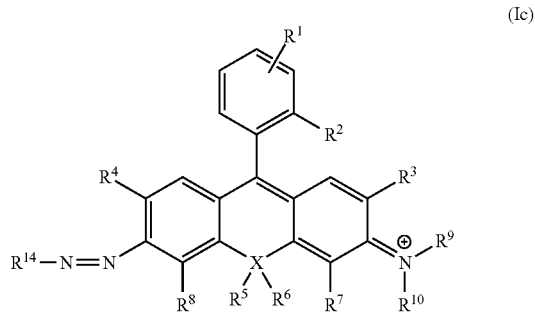

(Ic)

(where $R^1$-$R^{10}$, $R^{14}$, and X are as defined in formula (I), $R^9$ and $R^{10}$ not being a monovalent substituent cleaved by contact with a measured substance)

[20] The compound or salt thereof according to [19], wherein the aryl group of $R^{14}$ is a monocyclic aromatic group or a condensed aromatic group, and the aryl group has a substituent selected from an amino group and a dimethyl amino group.

[21] A fluorescent probe containing the compound defined in any one of [1] to [20].

[22] An active-oxygen-detecting fluorescent probe containing the compound of any one of [12] to [14].

[23] A low-oxygen-environment-detecting fluorescent probe containing the compound of [19] or [20].

[24] A method for manufacturing the compound represented by general formula (Ia) of [2] ($R^1$-$R^{12}$ and X are as defined above) or salt thereof, wherein the method comprises the following steps:

(a) reacting a 3-halo-N,N-diallyl aniline represented by general formula (II) (where $R^{16}$ represents a halogen atom) manufactured from a 3-halogenated aniline and an allyl halide, and a 3-halobenzene amine compound represented by formula (III) in the presence of formamide to produce a compound represented by general formula (IV) below;

[Chemical Formula 8]

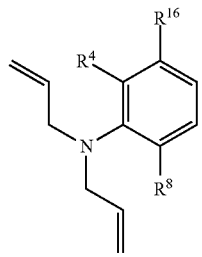

(II)

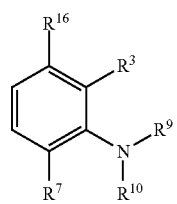

(III)

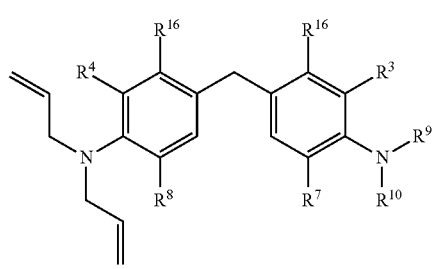

(IV)

(b) reacting the compound represented by general formula (IV) and X(Halo)$_2$($R^5$)($R^6$) (where Halo is a chlorine atom or a bromine atom; and X, $R^5$, $R^6$ are as defined above), and subsequently producing a compound represented by general formula (V) below by oxidation;

[Chemical Formula 9]

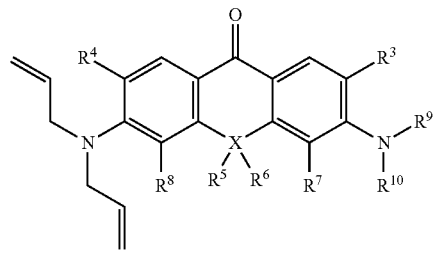

(V)

(c) manufacturing a compound represented by general formula (VI) below from a halobenzene derivative and the compound represented by general formula (V); and

[Chemical Formula 10]

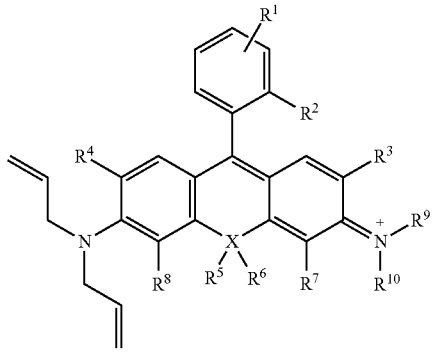

(VI)

(d) de-allylating the compound represented by general formula (VI), and manufacturing a compound in which $R^{11}$ and $R^{12}$ in general formula (Ia) are hydrogen atoms (when a protecting group is introduced into $R^1$ and $R^2$ to manufacture the compound of general formula (VI), the protecting group may be deprotected before, after, or simultaneously with step (d)).

[25] The method according to [24], further comprising a step of introducing, as $R^{11}$, a monovalent substituent cleaved by contact with a measured substance.

[26] A method for manufacturing the compound represented by general formula (Ia) of [2] ($R^1$-$R^{12}$ and X are as defined above) or salt thereof, wherein the method comprises the following steps:

(1) reacting a 3-halo-N,N-diallyl aniline represented by general formula (VII) (where $R^{16}$ represents a halogen atom) manufactured from a 3-haloaniline and an allyl halide in the presence of phosphorus oxychloride under basic conditions to manufacture a 3-halo-N,N-diallyl-4-hydroxymethylaniline represented by general formula (VIII);

[Chemical Formula 11]

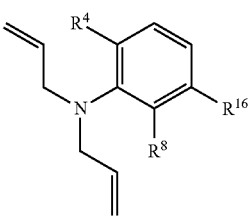

(VII)

-continued

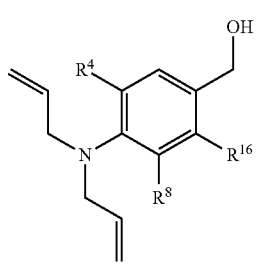

(VIII)

(2) reacting the 3-halo-N,N-diallyl-4-hydroxymethyl aniline and a 3-halobenzene amine compound represented by formula (IX) to manufacture a compound represented by general formula (X);

[Chemical Formula 12]

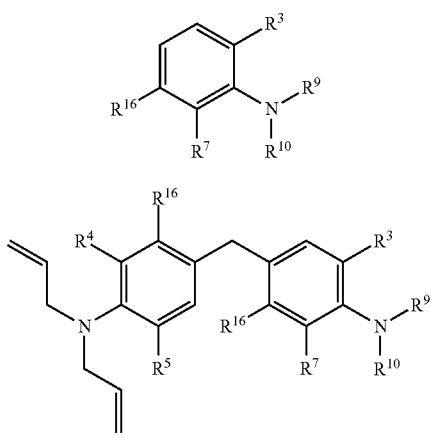

(IX)

(X)

(3) reacting the compound represented by general formula (X) and $X(Halo)_2(R^5)(R^6)$ (Halo is a chlorine atom or a bromine atom; and X, $R^5$, and $R^6$ are as defined above), and subsequently manufacturing, by oxidation, N,N-diallylamino-N',N'-dialkylamino-X-xanthone represented by formula (V) below;

[Chemical Formula 13]

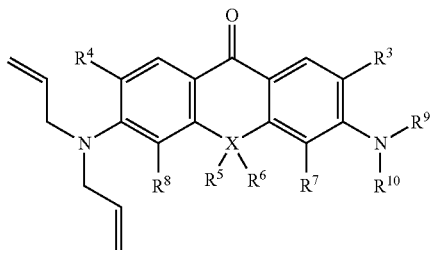

(V)

(4) manufacturing a compound represented by general formula (VI) below from the N,N-diallylamino-N',N'-dialkylamino-X-xanthone and a halobenzene derivative; and

[Chemical Formula 14]

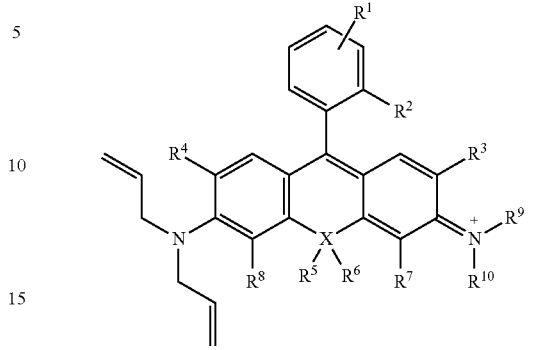

(VI)

(5) de-allylating the compound represented by general formula (VI), and manufacturing a compound in which $R^{11}$ and $R^{12}$ in general formula (Ia) are hydrogen atoms (when a protecting group is introduced into $R^1$ and $R^2$ to manufacture the compound of general formula (VI), the protecting group may be deprotected before, after, or simultaneously with step (4)).

[27] The method according to [26], further comprising a step for introducing, as $R^{11}$, a monovalent substituent cleaved by contact with a measured substance.

[28] A method for manufacturing the compound or salt thereof represented by general formula (Ib) of [15], wherein the method comprises the steps of:

(1) reacting a compound represented by general formula (XI) below, under basic conditions, with trifluoromethanesulfonic anhydride ($Tf_2O$) to manufacture a compound represented by general formula (XII) below;

[Chemical Formula 15]

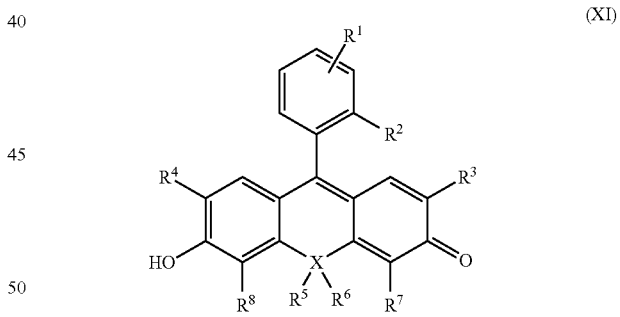

(XI)

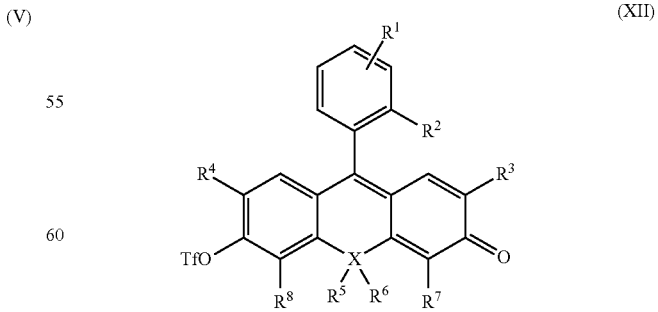

(XII)

(2) reacting the compound represented by general formula (XII) with an imine compound, and thereby manufacturing a compound represented by general formula (XIII); and

[Chemical Formula 16]

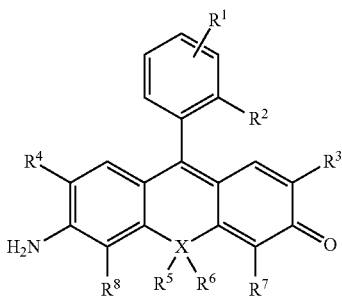

(XIII)

(3) optionally reacting the compound represented by general formula (XIII) with an alkyl halide.

[29] A method for manufacturing the compound or salt thereof represented by general formula (Ia-3) of [13], wherein the method comprises the steps of:

(1) reacting a compound of general formula (XIV) with potassium iodide, and thereby manufacturing a compound of general formula (XV);

[Chemical Formula 17]

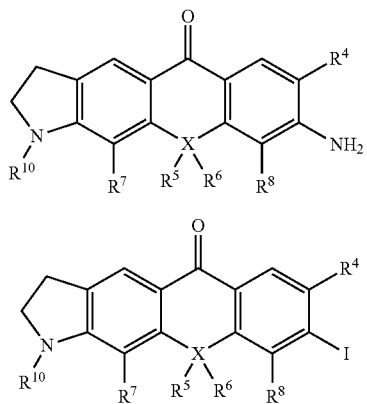

(XIV)

(XV)

(2) reacting the compound of general formula (XV) with N-alkyl-p-anisidine, in which the alkyl group has 1-6 carbons, and thereby manufacturing a compound of general formula (XVI);

[Chemical Formula 18]

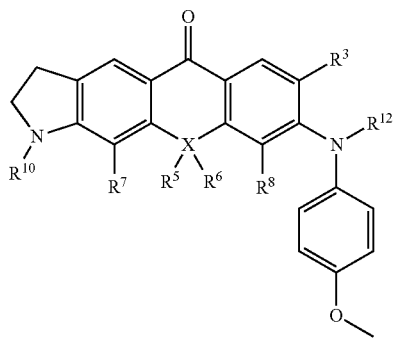

(XVI)

(3) reacting the compound of (XVI) with o-tolylmagnesium bromide, and subsequently adding an acid to manufacture a compound of general formula (XVII); and

[Chemical Formula 19]

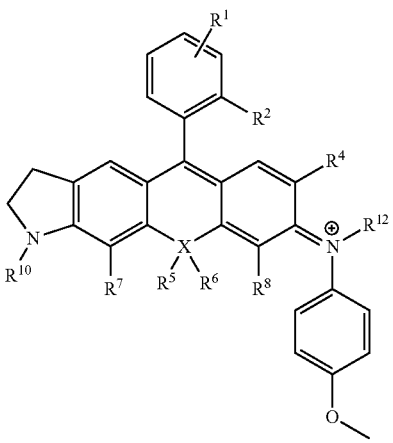

(XVII)

(4) reacting the compound of general formula (XVII) with boron tribromide, and thereby manufacturing a compound represented by general formula (Ia-3).

Advantages of the Invention

In accordance with the present invention, it is possible to provide a Si rhodamine (may hereinafter also be referred to as "asymmetrical Si rhodamine") of which a substituent group of the amino groups at position 3 and position 6 has an asymmetrical structure. In other words, only a Si rhodamine of which a substituent group of the amino groups at position 3 and position 6 has a symmetrical structure has been obtainable in the past. However, in accordance with the present invention, the substituent group of the amino groups at position 3 and position 6 has an asymmetrical structure, and it is therefore possible to selectively introduce a substituent group having various functions for only one of the amino groups. It is thereby possible to provide an exceptional labeling agent and a fluorescent probe capable of efficiently and quantitatively detecting protease and various other enzymes.

Furthermore, in the present invention, it is possible to select a substituent group of the amino group at position 3 and/or position 6 of the asymmetrical Si rhodamine to thereby provide a fluorescent dye that exhibits high fluorescence intensity in the red region and furthermore has absorbance in the near-infrared wavelength region extending from 650 nm to 900 nm.

In the present invention, it is possible to efficiently manufacture an asymmetrical Si rhodamine. In particular, the manufacturing method of the present invention makes it possible to provide an asymmetrical Si rhodamine in which a heterocyclic structure has been introduced in pyronin, which is the basic skeleton of rhodamine.

In accordance with the present invention, rhodol and analogues thereof can be efficiently manufactured.

The asymmetrical Si rhodamine of the present invention has the feature of having two clear peaks in the short wavelength and long wavelength in the absorbance spectrum and the fluorescence spectrum. The asymmetrical Si rhodamine of the present invention can accordingly be advantageously used for ratio measurement (a technique for simultaneously measuring fluorescence intensity at two different wavelengths and calculating the ratio thereof).

Furthermore, in the asymmetrical Si rhodamine and rhodol of the present invention, a compound in which a monovalent substituent group cleaved by contact with a measured substance has been introduced is useful as a fluorescent probe that allows various enzymes and the like to be measured with high sensitivity.

In the asymmetrical Si rhodamine of the present invention, it is furthermore possible to provide a near-infrared fluorescent probe for exceptional active-oxygen detection by bonding an aromatic ring to the nitrogen atom of a xanthene ring.

Furthermore, incorporating an azo group having an aryl group in the conjugated system of the asymmetrical Si rhodamine of the present invention makes it possible to provide an excellent near-infrared fluorescent probe for detecting low-oxygen environments.

BEST MODE FOR CARRYING OUT THE INVENTION

Figure 1A:
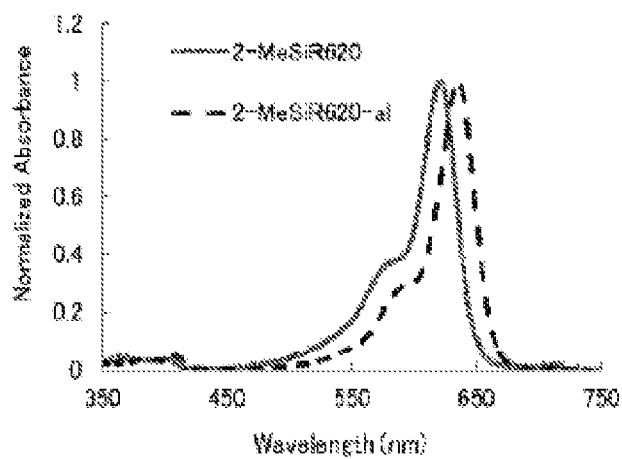
FIG. 1a Result of measuring absorbance profile of 2-MeSiR620 (Compound 1) and 2-MeSiR620-a1 (Compound 2).

In the present invention, unless otherwise noted, "alkyl group" or alkyl moiety of a substituent (e.g., an alkoxy group or the like) containing an alkyl moiety refers to, e.g., a $C_{1-6}$, preferably $C_{1-4}$, and more preferably $C_{1-3}$ alkyl group comprising a straight chain, branched chain, ring, or combination thereof. More specifically, examples of the alkyl group include a methyl group, ethyl group, n-propyl group, isopropyl group, cyclopropyl group, n-butyl group, sec-butyl group, isobutyl group, tert-butyl group, cyclopropylmethyl group, n-pentyl group, and n-hexyl group.

In the present invention, the term "halogen atom" may be a fluorine atom, chlorine atom, bromine atom, or iodine atom, and is preferably a fluorine atom, chlorine atom, or bromine atom.

One mode of the present invention is a compound or salt thereof represented by general formula (I) below.

[Chemical Formula 20]

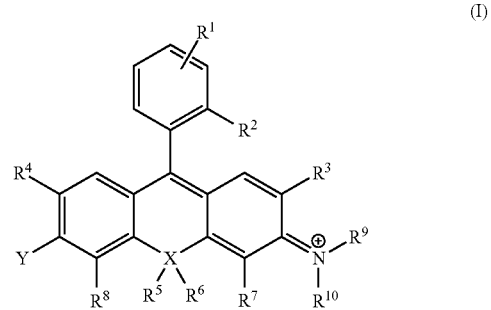

(I)

In general formula (I), $R^1$ represents a hydrogen atom or one to four same or different monovalent substituent groups present on a benzene ring. When $R^1$ represents a monovalent substituent group present on a benzene ring, it is preferred that one or two same or different substituent groups be present on the benzene ring. When $R^1$ represents one or more monovalent substituent groups, the substituent group can be substituted at any position on the benzene ring. Preferably, $R^1$ represents a hydrogen atom, or is the case in which a single substituent group is present.

The type of monovalent substituent group represented by $R^1$ is not particularly limited; preferred examples may be selected from the group consisting of a $C_{1-6}$ alkyl group, a $C_{1-6}$ alkenyl group, a $C_{1-6}$ alkynyl group, a $C_{1-6}$ alkoxy group, a hydroxyl group, a carboxy group, a sulfonyl group, an alkoxycarbonyl group, a halogen atom, and an amino group. These monovalent substituent groups may furthermore have one or more substituent groups. For example, one or more of a halogen atom, carboxy group, sulfonyl group, hydroxyl group, amino group, alkoxy group, or the like may be present in the alkyl group represented by $R^1$, and, for example, the alkyl group represented by $R^1$ may be an alkyl halide group, a hydroxyalkyl group, a carboxyalkyl group, an aminoalkyl group, or the like. Also, for example, one or more alkyl groups may be present in the amino group represented by $R^1$, and the amino group represented by $R^1$ may be a monoalkyl amino group or a dialkyl amino group. Furthermore, in the case that the alkoxy group represented by $R^1$ has a substituent group, examples thereof include a carboxy-substituted alkoxy group and an alkoxycarbonyl-substituted alkoxy group, and more specific examples include a 4-carboxybutoxy group and a 4-acetoxymethyl-oxycarbonylbutoxy group.

In a preferred aspect, $R^1$ is a $C_{1-6}$ alkyl group or other monovalent substituent group, and the substituent group is present at position 6 on the benzene ring.

In general formula (I), $R^2$ represents a monovalent substituent group. The type of monovalent substituent group represented by $R^2$ is not particularly limited; in similar fashion to $R^1$, preferred examples may be selected from the group consisting of a $C_{1-6}$ alkyl group, a $C_{1-6}$ alkenyl group, a $C_{1-6}$ alkynyl group, a $C_{1-6}$ alkoxy group, a hydroxyl group, a carboxy group, a sulfonyl group, an alkoxycarbonyl group, a halogen atom, and an amino group.

In general formula (I), $R^3$ and $R^4$ independently represent a hydrogen atom, a $C_{1-6}$ alkyl group, or a halogen atom. When $R^3$ or $R^4$ represents an alkyl group, one or more halogen atoms, carboxy groups, sulfonyl groups, hydroxyl groups, amino groups, alkoxy groups, or the like may be present in the alkyl group, and, for example, the alkyl group represented by $R^3$ or $R^4$ may be an alkyl halide group, a hydroxyalkyl group, a carboxyalkyl group, or the like. $R^3$ and $R^4$ are, independently, preferably a hydrogen atom or a halogen atom, and it is more desirable that $R^3$ and $R^4$ both be hydrogen atoms, or $R^3$ and $R^4$ both be fluorine atoms or chlorine atoms.

In the general formula (I), $R^5$ and $R^6$ independently represent a $C_{1-6}$ alkyl group or aryl group. $R^5$ and $R^6$ are, independently, preferably a $C_{1-3}$ alkyl group, and $R^5$ and $R^6$ are both more preferably a methyl group. One or more halogen groups, carboxy groups, sulfonyl groups, hydroxyl groups, amino groups, alkoxy groups, or the like may be present in the alkyl group represented by $R^5$ and $R^6$, and the alkyl group represented by $R^5$ or $R^6$ may be, e.g., an alkyl halide group, a hydroxyalkyl group, a carboxyalkyl group, or the like. When $R^5$ or $R^6$ represent an aryl group, the aryl group may be a monocyclic aromatic group or condensed aromatic group, and the aryl ring may include one or more ring-structured heteroatoms (e.g., nitrogen atom, oxygen atom, sulfur atom, or the like). A phenyl group is preferred as the aryl group. One or more substituent groups may be present on the aryl ring. One or more substituent groups, e.g., a halogen atom, carboxy group, sulfonyl group, hydroxyl group, amino group, alkoxy group, or the like may be present.

In general formula (I), $R^7$ and $R^8$ are, independently, a hydrogen atom, $C_{1-6}$ alkyl group, or halogen atom, which is that same as that described for $R^3$ and $R^4$. $R^7$ and $R^8$ are preferably both hydrogen atoms, both chlorine atoms, or both fluorine atoms.

In general formula (I), $R^9$ and $R^{10}$ are, independently, a hydrogen atom, $C_{1-6}$ alkyl group, or monovalent substituent cleaved by contact with a measured substance. $R^9$ or $R^{10}$ optionally forms, together with $R^3$ or $R^7$, a 5-7-member heterocyclyl or heteroaryl containing a nitrogen atom to which $R^9$ or $R^{10}$ binds, and optionally contains 1-3 additional heteroatoms selected from the group consisting of oxygen atoms, nitrogen atoms, and sulfur atoms as ring-constituting members; the heterocyclyl or heteroaryl furthermore optionally being substituted by a $C_{1-6}$ alkyl, $C_{2-6}$ alkenyl, $C_{2-6}$ alkynyl, $C_{6-10}$ aralkyl group (benzyl group, phenethyl group, or the like), or $C_{6-10}$ alkyl-substituted alkenyl group. Examples of the heterocyclyl or heteroaryl formed in this manner include and are not limited to pyrrolidone, piperidine, hexamethyleneimine, pyrrole, imidazole, pyrazole, oxazole, and thiazole.

In general formula (I), Y is selected from (1) —$NR^{11}R^{12}$, (2) —$OR^{13}$, or (3) —N=N—$R^{14}$.

Here, $R^{11}$ is a hydrogen atom, $C_{1-6}$ alkyl group, or monovalent substituent cleaved by contact with a measured substance. $R^{12}$ is a hydrogen atom, $C_{1-6}$ alkyl group, or acyl group.

When $R^{11}$ or $R^{12}$ is an alkyl group, one or more of a halogen atom, carboxy group, sulfonyl group, hydroxyl group, amino group, alkoxy group, or the like may be present in the alkyl group, and examples of the alkyl group represented by $R^{11}$ or $R^{12}$ include alkyl halide group, hydroxyalkyl group, and carboxyalkyl group.

When $R^{11}$ and $R^{12}$ are alkyl groups, $R^{11}$ and $R^{12}$ may form a 5-7-member heterocyclyl containing a nitrogen atom to which these bind. In this case, the heterocyclyl may contain 1-3 additional heteroatoms selected from the group consisting of oxygen atoms, nitrogen atoms, and sulfur atoms as ring-constituting members; and the heterocyclyl may be substituted by a $C_{1-6}$ alkyl group.

Examples of the acyl group of $R^{12}$ include a formyl group, acetyl group, propionyl group, and benzoyl group, but no limitation is imposed thereby.

$R^{13}$ is a hydrogen atom or monovalent substituent cleaved by contact with a measured substance.

$R^{14}$ is an aryl group. The aryl group may be a monocyclic aromatic group or a condensed aromatic group. The aryl group is preferably a phenyl group or a naphthyl group. One or more substituent groups may be present in the aryl ring. The substituent group is preferably an amino group (e.g., —$NH_2$, $C_{1-6}$ monoalkyl amino group or dialkyl amino group) or the like. The substituted position is preferably the para position in relation to the azo group.

When Y is —$NR^{11}R^{12}$ in general formula (I), $R^9$ and $R^{10}$ are not monovalent substituents cleaved by contact with a measured substance. Also, when Y is —$NR^{11}R^{12}$ and $R^{11}$ and $R^{12}$ are hydrogen atoms, $R^9$ and $R^{10}$ are not both hydrogen atoms.

When $R^{11}$ and $R^{12}$ are hydrogen atoms, at least one of $R^9$ and $R^{10}$ is not a hydrogen atom, but when one of $R^9$ and $R^{10}$ is a hydrogen atom, the other is a $C_{1-6}$ alkyl group, or together with $R^3$ or $R^7$, a 5-7-member heterocyclyl or heteroaryl containing a nitrogen atom to which $R^9$ or $R^{10}$ binds, and may include 1-3 additional heteroatoms selected from the group consisting of oxygen atoms, nitrogen atoms, and sulfur atoms as ring-constituting members. The heterocyclyl or heteroaryl may be substituted by a $C_{1-6}$ alkyl, $C_{2-6}$ alkenyl, $C_{2-6}$ alkynyl, $C_{6-10}$ aralkyl, or $C_{6-10}$ alkyl-substituted alkenyl group.

When Y is —$OR^{13}$ and $R^{13}$ is a hydrogen atom in general formula (I), $R^9$ or $R^{10}$ may be a monovalent substituent cleaved by contact with a measured substance.

When Y is —N=N—R$^{14}$ in general formula (I), R$^9$ and R$^{10}$ are not a monovalent substituent cleaved by contact with a measured substance.

In general formula (I), X is a silicon atom, germanium atom, or tin atom, preferably a silicon atom or germanium atom, and a silicon atom is particularly preferred.

One mode of the present invention is the compound or salt thereof represented by the general formula (Ia) below.

[Chemical Formula 21]

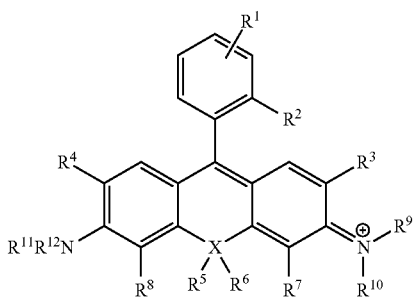

(Ia)

In formula (Ia), R$^1$ to R$^{12}$ are as defined in formula (I), but R$^9$ and R$^{10}$ are not monovalent substituents cleaved by contact with a measured substance. Also, when R$^{11}$ and R$^{12}$ are hydrogen atoms, R$^9$ and R$^{10}$ are not both hydrogen atoms.

When R$^{11}$ and R$^{12}$ are hydrogen atoms, at least one of R$^9$ and R$^{10}$ is not a hydrogen atom, but when one of R$^9$ and R$^{10}$ is a hydrogen atom, the other is a C$_{1-6}$ alkyl group, or together with R$^3$ or R$^7$, a 5-7-member heterocyclyl or heteroaryl containing a nitrogen atom to which R$^9$ or R$^{10}$ binds, and may include 1-3 additional heteroatoms selected from the group consisting of oxygen atoms, nitrogen atoms, and sulfur atoms as ring-constituting members. Furthermore, the heterocyclyl or heteroaryl may be substituted by a C$_{1-6}$ alkyl, C$_{2-6}$ alkenyl, C$_{2-6}$ alkynyl, C$_{6-10}$ aralkyl, or C$_{6-10}$ alkyl-substituted alkenyl group.

In a preferred embodiment, R$^{11}$ and R$^{12}$ are hydrogen atoms, and R$^9$ and R$^{10}$ are same or different C$_{1-6}$ alkyl groups.

In a preferred embodiment, R$^{11}$ is a hydrogen atom, R$^{12}$ is a C$_{1-6}$ alkyl group, and R$^9$ and R$^{10}$ are same or different C$_{1-6}$ alkyl groups.

In another preferred embodiment, R$^{11}$ is a monovalent substituent cleaved by contact with a measured substance, R$^{12}$ is a hydrogen atom or a C$_{1-6}$ alkyl group, and R$^9$ and R$^{10}$ are same or different C$_{1-6}$ alkyl groups.

In another preferred embodiment, R$^9$ or R$^{10}$, together with R$^3$ or R$^7$, forms a 5-7-member heterocyclyl or heteroaryl containing a nitrogen atom to which R$^9$ or R$^{10}$ binds (Here, the heterocyclyl or heteroaryl may include 1-3 additional heteroatoms selected from the group consisting of oxygen atoms, nitrogen atoms, and sulfur atoms as ring-constituting members. Furthermore, the heterocyclyl or heteroaryl may be substituted by a C$_{1-6}$ alkyl, C$_{2-6}$ alkenyl, C$_{2-6}$ alkynyl, C$_{6-10}$ aralkyl, or C$_{6-10}$ alkyl-substituted alkenyl group.).

In another preferred embodiment, R$^9$ together with R$^3$ forms a 5-7-member heterocyclyl or heteroaryl containing a nitrogen atom to which R$^9$ binds.

In a preferred aspect of the above-noted embodiment, R$^{11}$ and R$^{12}$ are hydrogen atoms.

In another preferred aspect of the embodiment, R$^{11}$ is a hydrogen atom and R$^{12}$ is a C$_{1-6}$ alkyl group or acyl group.

In another preferred aspect of the embodiment, R$^{11}$ is a hydrogen atom and R$^{12}$ is a carboxyalkyl group.

In another preferred aspect of the embodiment, R$^{11}$ is a monovalent substituent cleaved by contact with a measured substance, and R$^{12}$ is a hydrogen atom or a C$_{1-6}$ alkyl group.

Furthermore, a preferred embodiment of the present invention is the compound or salt thereof represented by the formula (Ia-1) below.

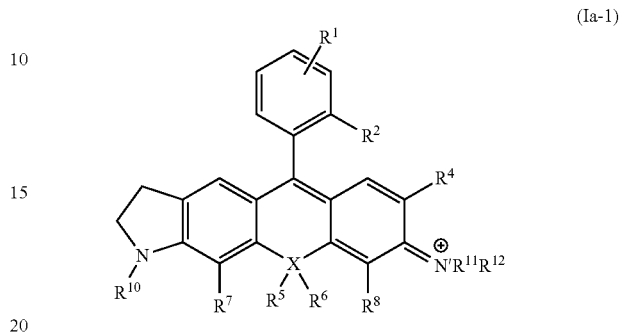

(Ia-1)

In general formula (Ia-1), R$^1$-R$^8$, R$^{10}$-R$^{12}$, and X are as defined in general formula (Ia)

In a preferred aspect of the above-noted embodiment, R$^{11}$ and R$^{12}$ are hydrogen atoms.

In another preferred aspect of the above-noted embodiment, R$^{11}$ is a hydrogen atom and R$^{12}$ is a C$_{1-6}$ alkyl group.

In another preferred aspect of the above-noted embodiment, R$^{11}$ is a hydrogen atom and R$^{12}$ is a carboxyalkyl group.

In another preferred aspect of the above-noted embodiment, R$^{11}$ is a hydrogen atom and R$^{12}$ is a C$_{1-6}$ acyl group, preferably acetyl group.

In another preferred aspect of the above-noted embodiment, R$^{11}$ is a monovalent substituent cleaved by contact with a measured substance, and R$^{12}$ is a hydrogen atom or a C$_{1-6}$ alkyl group.

In another preferred embodiment, R$^{11}$ and R$^{12}$ form a 5-7-member heterocyclyl containing a nitrogen atom to which R$^{11}$ and R$^{12}$ binds (here, the heterocyclyl may include 1-3 additional heteroatoms selected from the group consisting of oxygen atoms, nitrogen atoms, and sulfur atoms as ring-constituting members. Furthermore, the heterocyclyl may be substituted by a C$_{1-6}$ alkyl group.).

Here, the 5-7-member heterocyclyl containing a nitrogen atom to which R$^{11}$ and R$^{12}$ bind preferably contains a further nitrogen atom as a ring-constituting member. A preferred example of such a heterocyclyl is a piperazine ring.

A further preferred embodiment of the present invention is the compound or salt thereof represented by the general formula (Ia-2) below.

[Chemical Formula 22]

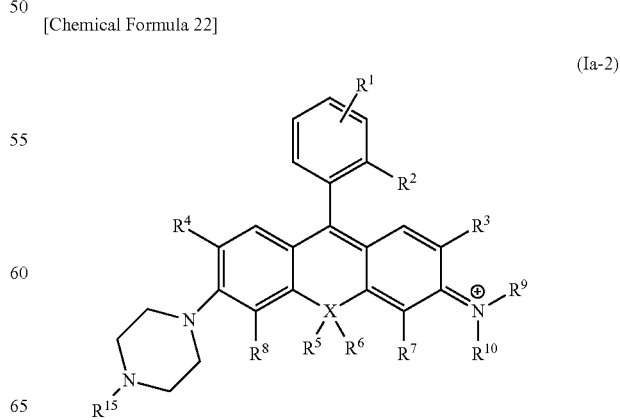

(Ia-2)

In general formula (Ia-2), $R^1$-$R^{10}$ and X are as defined in general formula (Ia). $R^{15}$ represents an $C_{1-6}$ alkyl group or alkylcarboxy group, and preferred examples of the alkyl group include a methyl group, ethyl group, and propyl group.

In the asymmetrical Si rhodamine of the present invention, a piperazine ring is introduced to thereby make it possible to provide an acid-environment-detecting fluorescent probe capable of varying fluorescence characteristics in an intracellular acid environment.

A further preferred embodiment of the present invention is the compound or salt thereof represented by the general formula (Ib) below.

[Chemical Formula 23]

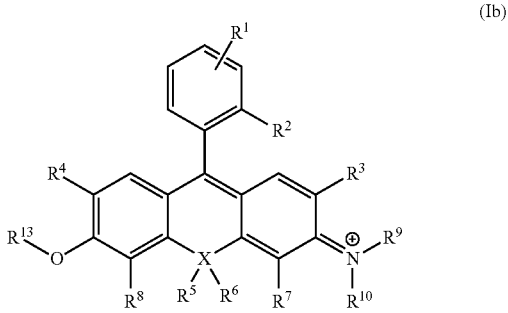

(Ib)

In general formula (Ib), $R^1$-$R^{10}$ and $R^{13}$ are as defined in general formula (I). When $R^{13}$ is a hydrogen atom, $R^9$ or $R^{10}$ may be a monovalent substituent cleaved by contact with a measured substance.

In a preferred embodiment, $R^{13}$ is a hydrogen atom, and $R^9$ and $R^{10}$ are hydrogen atoms.

In another preferred embodiment, $R^{13}$ is a hydrogen atom, and $R^9$ and/or $R^{10}$ are $C_{1-6}$ alkyl groups.

In a preferred embodiment, $R^{13}$ is a hydrogen atom, and $R^9$ or $R^{10}$ is a monovalent substituent cleaved by contact with a measured substance.

In the present invention, the type of measured substance is not particularly limited; examples include enzymes, metal ions (e.g., sodium ions, lithium ions, and other alkali metal ions; calcium ions and other alkaline-earth metal ions; magnesium ions, zinc ions, and the like), non-metal ions (carbonate ions, and the like), active-oxygen species (e.g., a hydroxyl radical, peroxynitrite, hypochlorous acid, and hydrogen peroxide), and low-oxygen environments. Preferred are enzymes, active-oxygen species, or low-oxygen environments.

Examples of the monovalent substituent cleaved by contact with a measured substance include the following substituent groups.

a) as a monovalent substituent group for chelating protons, a capturing group represented by —$CR^{20}$-A-$NR^{21}R^{22}$ (wherein, $R^{20}$, $R^{21}$, and $R^{22}$ are, independently, a hydrogen atom, $C_{1-6}$ alkyl group optionally having a substituent group, an aryl group optionally having a substituent group, and a $C_{1-3}$ alkylene group to which $R^{20}$ and $R^{21}$, or $R^{20}$ and $R^{22}$ have bonded; and A is a $C_{1-3}$ alkylene group optionally having a substituent group).

b) as a monovalent substituent group for chelating metal ions, a substituent group disclosed in [Chemical Formula 4] on page 8 of International Publication WO 2005/085811 for sodium ions, lithium ions, potassium ions, and magnesium ions (where the benzene ring to which $R^3$ binds as represented in [Chemical Formula 4] of page 8 of the International Publication WO 2005/085811 corresponds to the benzene ring to which $R^1$ and $R^2$ bind in the present specification); a substituent group in which —$N(CH_2COOR^{23})_2$ (where $R^{23}$ is a hydrogen atom, or a metal ion or ester) is present at a distance of 5-8 atoms (e.g., —$CON[CH_2$—$CON(CH_2COOR^{23})_2]_2$, the substituent group disclosed in line 37, page 10 to line 19, page 12 of Japanese Patent Application Publication No. 2005-201845) for calcium ions; and a substituent group represented by —NH—$CH_2CH_2$—$NR^{24}R^{25}$ (where $R^{24}$ and $R^{25}$ are, independently, a hydrogen atom, 2-pyridylmethyl group, 2-pyridylethyl group, 2-methyl-6-pyridylmethyl group, or 2-methyl-6-pyridylethyl group, and are not simultaneously both hydrogen atoms) for zinc ions.

c) as a monovalent substituent group cleaved by contact with an active-oxygen species, a p-aminophenyloxymethyl group, p-hydroxyphenyloxymethyl group, p-aminophenyl group, and p-hydroxyphenyl group for peroxynitrite, hydroxyl radical, and hypochlorous acid.

d) for a low-oxygen environment, a substituent group represented by —CO—$N(R^{26})$—$B^1$—$N(R^{27})$—$B^2$—$(B^3)$r-p-$C_6H_4$—N=N—Ar—$R^{28}$ (where, $R^{26}$ and $R^{27}$ are, independently, a hydrogen atom or a $C_{1-6}$ alkyl group, $R^{26}$ and $R^{27}$ may bind to each other and become a $C_{2-6}$ alkylene group; $B^1$ is a $C_{1-6}$ alkylene group; $B^2$ is a single bond, —CO—, or —$SO_2$—; $B^3$ is —O-G-$N(R^{29})$— (where G is a $C_{1-6}$ alkylene group and $R^{29}$ is a hydrogen atom or a $C_{1-6}$ alkyl group); r is 0 or 1, p-$C_6H_4$— is a p-phenylene group; Ar is an aryl diyl group, and $R^{28}$ is a monoalkyl amino group or a dialkyl amino group.)

Examples of enzymes include reductase, oxidase, and hydrolase. Although no limitation is imposed thereby, additional examples include β-lactamase, cytochrome P450 oxidase, β-galactosidase, β-glucosidase, β-glucuronidase, β-hexosaminidase, lactase, alkaline phosphatase, matrix metalloprotease, glutamyl transferase, and other enzymes useful in diagnosing such as infectious diseases and cancers. Particularly preferred among enzymes is hydrolase. Typical examples of hydrolase include β-galactosidase, β-lactamase, alkaline phosphatase, matrix metalloprotease, and glutamyl transferase, but the hydrolase is not particularly limited to the foregoing.

When a hydrolase is used as the measured substance, it is possible to select a functional group or a compound acting as a specific enzyme substrate and to design the compounds of general formulas (I), (Ia), and (Ib) so that the compound undergoes hydrolysis induced by the enzyme to produce a compound in which $R^{11}$ ($R^9$, $R^{10}$, or $R^{13}$) is a hydrogen atom. For example, when a sugar hydrolase is used as the measured substance, it is possible to use a residue of a sugar compound acting as the enzyme substrate as $R^{11}$ ($R^9$, $R^{10}$, or $R^{13}$). The hydroxyl group of the sugar compound, or the amino group or other functional group may be protected by a suitable protecting group as required. Such compounds having such a protecting group are all included in the scope of the present invention.

When peptidase or protease is used as the measured substance, examples of the monovalent substituents cleaved by contact with an enzyme include substituent groups disclosed as a GGT fluorescent probe and formulas (a) to (g) in the present specification, and acyl residues derived from 20 types of L-amino acids constituting proteins that contain an amino acid residue (an amino acid residue is a group in which one hydrogen atom has been displaced from a carboxy group or amino group of an amino acid) substituted by compounds (1) to (7) disclosed in [Chemical Formula 4] of page 12 of International Publication WO 2010/095450 (the foregoing amino acid residue optionally binds to an amino group to which $R^{11}$, $R^9$, $R^{10}$, or $R^{13}$ of general formula (I) of the present specification binds). Examples of that may be used as the monovalent substituent cleaved by contact with an enzyme include: the substituent group disclosed in formula (h) of the present specification when lactamase is used as the measured substance; a galactosyl group, glucosyl group, and glucuronosyl group when a sugar hydrolase is used as the measured substance; and an amino group, carboxy group, and thiol group when a glucuronic acid transferase is used as the measured substance.

When glutathione is used as the measured substance, the substituent group or the like disclosed in formula (i) in the present specification can be used as the monovalent substituent cleaved by contact with the measured substance.

When $R^{11}$ ($R^9$, $R^{10}$, or $R^{13}$) is a p-aminophenyl group or a p-hydroxyphenyl group and the compound undergoes hydrolysis by contact with an active-oxygen species, a compound in which $R^{11}$ ($R^9$, $R^{10}$, or $R^{13}$) is a hydrogen atom is generated, and an active-oxygen species can therefore be used as a measured substance. An active-oxygen-species fluorescent probe having a p-aminophenyl group or a p-hydroxyphenyl group is disclosed in, e.g., International Publication WO 2001/064664, International Publication WO 2004/040296, U.S. Pat. No. 7,378,282, and other publications. Therefore, the fluorescent probe of the present invention can be used in the same manner as the fluorescent probes disclosed in these documents.

The monovalent substituent cleaved by contact with these measured substances may be directly substituted by the compound or salt thereof represented by general formula (I), or may be substituted by the compound or salt thereof represented by general formula (I) via a spacer (linker). Examples of spacers include a substituted or unsubstituted alkyl group, ethylene glycol group, diethylene glycol group, and triethylene glycol group, but no limitation is imposed thereby.

In general formulas (I), (Ia), or (Ib), the compound, which is a monovalent substituent in which $R^{11}$, $R^9$, $R^{10}$, or $R^{13}$ is cleaved by contact with a measured substance, can be advantageously used as a fluorescent probe. In this case, it is possible to generate a compound (corresponding to a compound in which $R^{11}$, $R^9$, or $R^{10}$ in formula (I) has become an unsubstituted amino group) in which the substituent group of $R^{11}$, $R^9$, $R^{10}$, or $R^{13}$ is cleaved by contact of the fluorescent probe with a measured substance and the absorbance wavelength is shifted to a long wavelength, and the compound can be advantageously used as a fluorescent probe for measuring a measured substance. Examples of a measured substance include an enzyme (peptidase, protease, lactamase, glycohydrolase, transferase, oxidoreductase, or the like) and glutathione. Preferred examples of the enzyme are peptidase, protease, or lactamase.

The type of peptidase or protease is not particularly limited in the compound of the present invention represented by general formula (I) in which $R^{11}$, $R^9$, $R^{10}$, or $R^{13}$ is an acyl group as long as the type allows the acyl group to be hydrolyzed, and the peptidase may be an endopeptidase or an exopeptidase, and the protease may be an endoprotease or an exoprotease. For example, in order to measure a peptidase or protease having a specific amino acid or peptide as a substrate, an acyl residue derived from the peptide or amino acid can be used as $R^{11}$, $R^9$, $R^{10}$, or $R^{13}$, and using a compound designed in this manner makes it possible to specifically measure specific peptidase or protease (the acyl residue derived from the peptide or amino acid is a partial structure remaining after the hydroxyl group has been removed from the carboxy group of an amino acid). From this viewpoint, an acyl residue derived from a peptide or derived from an amino acid, and which can be hydrolyzed by peptidase or protease, is preferably used as $R^{11}$, $R^9$, $R^{10}$, or $R^{13}$ for a fluorescent probe for peptidase or protease. For example, it is possible to use an acyl residue derived from 20 types of L-amino acids constituting protein, or to use an acyl residue derived from selenocysteine, pyrrolysine, cystine, hydroxyproline, hydroxylysine, thyroxine, O-phosphoserine, desmosine, β-alanine, sarcosine, ornithine, creatine, γ-aminobutyric acid, opine or the like.

The following substituent groups are advantageous examples of $R^{11}$ ($R^9$, $R^{10}$, or $R^{13}$) when the peptidase is leucine aminopeptidase (LAP).

[Chemical Formula 24]

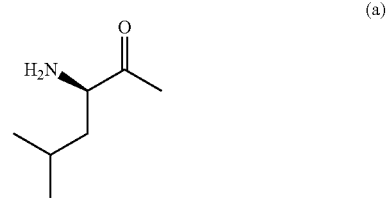

(a)

The following substituent group is an advantageous example of $R^{11}$ when the peptidase is γ-glutamyl transpeptidase (GGT). For example, using a compound having the following substituent group as $R^{11}$ in place of γGlu-RhoHM in accordance with the method disclosed in International Publication WO 2011/087000 makes it possible to specifically measure cancer cells and cancer tissue, and the compound can be used as a cancer diagnostic agent.

[Chemical Formula 25]

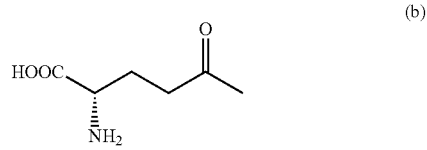

(b)

The following substituent groups are advantageous examples of $R^{11}$ ($R^9$, $R^{10}$, or $R^{13}$) when the protease is caspase-3.

[Chemical Formula 26]

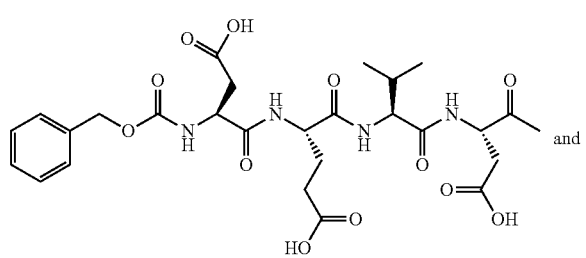

(c)

and

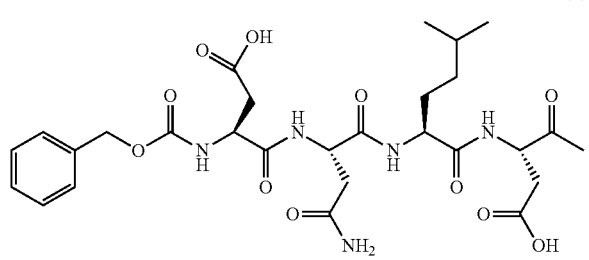

The following substituent groups are advantageous examples of $R^{11}$ ($R^9$, $R^{10}$, or $R^{13}$) when the protease is a calpain.

[Chemical Formula 27]

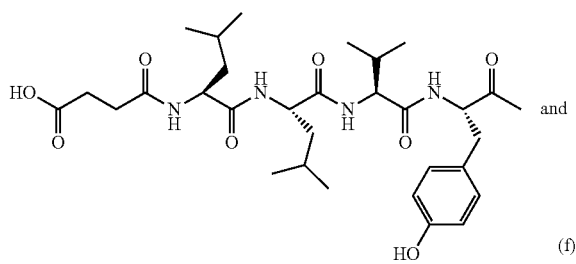

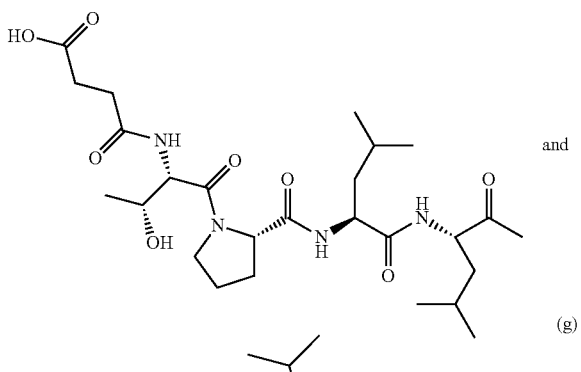

The following substituent group is an advantageous example of $R^{11}$ ($R^9$, $R^{10}$, or $R^{13}$) when the lactamase is β-lactamase.

[Chemical Formula 28]

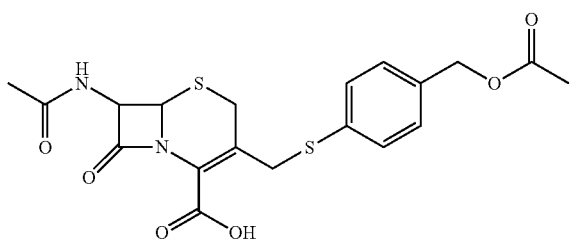

The following substituent group is an advantageous example of $R^{11}$ ($R^9$, $R^{10}$, or $R^{13}$) when the measured substance cleaved by contact is glutathione.

[Chemical Formula 29]

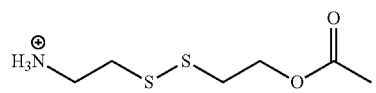

Another preferred mode of the present invention is the compound or salt thereof represented by general formula (Ic) below.

[Chemical Formula 30]

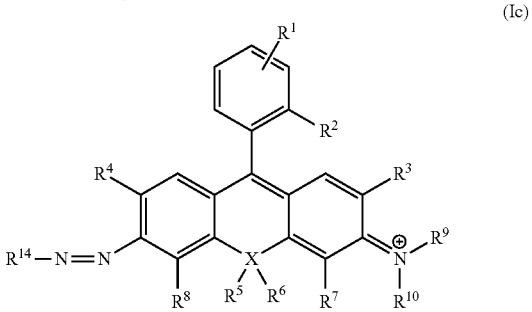

In general formula (Ic), $R^1$-$R^{10}$, $R^{14}$, and X are as defined in general formula (I).

$R^{14}$ is an aryl group and the aryl group may be a monocyclic aromatic group or a condensed aromatic group. The aryl group is preferably a phenyl group or a naphthyl group. One or more substituent groups may be present on the aryl ring. The substituent group is preferably an amino group (e.g., —$NH_2$ group, $C_{1-6}$ monoalkyl amino group, or dialkyl amino group) or the like. The substituted position is preferably the para position in relation to the azo group.

The compound of general formula (Ic) has a structure in which the amino group at position 6 in a asymmetrical Si rhodamine has been substituted by an azo group having an aryl group. Having such a structure, the compound of general formula (Ic) has a feature in becoming non-fluorescent because reductive reactions are accelerated by various reductases in a low-oxygen environment in vivo and an azo group is incorporated in a conjugated system of asymmetrical Si rhodamine. The compound of general formula (Ic) is thereby capable of providing a fluorescent probe for detecting a low-oxygen environment.

Examples of a reductase include NADPH cytochrome P-450 reductase, cytochrome P-450, NADPH-flavin reductase, and NADH-b5 reducatse.

Another preferred embodiment of the present invention is a compound or salt thereof in which $R^{11}$ in the general formula (Ia) is a monovalent substituent group cleaved by contact with a measured substance, and the substituent group is an aromatic ring. When $R^{11}$ is an aromatic ring, the bond between the aromatic ring and the substituent group is cleaved by an active-oxygen species, and it is possible to provide a useful probe for near-infrared-light active-oxygen detection.

Examples of the aromatic ring include a phenol group, aminophenyl group, and phenol group and aminophenol group in which a methyl group, ethyl group, propyl group, halogen group, methoxy group, allyl group, carboxy group, or the like has bonded at the ortho or meta positions thereof, a phenol group and aminophenyl group being preferred.

In a further preferred embodiment, $R^{11}$ is a monovalent substituent group cleaved by contact with a measured substance, and the substituent group is an aromatic ring; and $R^3$ and $R^9$ together preferably form a 5-7-member heterocyclyl

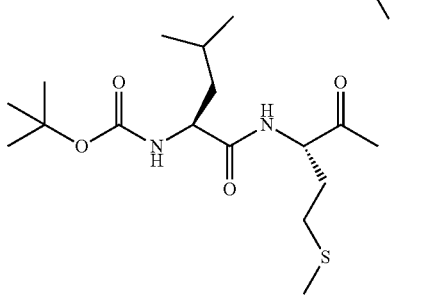

or heteroaryl containing a nitrogen atom to which $R^9$ binds. $R^{12}$ is preferably a $C_{1-6}$ alkyl group.

One preferred embodiment is the compound or salt thereof represented by the general formula (Ia-3) below.

[Chemical Formula 31]

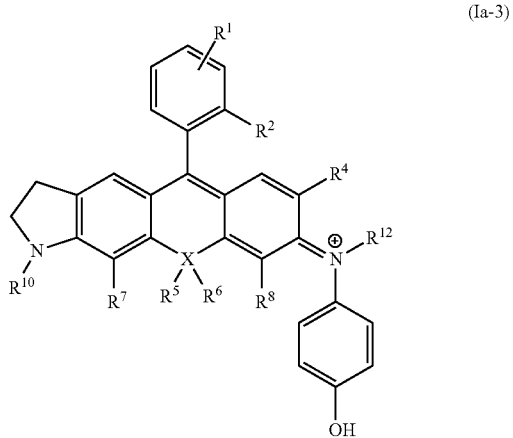

(Ia-3)

In general formula (Ia-3), $R^1$-$R^2$, $R^4$-$R^8$, $R^{10}$, $R^{12}$, and X are as defined in general formula (Ia).

A non-limiting example of such a compound includes the following compound.

[Chemical Formula 32]

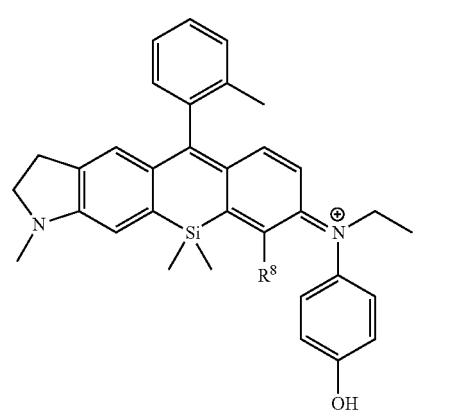

(I)

A compound represented by the general formulas (I), and (Ia) (including (Ia-1)-(Ia-3), and the same applies hereinafter)-(Ic) may be present as a salt. Examples of a salt include base addition salt, acid addition salt, and amino acid salt. Examples of the base addition salt include sodium salt, potassium salt, calcium salt, magnesium salt, and other metal salts, ammonium salt, or triethyl amine salt, piperidine salt, morpholine acid, and other organic amine salts. Examples of the acid addition salt include hydrochlorides, sulfates, nitrates, and other mineral acid salts; and methanesulfonic acid salt, p-toluenesulfonic acid salt, citrates, oxalates, and other organic acid salts. An example of the amino acid salt is glycine salt. As shall be apparent, salts of the compound of the present invention are not limited to the foregoing.

The compound of the present invention represented by general formulas (I) and (Ia)-(Ic) may have one or more asymmetric carbons in accordance with the substituent species, and an optical isomer, or diastereoisomer or other stereoisomer may be present. An unadulterated stereoisomer, any mixture of stereoisomers, racemates, and the like are also included in the scope of the present invention. The compound or salt thereof of the present invention represented by general formula (Ic) may also be present as a hydrate or solvate, and all of these substances are included in the scope of the present invention. The type of solvent that forms the solvate is not particularly limited; examples include ethanol, acetone, isopropanol, and other solvents.

Another mode of the present invention is a fluorescent probe comprising the compound represented by general formulas (I) and (Ia)-(Ic).

Measurement of the measured substance using the various fluorescent probes described above can be carried out in accordance with methods disclosed in the above-noted publications related to a monovalent substituent group cleaved by contact with a measured substance, as well as other methods known to persons skilled in the art. It is therefore possible to make application as a reagent for diagnosis for animals and humans in addition to use as a reagent for research. For example, the concentration and amount of a measured substance in a test tube can be measured using the various fluorescent probes described above, or incorporated into living cells or organisms, and then imaged and measured using bio-imaging techniques. Typical examples include a method comprising the following steps: (a) bringing a measured substance into contact with the compound or salt thereof represented by general formulas (I) and (Ia)-(Ic), which have a monovalent substituent group cleaved by contact with a measured substance; and (b) measuring the fluorescence intensity of the compound generated in step (a) after contact with the measured substance.

As described above, $R^{11}$, $R^9$, $R^{10}$, or $R^{13}$ can readily be used as a suitable substituent group in the compound of the present invention. It is apparent that a person skilled in the art could, for example, readily introduce a substituent group for labeling, a substituent group for obtaining a caged compound, or other functional substituent group other than a capturing group. The term "measure" as used in the present specification includes measuring, testing, detecting, and the like carried out for the purpose of quantification, qualification, diagnosis, or the like; and the broadest interpretation must be used.

Method for Synthesizing the Compound of the Present Invention

The compound of general formula (Ia) of the present invention can be synthesized in accordance with the following synthesis scheme (may also be referred to hereinafter as "synthesis method 1").

Scheme of synthesis method 1

[Chemical Formula 33]

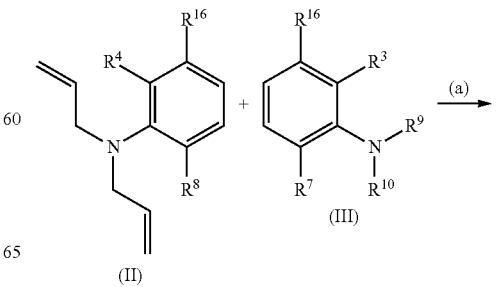

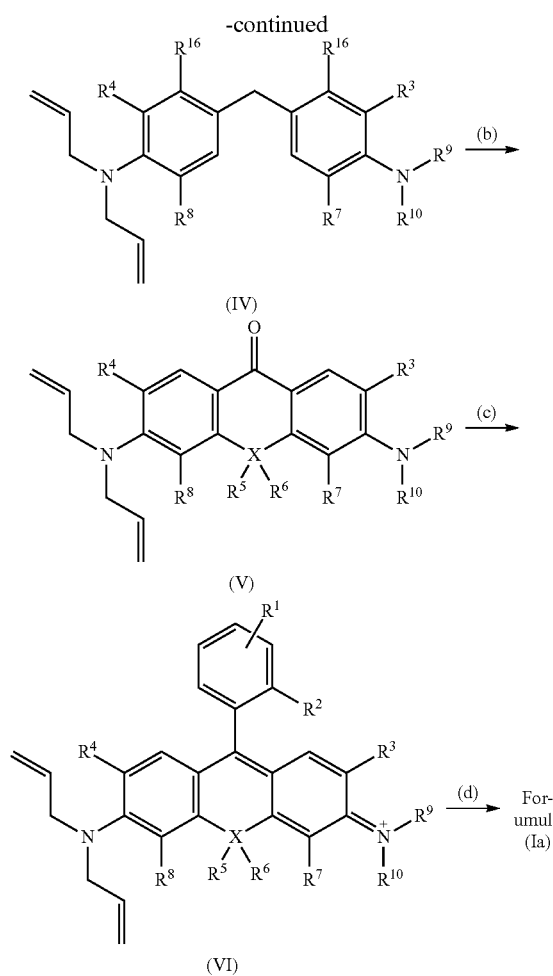

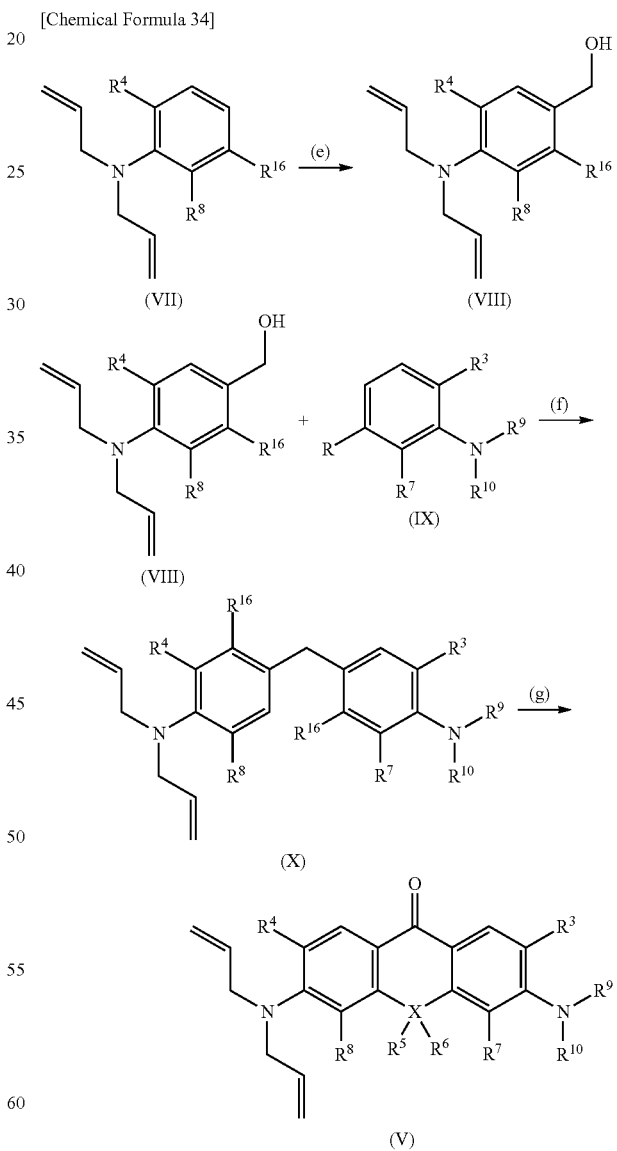

and thereafter treated with 50-to-200-eq 2N hydrochloric acid to thereby complete the synthesis of the compound represented by formula (VI).

(4) Step (d)

The compound represented by general formula (VI) is dissolved in methanol or the like, the system is then cooled to 0° C., and 3-to-5-eq sodium borohydride is added, and the system is treated with 2-to-10-eq 1,3-dimethylbarbituric acid to carry out deallylation. The deallylated compound is dissolved in a solvent, 2-to-5-eq chloranil is added and treatment carried out to obtain a compound in which $R^{11}$ and $R^{12}$ in general formula (Ia) are hydrogen atoms.

In the present invention, the compound of general formula (Ia) can be synthesized using the following synthesis scheme (may also be referred to hereinafter as "synthesis method 2").

Scheme of synthesis method 2

[Chemical Formula 34]

(1) Step (a)

3-halo-N,N-diallyl aniline represented by general formula (II) (where $R^{16}$ represents a halogen atom) is manufactured from 3-halogenated aniline and an allyl halide. The compound of formula (II) and the 3-halobenzene amine compound represented by formula (III) are dissolved in acetic acid or another acid, a formamide liquid is added, and the system is heated for 45 to 720 minutes at 25 to 80° C. to complete synthesis. The molar ratio of the compound of formula (II) and the compound of formula (III) is ordinarily 2:1-5:1.

(2) Step (b)

The compound represented by general formula (IV) is cooled to −78° C. in THF or the like, 2-to-100-eq sec-butyl lithium is then added, and 1.5-to-100-eq $X(Halo)_2(R^5)(R^6)$ (Halo is a chlorine atom or bromine atom; X, $R^5$, and $R^6$ are as defined above) is dissolved in a solvent in advance and added. The temperature is restored to room temperature and the system is allowed to react for about 1 to 2 hours. The residue after solvent removal is cooled to 0° C. in acetone or another solvent, 3-to-10-eq potassium permanganate is then added over about two hours, and the system is thereafter stirred for 1 to 5 hours at the same temperature to thereby synthesize the compound represented by formula (V).

(3) Step (c)

2-bromotoluene and THF or another solvent are mixed and cooled to −78° C., and 30-to-100-eq sec-butyl lithium is added. A compound of general formula (V) is dissolved in THF or another solvent, the resulting solution is added to the above mixture, the temperature is restored to room temperature, and the system is allowed to react about 1 to 2 hours (1) Step (e)

3-halo-N,N-diallyl aniline represented by general formula (VII) (where $R^{16}$ represents a halogen atom) is manufactured from 3-halogenated aniline and an allyl halide. 3-halo-N,N-diallyl aniline is dissolved in a solvent, 1-to-2-eq phosphorus oxychloride is added, 1-to-2-eq sodium hydroxide or another basic solution is added and the reaction was allowed to proceed. Next, 1-to-2-eq sodium borohydride is added and allowed to react to thereby synthesize a 3-halo-N,N-diallyl-4-hydroxymethylaniline represented by general formula (VIII).

(2) Step (f)

3-halo-N,N-diallyl-4-hydroxymethylaniline and a 3-halobenzene amine compound represented by formula (IX) are reacted in substantially equimolar amounts to synthesize the compound represented by general formula (X).

(3) Step (g)

The compound represented by general formula (X) is cooled to −78° C. in THF or another solvent, 5-to-100-eq sec-butyl lithium is added, and 5-to-100-eq $X(Halo)_2(R^5)(R^6)$ (Halo is a chlorine atom or bromine atom; X, $R^5$, and $R^6$ are as defined above) is dissolved in a solvent in advance and added. The temperature is restored to room temperature and the system is allowed to react for about 1 to 2 hours. The residue after solvent removal is cooled to 0° C. in acetone or another solvent, 3-to-10-eq potassium permanganate is then added over about two hours, and the system is thereafter stirred for 1 to 5 hours at the same temperature to thereby synthesize the compound represented by formula (V).

The method for obtaining the compound of general formula (Ia) from general formula (V) is the same as the method of scheme 1.

A monovalent substituent group cleaved by contact with a measured substance can be introduced as $R^{11}$ by using a conventionally known method (by, e.g., adding 1-to-2-eq amino acid or peptide recognizable and cleavable by a measured substance, 1-to-2-eq HATU or other condensing agent, and 2-to-4-eq DIPEA, pyridine or other base devoid of nucleophilicity to the compound of Ia dissolved in a solvent).

An alkyl group can be introduced as $R^{12}$ for a compound obtained by synthesis method 1 or synthesis method 2 in which $R^{11}$ and $R^{12}$ are hydrogen atoms in general formula (Ia) using, e.g., a method in which amidation is performed using 2-to-5-eq acid chloride, the amide is reduced by hydride reduction using a 100-to-150-eq borane-tetrahydrofuran complex or the like and then oxidation is carried out using 2-to-5 equivalent chloranil or the like; or a method in which hydride reduction of 2-to-10-eq sodium tetrahydroborate or the like is carried out, methylation is then carried out using 10-to-20-eq paraformaldehyde and 10-to-20-eq sodium tetrahydroborate, after which an SN2 reaction is carried out using 1-to-1.5-eq alkyl bromide or the like, and then oxidation is carried out using 2-to-5-eq chloranil or the like.

The compound of general formula (Ib) of the present invention can be synthesized in accordance with the following synthesis scheme.

Synthesis scheme

[Chemical Formula 35]

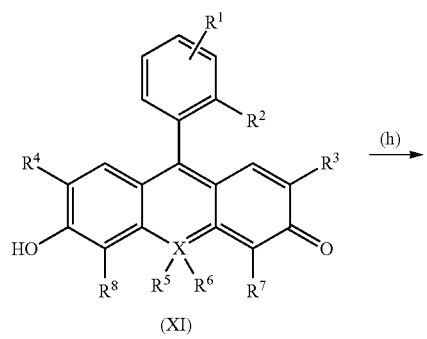

(XI)

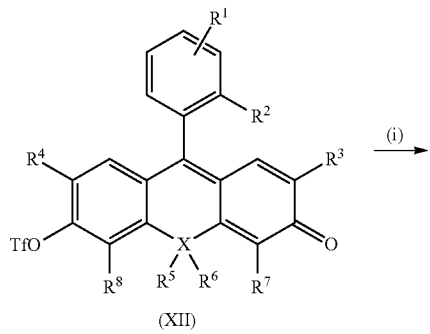

(XII)

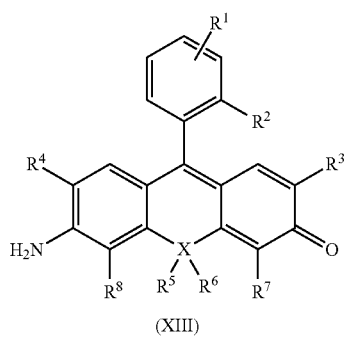

(XIII)

(1) Step (h)

The compound represented by general formula (XI) is dissolved in a solvent, pyridine or another base is added, and the system is reacted with 1-to-2 equivalent trifluoromethanesulfonic anhydride ($Tf_2O$) to complete the synthesis of the compound represented by general formula (XII).

(2) Step (i)

The compound represented by general formula (XII) is dissolved in a solvent, a catalytic amount of $Pd_2(dba)_2 \cdot CHCl_2$, a catalytic amount of xantphos, 1-to-1.5 equivalent $Cs_2CO_3$, and 1-to-1.5 equivalent benzophenone imine or other imine compound are added, hydrolysis is carried out using a dilute acid to complete the synthesis of the compound represented by general formula (XIII). The compound represented by general formula (XIII) is a keto unit of a compound of which $R^{13}$ is a hydrogen atom in general formula (1b).

An alkyl group can be introduced to an amino group and a carbonyl group can be converted to an alkoxyl group by reacting the compound represented by general formula (XIII) with an alkyl halide.

A fluorescent probe can be obtained by reacting the compound represented by general formula (XII), an amide compound (acetoamide or the like), and a peptide (the carboxylic acid at the C terminal is $CONH_2$) or the like taken from a resin for peptide synthesis, whereby a monovalent substituent group cleaved by contact with an amide group or other measured substance is introduced to the xanthene ring site.

The compound of general formula (Ia-3) of the present invention can be synthesized in accordance with the following synthesis scheme.

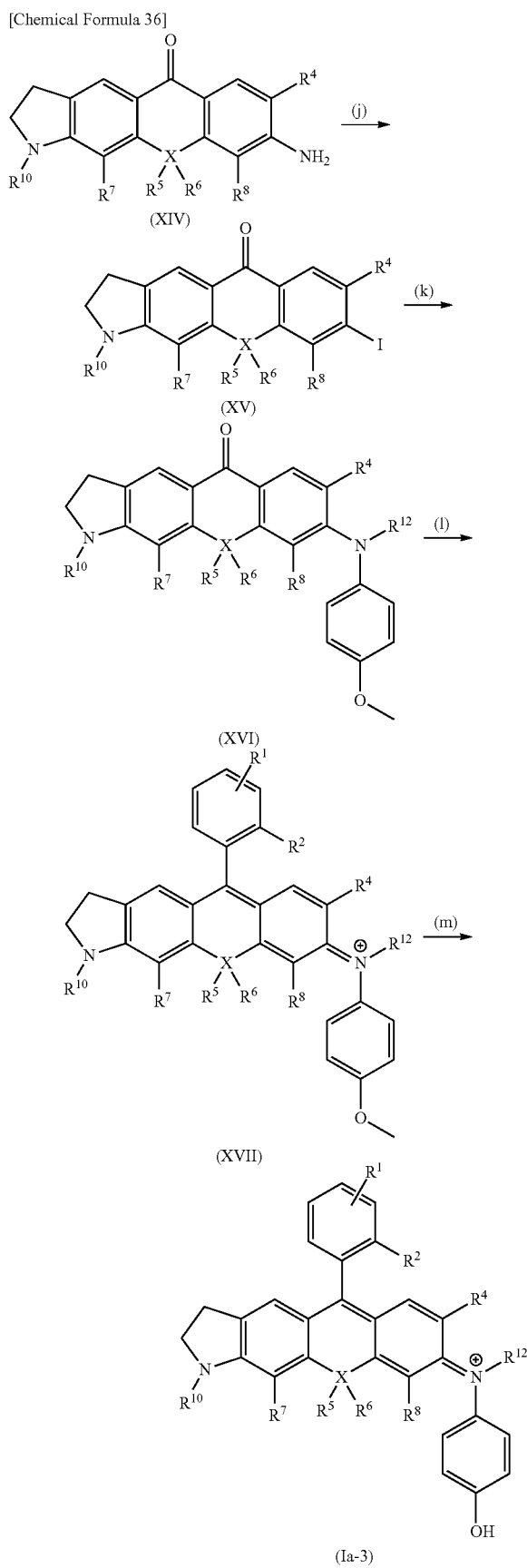

(1) Step (j)

The compound represented by general formula (XIV) is dissolved in a mixed solvent composed of an organic solvent and hydrochloric acid or other acidic aqueous solution, the system is then cooled to about 0° C., 1-to-2 equivalent $NaNO_2$ aqueous solution is dropped, and the system is stirred for a predetermined length of time, after which 1-to-10 equivalent aqueous solution of potassium iodide is added and allowed to react to thereby synthesize the compound of general formula (XV).

(2) Step (k)

The compound of formula (XV) and N-alkyl-p-anisidine in which the alkyl group has 1-6 carbons are dissolved in toluene or another organic solvent, and $Pd(OAc)_2$ and BINAP are added and allowed to react to thereby synthesize the compound represented by general formula (XVI).

(3) Step (l)

The compound represented by general formula (XVI) is dissolved in THF or another solvent, and 1-to-50 equivalent o-tolylmagnesium bromide is added and allowed to react, after which an acid is added to synthesize the compound represented by general formula (XVII).

(4) Step (m)

The compound represented by general formula (XVII) is dissolved in a solvent, 1-to-3 equivalent boron tribromide is added and allowed to react to thereby synthesize the compound represented by general formula (Ia-3).

The compound of general formula (Ic) of the present invention can be synthesized by dissolving the compound obtained in synthesis method 1 or 2, of which $R^{11}$ and $R^{12}$ are hydrogen atoms in general formula (Ia), in a mixed solvent composed of 1:1 $MeCN/CH_2CL_2$ containing TFA, and reacting the system with, e.g., N,N-dialkyl aniline at a temperature of about 0° C. in the presence of sodium nitrite.

The method for using the fluorescent probe of the present invention is not particularly limited; examples include: measurement of isolated and purified enzymes, and observed enzyme activity contained in a cell lysate; measurement of enzyme activity in a living cell; and measurement of activity of enzymes acting as cancer biomarkers in biological tissue which make use of optical characteristics such as long wavelengths.

A fluorescent probe containing the compound represented by general formula (Ia-3) of the present invention can be advantageously used for measuring active-oxygen species, e.g., $H_2O_2$, $^-OCl$, $ONOO^-$, $O_2^-$, and hydroxyl radicals.

A fluorescent probe containing the compound represented by general formula (Ic) of the present invention can be advantageously used for detecting a low-oxygen environment.

EXAMPLES

The present invention is described in more detail below using examples, but the scope of the present invention is not limited by the examples described below. In the examples, Me refers to a methyl group and Ac refers to an acetyl group.

Example 1

Compounds 1 and 2 of the present invention were synthesized using the following synthesis schemes.

Scheme 1

[Chemical Formula 37]

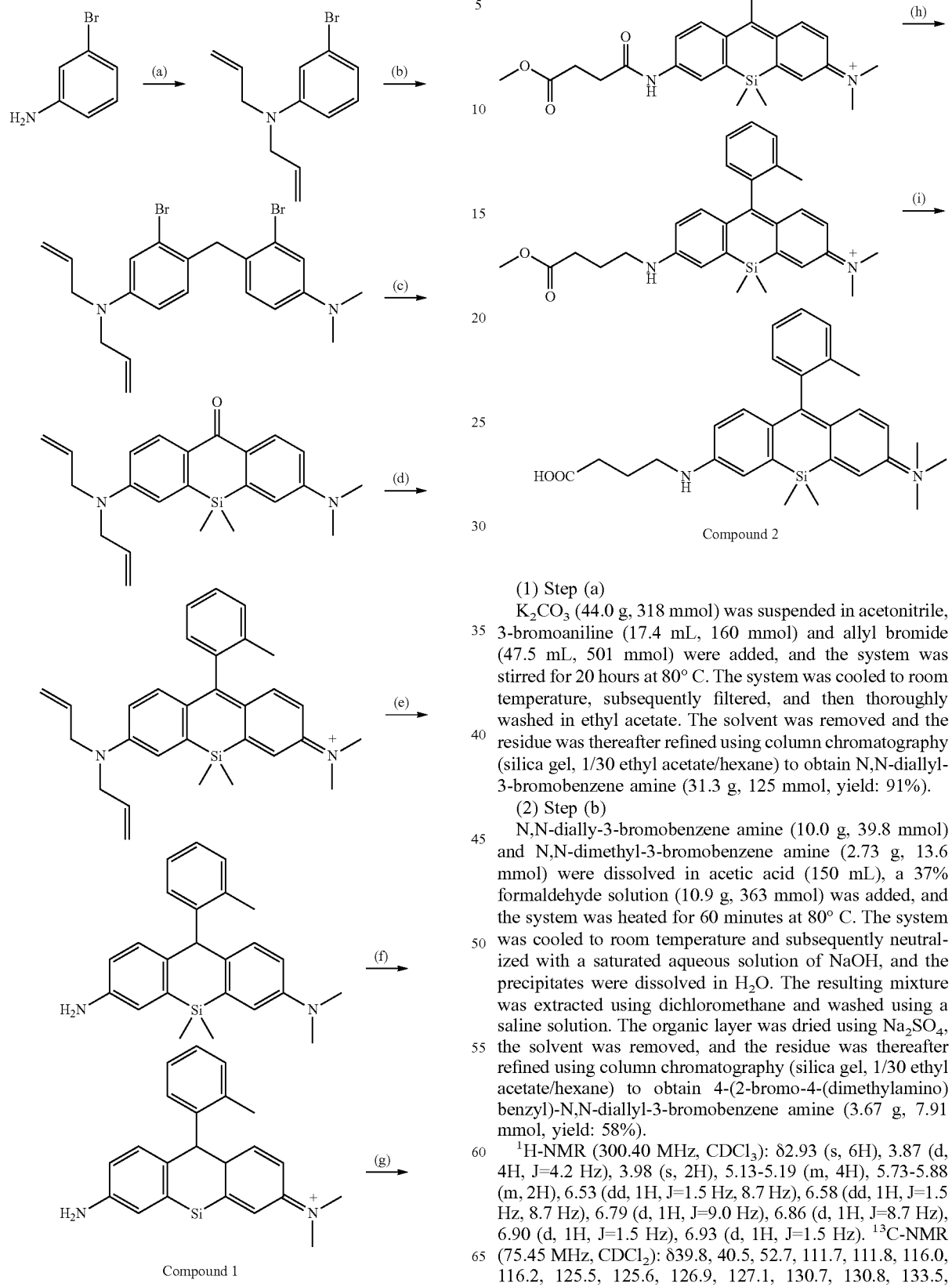

Compound 1

Compound 2

(1) Step (a)

K$_2$CO$_3$ (44.0 g, 318 mmol) was suspended in acetonitrile, 3-bromoaniline (17.4 mL, 160 mmol) and allyl bromide (47.5 mL, 501 mmol) were added, and the system was stirred for 20 hours at 80° C. The system was cooled to room temperature, subsequently filtered, and then thoroughly washed in ethyl acetate. The solvent was removed and the residue was thereafter refined using column chromatography (silica gel, 1/30 ethyl acetate/hexane) to obtain N,N-diallyl-3-bromobenzene amine (31.3 g, 125 mmol, yield: 91%).

(2) Step (b)

N,N-dially-3-bromobenzene amine (10.0 g, 39.8 mmol) and N,N-dimethyl-3-bromobenzene amine (2.73 g, 13.6 mmol) were dissolved in acetic acid (150 mL), a 37% formaldehyde solution (10.9 g, 363 mmol) was added, and the system was heated for 60 minutes at 80° C. The system was cooled to room temperature and subsequently neutralized with a saturated aqueous solution of NaOH, and the precipitates were dissolved in H$_2$O. The resulting mixture was extracted using dichloromethane and washed using a saline solution. The organic layer was dried using Na$_2$SO$_4$, the solvent was removed, and the residue was thereafter refined using column chromatography (silica gel, 1/30 ethyl acetate/hexane) to obtain 4-(2-bromo-4-(dimethylamino) benzyl)-N,N-diallyl-3-bromobenzene amine (3.67 g, 7.91 mmol, yield: 58%).

$^1$H-NMR (300.40 MHz, CDCl$_3$): δ2.93 (s, 6H), 3.87 (d, 4H, J=4.2 Hz), 3.98 (s, 2H), 5.13-5.19 (m, 4H), 5.73-5.88 (m, 2H), 6.53 (dd, 1H, J=1.5 Hz, 8.7 Hz), 6.58 (dd, 1H, J=1.5 Hz, 8.7 Hz), 6.79 (d, 1H, J=9.0 Hz), 6.86 (d, 1H, J=8.7 Hz), 6.90 (d, 1H, J=1.5 Hz), 6.93 (d, 1H, J=1.5 Hz). $^{13}$C-NMR (75.45 MHz, CDCl$_2$): δ39.8, 40.5, 52.7, 111.7, 111.8, 116.0, 116.2, 125.5, 125.6, 126.9, 127.1, 130.7, 130.8, 133.5, 148.1, 150.0LRMS (ESI+): 465 for [M+H]$^+$ (3) Step (c)

4-(2-bromo-4-(dimethylamino)benzyl)-N,N-diallyl-3-bromobenzene amine (19.9 g, 43.0 mmol) and anhydrous tetrahydrofuran (THF, 120 mL) were added to a dry, argon-substituted flask. The system was cooled to −78° C., 1M sec-butyl lithium (120 mL, 120 mmol) was added, and the system was stirred for 20 minutes. Dimethylsilyldichloride (5.8 mL, 60 mmol) was dissolved in 40 mL of anhydrous THF and slowly added with the temperature unchanged. The system was restored to room temperature and stirred for one hour. The reaction was stopped using 2N hydrochloric acid and the system was neutralized using $NaHCO_3$. The resulting mixture was extracted using dichloromethane and washed using a saline solution. The organic layer was dried using $Na_2SO_4$, and the solvent was subsequently removed. The residue was dissolved in acetone (300 mL) and cooled to 0° C., $KMnO_4$ (19.4 g, 123 mmol) was added in small amounts over two hours, and the system was further stirred for one hour at the same temperature. The system was washed using dichloromethane while being suction-filtered using a filter paper. The solvent was removed and the residue was refined using column chromatography (silica gel, dichloromethane) to obtain N,N-diallyl-N',N'-dimethyl-diamino-Si-xanthone (4.68 g, 12.4 mmol, yield: 29%).

$^1$H-NMR (300.40 MHz, $CDCl_3$): δ 0.44 (s, 6H), 3.09 (s, 6H), 4.03 (d, 4H, J=4.4 Hz), 5.18-5.30 (m, 4H), 5.82-5.95 (m, 2H), 6.78-6.85 (m, 4H), 8.36 (d, 1H, J=8.7 Hz), 8.39 (d, 1H, J=9.0 Hz) $^{13}$C-NMR (75.45 MHz, $CDCl_3$): δ−1.1, 40.0, 52.6, 113.1, 113.4, 114.2, 114.7, 116.5, 129.6, 129.9, 131.6, 133.0, 140.4, 150.1, 151.4, 185.1HRMS (ESI+): Found: 377.2019, calculated 377.2049 for $[M+H]^+$ (−3.0 mmu).

(4) Step (d)

2-bromotoluene (14 mL, 110 mmol) and anhydrous tetrahydrofuran (THF, 50 mL) were added to a well dried, argon-substituted flask. The system was cooled to −78° C., 1M sec-butyl lithium (100 mL, 100 mmol) was added, and the system was stirred for 20 minutes. N,N-diallylamino-N',N'-dimethylamino-Si-xanthone (930 mg, 2.47 mmol) was dissolved in 30 mL of anhydrous THF and slowly added with the temperature unchanged. The temperature was restored to room temperature and the system was stirred for one hour at room temperature, after which 80 mL of 2N hydrochloric acid was added and the system was stirred for 20 minutes. The resulting mixture was extracted using dichloromethane and washed using a saline solution. The organic layer was dried using $Na_2SO_4$, and the solvent was removed. The residue was refined using column chromatography (silica gel, 1/19→1/4 methanol/dichloromethane) to obtain N-[7-(diallylamino)-9,9-dimethyl-10-(2-methylphenyl)-9-silaanthracen-2 (9H)-ylidene]-N-methyl-methane aminium (1.07 g, 2.20 mmol, yield: 89%).

$^1$H-NMR (300.40 MHz, $CDCl_3$): δ0.61 (s, 3H), 0.63 (s, 3H), 2.04 (s, 3H), 3.49 (s, 6H), 4.21 (d, 4H, J=5.1 Hz), 5.19-5.32 (m, 4H), 5.82-5.95 (m, 2H), 6.11 (dd, 1H, J=1.5 Hz, 9.6 Hz), 6.69 (dd, 1H, J=1.5 Hz, 10.2 Hz), 7.07 (d, 1H, J=9.6 Hz), 7.11-7.14 (m, 2H), 7.29 (d, 1H, J=3.0 Hz), 7.35-7.49 (m, 4H)

$^{13}$C-NMR (100.40 MHz, $CDCl_3$): δ−1.1, −0.8, 19.4, 41.6, 53.6, 114.0, 114.5, 118.1, 120.6, 121.7, 125.6, 127.6, 128.0, 128.8, 128.9, 130.2, 130.4, 130.8, 135.6, 138.3, 141.0, 142.2, 147.7, 153.2, 154.7, 170.0

HRMS (ESI+): Found: 451.2541, calculated 451.2569 for $[M]^+$ (−2.8 mmu).

(5) Step (e)

N-[7-(diallylamino)-9,9-dimethyl-10-(2-methylphenyl)-9-silaanthracen-2(9H)-ylidene]-N-methyl-methane ammonium (1.15 g, 2.36 mmol) was dissolved in methanol (100 mL). The system was cooled to 0° C., sodium borohydride (367 mg, 9.72 mmol) was added, and the system was stirred for 30 minutes. The reaction solution was removed with shaking using a saturated aqueous solution of $NaHCO_3$, the resultant was then washed with a saline solution, and the organic layer was dried using $Na_2SO_4$, after which the solvent was removed. The residue was partially refined using column chromatography (silica gel, 1/4 ethyl acetate/hexane) to obtain a 7-diallylamino-2-dimethylamino-10-(2-methylphenyl)-9,10-dihydro-9,9-dimethyl-9-silaanthracene mixture (785 mg). $Pd(PPh_3)_4$ (213 mg, 0.184 mmol) and 1,3-dimethylbarbituric acid (943 mg, 6.04 mmol) were added to a dried, argon-substituted flask. The mixture obtained earlier was dissolved in 50 mL of dichloromethane and added to the system, and the system was heated and stirred for 11 hours at 35° C. The solvent was removed, and the system was suspended in a saturated aqueous solution of $NaHCO_3$ and extracted using dichloromethane. The organic layer was dried using $Na_2SO_4$, the solvent was removed, and the residue was thereafter refined using column chromatography (silica gel, 1/9→1/4 ethyl acetate/hexane) to obtain 7-amino-2-dimethylamino-10-(2-methylphenyl)-9,10-dihydro-9,9-dimethyl-9-silaanthracen (450 mg, 1.21 mmol, yield: 51%).

$^1$H-NMR (300.40 MHz, $CD_3OD$): δ0.37 (s, 3H), 0.54 (s, 3H), 2.17 (s, 3H), 2.88 (s, 6H), 5.50 (s, 1H), 6.60 (dd, J=8.4 Hz, 2.6 Hz, 1H), 6.69 (dd, J=8.8 Hz, 2.9 Hz, 1H), 6.78 (d, J=8.8 Hz, 1H), 6.86 (d, J=8.7 Hz, 1H), 6.97-7.09 (m, 6H) $^{13}$C-NMR (75.45 MHz, $CDCl_3$): δ−1.0, −0.3, 20.5, 40.7, 49.9, 114.6, 116.3, 116.9, 119.0, 125.8, 126.1, 129.8, 130.1, 131.0, 131.1, 133.6, 134.4, 135.5, 137.2, 139.2, 143.3, 146.0, 147.9HRMS (ESI+): Found: 373.2071, calculated 373.2100 for $[M+H]^+$ (−2.9 mmu).

(6) Step (f): Synthesis of 2-MeSiR620 (Compound 1)

7-amino-2-dimethylamino-10-(2-methylphenyl)-9,10-dihydro-9,9-dimethyl-9-silaanthracene (121 mg, 0.324 mmol) and chloranil (159 mg, 0.647 mmol) were dissolved in dicholomethane (10 mL), and the system was stirred for 30 minutes at room temperature. The solvent was removed and 2-MeSiR620 trifluoroacetate (Compound 1) (103 mg, 0.213 mmol, yield: 66%) was obtained by high-performance liquid chromatography (HPLC).

$^1$H-NMR (300.40 MHz, $CD_3OD$): δ0.55 (s, 3H), 0.56 (s, 3H), 2.04 (s, 3H), 3.34 (s, 6H), 6.58 (dd, 1H, J=2.1 Hz, 9.6 Hz), 6.76 (dd, 1H, J=3.0 Hz, 9.6 Hz), 7.02 (d, 1H, 9.6 Hz), 7.07-7.13 (m, 2H), 7.20 (d, 1H, J=2.1 Hz), 7.36-7.49 (m, 4H) $^{13}$C-NMR (75.45 MHz, $CDCl_3$): δ−1.6, −1.3, 19.3, 40.4, 113.1, 117.5, 119.3, 125.5, 125.5, 127.4, 127.8, 128.7, 128.9, 130.1, 135.6, 138.6, 140.2, 143.5, 146.9, 150.1, 153.0, 158.1, 169.1HRMS (ESI+): Found: 371.1974, calculated 371.1944 for $[M]^+$ (3.1 mmu).

(7) Step (g)

2-MeSiR620 trifluoroacetate (103 mg, 0.213 mmol), diisopropylethyl amine (140 μL, 0.823 mmol), and anhydrous tetrahydrofuran (17 mL) were added to a dried flask. The system was cooled to 0° C., methyl 4-chloro-4-oxobutyrate (100 μL, 0.812 mmol) was added, argon substitution was performed, and the system was stirred for five hours at room temperature. The solvent was removed, the residue was refined by HPLC to obtain methyl 4-oxo-4-(2-MeSiR620)-butyrate trifluoroacetate (86.4 mg, 0.144 mmol, yield: 68%).

$^1$H-NMR (300.40 MHz, $CDCl_3$): δ0.55 (s, 3H), 0.57 (s, 3H), 2.00 (s, 3H), 2.66 (t, 2H, J=6.6 Hz), 2.95 (t, 2H, J=6.6 Hz), 3.44 (s, 3H), 3.59 (s, 3H), 3.66 (s, 3H), 6.72-6.75 (m, 1H), 7.07 (d, 1H, J=7.5 Hz), 7.12 (d, 1H, J=9.0 Hz) 7.30-7.36 (m, 4H), 7.42-7.47 (m, 1H), 7.97 (dd, 1H, J=2.1

Hz, 8.7 Hz), 8.29 (d, 1H, J=2.1 Hz), 11.28 (s, 1H) $^{13}$C-NMR (100.40 MHz, CDCl$_3$): δ −1.8, −1.4, 19.5, 28.8, 31.9, 41.6, 41.9, 51.7, 115.6, 121.1, 122.8, 125.6, 128.8, 129.3, 130.4, 133.3, 135.6, 137.8, 140.2, 144.6, 144.8, 146.3, 154.3, 156.1, 172.6, 173.1HRMS (ESI+): Found: 485.2242, calculated 485.2260 for [M]+ (−1.8 mmu).

(8) Step (h)

Methyl 4-oxo-4-(2-MeSiR620)-butyrate trifluoroacetate (20.7 mg, 0.0346 mmol) and anhydrous tetrahydrofuran (8 mL) were added to a well dried, argon-substituted flask. The system was cooled to 0° C., a 0.9M borane-tetrahydrofuran complex (5 mL, 4.5 mmoL) was added, and the system was restored to room temperature. The system was stirred for 270 minutes at room temperature, and the reaction was stopped by slow addition of an aqueous solution of 0.1% trifluoroacetic acid (20 mL). The tetrahydrofuran was removed from the mixture, the resultant was then extracted with dichloromethane and washed in a saline solution, the organic layer was dried using Na$_2$SO$_4$, and the solvent was then removed. The residue was dissolved in dichloromethane (4 mL), chloranil (4 mg) was added, and the system was stirred at room temperature for 15 minutes. The solvent was removed and the resulting residue was refined by HPLC to obtain methyl 4-(2-MeSiR620)-butyrate trifluoroacetate (8.1 mg, 0.014 mmol, yield: 40%).

$^1$H-NMR (300.40 MHz, CDCl$_3$): δ 0.54 (s, 3H), 0.56 (s, 3H), 1.99-2.06 (m, 5H), 2.46 (t, 2H, J=6.2 Hz), 3.25 (s, 6H), 3.51 (br, 2H), 3.67 (s, 3H), 6.54 (dd, 1H, J=3.0 Hz, 9.0 Hz), 6.65 (br, 1H), 7.01 (d, 1H, J=9.6 Hz), 7.03 (d, 1H, J=3.0 Hz), 7.07 (d, 2H, J=7.2 Hz), 7.30-7.44 (m, 4H), 9.98 (br, 1H) $^{13}$C-NMR (75.45 MHz, CDCl$_3$): δ−1.5, −1.2, 19.3, 23.8, 30.6, 40.3, 42.6, 51.7, 113.0, 119.2, 125.6, 127.5, 127.8, 128.7, 128.9, 130.2, 135.7, 138.6, 139.6, 152.8, 156.4, 168.6, 173.6HRMS (ESI+): Found: 471.2477, calculated 471.2468 for [M]+ (0.9 mmu).

(9) Step (i): Synthesis of 2-MeSiR620-a1 (Compound 2)

Methyl 4-(2-MeSiR620)-butyrate trifluoroacetate (37.4 mg, 0.0640 mmol) was dissolved in a mixture of methanol (30 mL) and an aqueous solution of 2N sodium hydroxide (30 mL), and the system was heated and stirred for 270 minutes at 40° C. The system was neutralized using 2N hydrochloric acid, thereafter extracted using dichloromethane, and washed using a saline solution. The solvent was removed, and the residue was then refined by HPLC to obtain 2-MeSiR620-a1 trifluoroacetate (Compound 2) (20.2 mg, 0.0354 mmol, yield: 55%).

$^1$H-NMR (300.40 MHz, CDCl$_3$): δ0.54 (s, 3H), 0.56 (s, 3H), 2.03 (m, 5H), 2.60 (br, 2H), 3.26 (s, 6H), 3.49 (br, 2H), 6.54 (dd, 2H, J=3.0 Hz, 9.0 Hz), 7.00-7.08 (m, 4H), 7.29-7.44 (m, 4H), 9.47 (br, 1H)HRMS (ESI+): Found: 457.2278, calculated 457.2311 for [M]+ (−3.3 mmu).

Figure 1B:
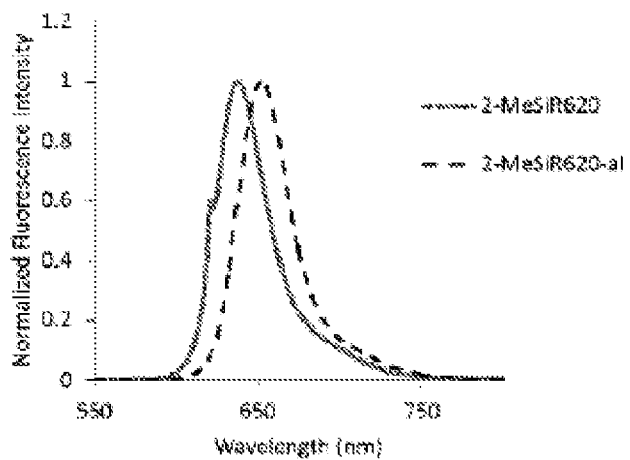
FIG. 1b Result of measuring fluorescence profile of 2-MeSiR620 (Compound 1) and 2-MeSiR620-a1 (Compound 2).

Absorbance and fluorescence profiles of 2-MeSiR620 (Compound 1) obtained in step (f) and 2-MeSiR620-a1 (Compound 2) obtained in step (i) were measured. The results are shown in FIGS. 1a and 1b. Measurements were carried out in an aqueous solution of 0.1M sodium phosphate having a pH 7.4 and containing 0.1% DMSO. The wavelength of the excitation light in the fluorescence profile measurement was 620 nm for 2-MeSiR620 and 635 nm for 2-MeSiR620-a1.

The optical characteristic data of 2-MeSiR620 and 2-MeSiR620-a1 is summarized in Table 1. Abs$_{max}$ and Em$_{max}{}^a$ both show that binding alkyl linkers together increases the wavelength and the molar absorbance coefficient and elevates fluorescence quantum yield.

TABLE 1

|  | Abs$_{max}{}^a$ (nm) | $\epsilon^a$ (M$^{-1}$cm$^{-1}$) | Em$_{max}{}^a$ (nm) | $\Phi_{fl}{}^{ab}$ |
|---|---|---|---|---|
| Compound 1 | 620 | 96,000 | 638 | 0.21 |
| Compound 2 | 635 | 130,000 | 651 | 0.31 |

$^a$Measurement carried out in pH 7.4 sodium phosphate buffer solution
$^b$Cresyl violet in methanol ($\Phi_{fl}$ = 0.54) was used as the fluorescence reference Example 2

Compound 3 of the present invention was synthesized using the following synthesis scheme.

Scheme 2

[Chemical Formula 38]

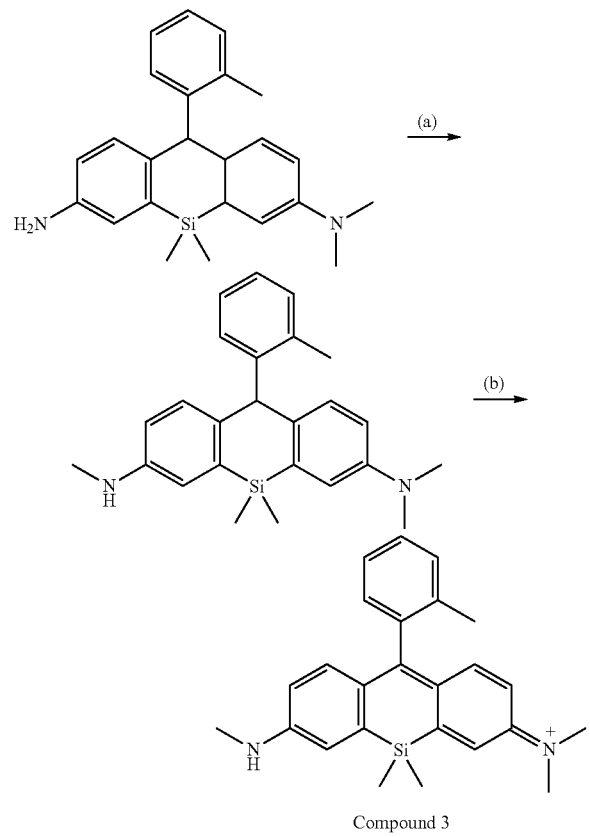

Compound 3

(1) Step (a)

7-amino-2-dimethylamino-10-(2-methylphenyl)-9,10-dihydro-9,9-dimethyl-9-silaanthracene (243 mg, 0.653 mmol), sodium methoxide (245 mg, 4.53 mmol), and paraformaldehyde (266 mg, 8.87 mmol) were added to methanol (10 mL), the suspension was stirred for 15 hours at room temperature, sodium borohydride (410 mg, 10.8 mmol) was then added, and the system was stirred for 2 hours at 80° C. An aqueous solution of 1N sodium hydroxide was added to the reaction solution, and the resultant was thereafter extracted using dichloromethane and washed using a saline solution. The organic layer was dried using Na$_2$SO$_4$, the solvent was removed, and refining was carried out by column chromatography (silica gel, 1/4 ethyl acetate/hexane) to obtain 7-methylamino-2-dimethylamino-10-(2-methylphenyl)-9,10-dihydro-9,9-dimethyl-9-silaanthracene (171.7 mg, 0.444 mmol, yield: 68%).

$^1$H-NMR (300.40 MHz, CD$_3$OD): δ 0.38 (s, 3H), 0.55 (s, 3H), 2.17 (s, 3H), 2.75 (s, 3H), 2.88 (s, 6H), 5.51 (s, 1H), 6.53 (dd, J=8.4 Hz, 2.6 Hz, 1H), 6.68 (dd, J=8.8 Hz, 2.9 Hz, 1H), 6.80 (d, J=8.1 Hz, 1H), 6.85-6.87 (m, 2H), 6.98-7.08 (m, 5H) $^{13}$C-NMR (75.45 MHz, CDCl$_3$): δ −0.9, −0.3, 20.5, 30.8, 40.7, 49.8, 114.3, 114.6, 116.1, 116.3, 125.7, 126.1, 129.8, 130.0, 131.0, 131.2, 133.8, 134.1, 135.5, 137.3, 137.9, 146.1, 146.4, 147.9 HRMS (ESI+): Found: 387.2221, Calculated 387.2257 for [M+H]$^+$ (−3.6 mmu).

(2) Step (b): Synthesis of 2-MeSiR630 (Compound 3)

7-methylamino-2-dimethylamino-10-(2-methylphenyl)-9,10-dihydro-9,9-dimethyl-9-silaanthracene (18.4 mg, 0.048 mmol) was dissolved in dichloromethane (2 mL), chloranil (32.0 mg, 0.130 mmol) was added, and the system was stirred for 1 hour at room temperature. The solvent was removed and the residue was refined by HPLC to obtain 2-MeSiR630 trifluoroacetate (Compound 3) (4.8 mg, 9.63 µmol, yield: 20%).

$^1$H-NMR (300.40 MHz, CDCl$_3$): δ 0.54 (s, 3H), 0.56 (s, 3H), 2.03 (s, 3H), 3.12 (s, 3H), 3.23 (s, 6H), 6.53 (dd, J=3.0 Hz, 6.6 Hz, 1H), 6.91-7.09 (m, 4H), 7.30-7.44 (m, 5H)HRMS (ESI+): Found: 385.2107, Calculated 385.2100 for [M]$^+$ (0.7 mmu).

Compound 4 of the present invention was synthesized using the following synthesis scheme.

Scheme 3

[Chemical Formula 39]

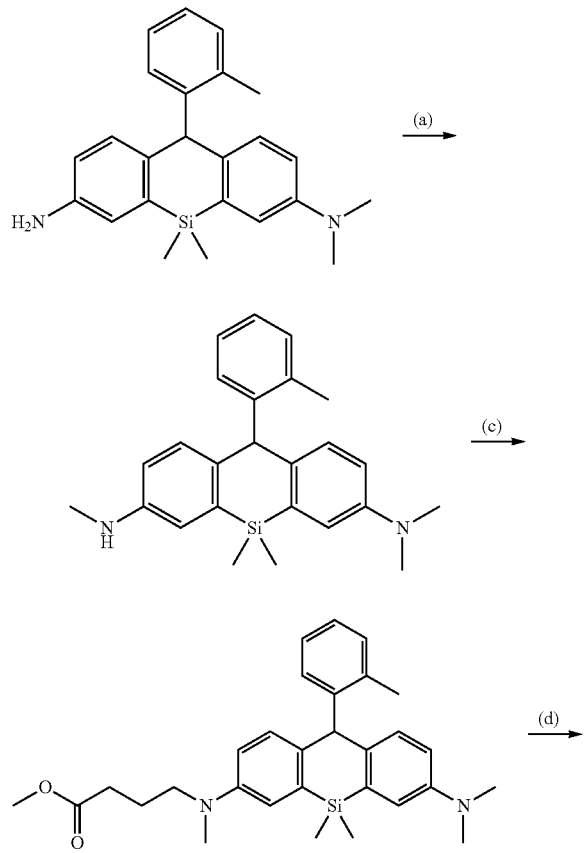

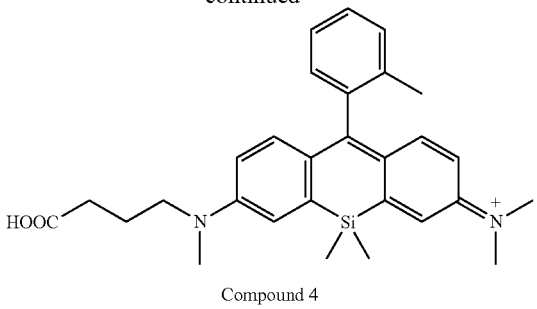

Compound 4

(3) Step (c)

7-methylamino-2-dimethylamino-10-(2-methylphenyl)-9,10-dihydro-9,9-dimethyl-9-silaanthracene (95.3 mg, 0.247 mmol), K$_2$CO$_3$ (78.2 mg, 0.566 mmol), potassium iodide (50.0 mg, 0.301 mmol), methyl 4-bromobutyrate (50 µL, 0.397 mmol), and anhydrous acetonitrile (10 mL) were added to a well dried, argon-substituted flask, and the system was stirred for 2 days at 100° C. The reaction solution was cooled to room temperature, and thereafter filtered and thoroughly washed using ethyl acetate. The solvent was removed from the filtrate and the residue was refined using column chromatography (silica gel, 1/4 hexane/dichloromethane→dichloromethane) to obtain methyl 4-(2-dimethylamino-10-(2-methylphenyl)-9,10-dihydro-9,9-dimethyl-9-sila-7-anthracenyl)methylaminobutyrate (40.4 mg, 0.083 mmol, yield: 34%).

$^1$H-NMR (300.40 MHz, CDCl$_3$): δ 0.44 (s, 3H), 0.60 (s, 3H), 1.85-1.95 (m, 2H), 2.24 (s, 3H), 2.35 (t, 2H, J=7.0 Hz), 2.91 (s, 3H), 2.93 (s, 6H), 3.33 (t, 2H, J=7.3 Hz), 3.65 (s, 3H), 5.56 (s, 1H), 6.59-6.67 (m, 2H), 6.87 (dd, 2H, J=8.8 Hz, 4.4 Hz), 6.92 (dd, 2H, J=9.9 Hz, 2.6 Hz), 7.03-7.14 (m, 4H). $^{13}$C-NMR (75.45 MHz, CDCl$_3$): δ −0.9, −0.3, 20.5, 22.3, 31.3, 38.3, 40.7, 49.7, 51.6, 52.0, 114.2, 114.6, 115.9, 116.4, 125.7, 126.1, 129.8, 129.9, 131.0, 131.2, 133.9, 134.0, 135.6, 137.0, 137.4, 146.1, 146.6, 147.9, 173.7. HRMS (ESI+): Found: 487.2759. Calculated 487.2781 for [M+H]$^+$ (−2.2 mmu).

(4) Step (d)

Methyl 4-(2-dimethylamino-10-(2-methylphenyl)-9,10-dihydro-9,9-dimethyl-9-sila-7-anthracenyl)methylaminobutyrate (30.3 mg, 0.062 mmol) was dissolved in a mixed solution composed of methanol (20 mL) and 2N sodium hydroxide aqueous solution (20 mL), and the system was heated and stirred for 4 hours at 40° C. The system was neutralized using 2N hydrochloric acid, and the resultant was thereafter extracted using dichloromethane and washed using a saline solution. The solvent was removed, the residue was then dissolved in dichloromethane (5 mL), chloranil (29.6 mg, 0.120 mmol) was added, and the system was stirred for 100 minutes at room temperature. The solvent was removed and the residue was refined by HPLC to obtain 2-MeSiR630-a1 trifluoroacetate (Compound 4) (17.8 mg, 0.030 mmol, yield: 49%).

$^1$H-NMR (300.40 MHz, CDCl$_3$): δ 0.62 (s, 3H), 0.64 (s, 3H), 2.04 (m, 5H), 2.66 (br, 2H), 3.30 (m, 9H), 3.80 (br, 2H), 6.57 (dd, J=3.0 Hz, 6.6 Hz, 1H), 7.06-7.12 (m, 6H), 7.31-7.43 (m, 3H) $^{13}$C-NMR (100.40 MHz, CDCl$_3$): δ −1.4, −1.1, 19.4, 22.4, 30.5, 39.1, 40.7, 52.7, 113.5, 114.0, 120.2, 125.6, 127.7, 127.7, 128.9, 128.9, 130.3, 135.7, 138.4, 141.3, 142.3, 149.5, 153.8, 154.2, 170.6HRMS (ESI+): Found: 471.2425. Calculated 471.2468 for [M]$^+$ (−4.3 mmu).

The absorbance and fluorescence spectra of 2-MeSiR630 (Compound 3) synthesized in step (b) and 2-MeSiR630-a1

Figure 2A:
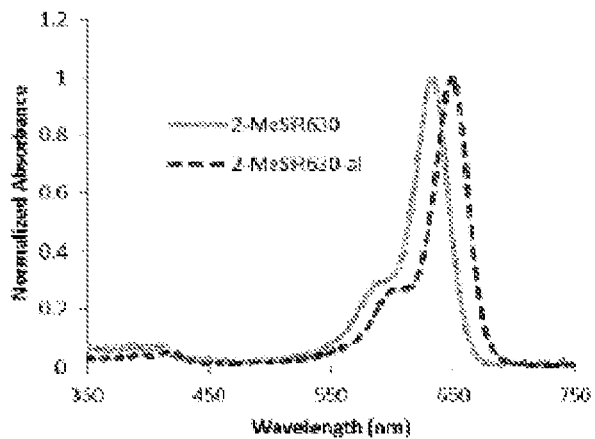
FIG. 2a Absorbance profile of 2-MeSiR630 (Compound 3) and 2-MeSiR630-a1 (Compound 4).
Figure 2B:
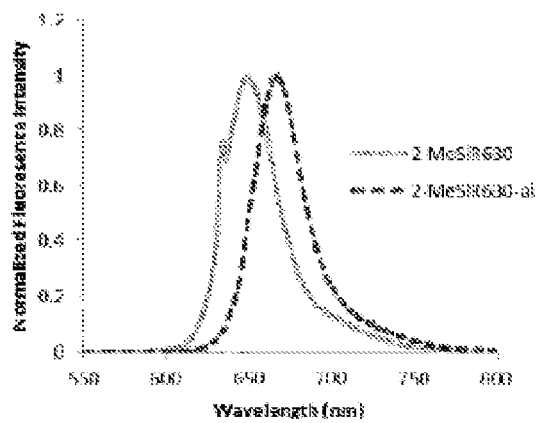
FIG. 2b Fluorescence profile of 2-MeSiR630 (Compound 3) and 2-MeSiR630-a1 (Compound 4).

(Compound 4) synthesized in step (d) were measured. The results are shown in FIGS. 2a and 2b. Measurements were carried out in an aqueous solution of 0.1 sodium phosphate having a pH 7.4 and containing 0.1% DMSO. The excitation light in the fluorescence spectrum measurement was 633 nm for 2-MeSiR630 and 648 nm for 2-MeSiR630-a1.

The optical characteristic data of Compound 3 and Compound 4 is summarized in Table 2.

TABLE 2

| | $Abs_{max}{}^a$ (nm) | $\epsilon^a$ (M$^{-1}$cm$^{-1}$) | $Em_{max}{}^a$ (nm) | $\Phi_{fl}{}^{ab}$ |
| --- | --- | --- | --- | --- |
| Compound 3 | 633 | 120,000 | 649 | 0.11 |
| Compound 4 | 648 | 140,000 | 666 | 0.30 |

$^a$Measurement carried out in pH 7.4 sodium phosphate buffer solution
$^b$Cresyl violet in methanol ($\Phi_{fl}$ = 0.54) was used as the fluorescence reference Example 3

Compound 5 of the present invention was synthesized using the following synthesis scheme.

Scheme 4

[Chemical Formula 40]

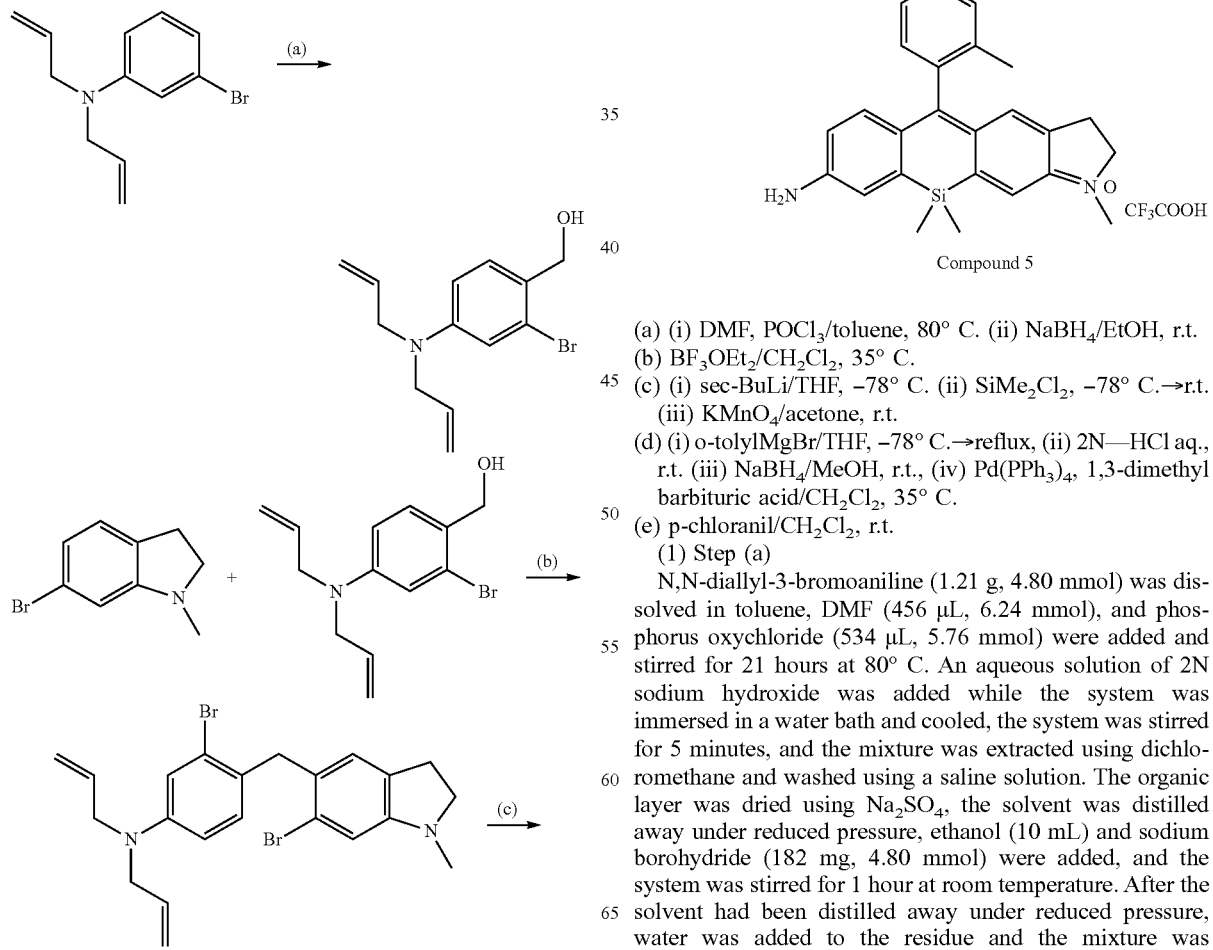

(a) (i) DMF, POCl$_3$/toluene, 80° C. (ii) NaBH$_4$/EtOH, r.t.
(b) BF$_3$OEt$_2$/CH$_2$Cl$_2$, 35° C.
(c) (i) sec-BuLi/THF, −78° C. (ii) SiMe$_2$Cl$_2$, −78° C.→r.t.
  (iii) KMnO$_4$/acetone, r.t.
(d) (i) o-tolylMgBr/THF, −78° C.→reflux, (ii) 2N—HCl aq., r.t. (iii) NaBH$_4$/MeOH, r.t., (iv) Pd(PPh$_3$)$_4$, 1,3-dimethyl barbituric acid/CH$_2$Cl$_2$, 35° C.
(e) p-chloranil/CH$_2$Cl$_2$, r.t.

(1) Step (a)

N,N-diallyl-3-bromoaniline (1.21 g, 4.80 mmol) was dissolved in toluene, DMF (456 μL, 6.24 mmol), and phosphorus oxychloride (534 μL, 5.76 mmol) were added and stirred for 21 hours at 80° C. An aqueous solution of 2N sodium hydroxide was added while the system was immersed in a water bath and cooled, the system was stirred for 5 minutes, and the mixture was extracted using dichloromethane and washed using a saline solution. The organic layer was dried using Na$_2$SO$_4$, the solvent was distilled away under reduced pressure, ethanol (10 mL) and sodium borohydride (182 mg, 4.80 mmol) were added, and the system was stirred for 1 hour at room temperature. After the solvent had been distilled away under reduced pressure, water was added to the residue and the mixture was extracted using dichloromethane. The organic layer was dried using Na$_2$SO$_4$, the solvent was distilled away under reduced pressure, and the residue was refined using column chromatography (silica gel, 30% ethyl acetate/n-hexane) to obtain N,N-diallyl-3-bromo-4-hydroxymethyl aniline (1.15 g, 4.08 mmol, yield: 85%).

$^1$H NMR (300 MHz, CDCl$_3$): δ 3.89-3.91 (m, 4H), 4.62 (d, J=6.0 Hz, 2H), 5.12-5.19 (m, 4H), 5.76-5.88 (m, 2H), 6.60 (dd, J=2.3, 8.6 Hz, 1H), 6.86 (d, J=2.3 Hz, 1H), 7.20 (d, J=8.6 Hz, 1H); $^{13}$C NMR (75 MHz, CDCl$_3$) δ 52.69, 65.04, 111.31, 115.86, 116.31, 124.43, 136.95, 130.45, 133.02, 149.35; LRMS (ESI+) 264 [M−OH]$^+$ (2) Step (b)

6-bromo-1-methylindoline (105 mg, 0.495 mmol), N,N-diallyl-3-bromo-4-hydroxymethyl aniline (137 mg, 0.488 mmol) were dissolved in dichloromethane (15 mL), BF$_3$OEt$_2$ (123 μL, 0.976 mmol) was added, and the system was stirred for 23 hours at 35° C. The system was cooled to room temperature, water was added thereafter, and the mixture was extracted using dichloromethane and washed using a saline solution. The organic layer was dried using Na$_2$SO$_4$, the solvent was distilled away under reduced pressure, and the residue was refined using column chromatography (silica gel, 10% ethyl acetate/n-hexane) to obtain N,N-diallyl-3-bromo-4-((6-bromo-1-methylindoline-5-yl)methyl) aniline (207 mg, 0.434 mmol, yield: 90%).

$^1$H NMR (300 MHz, CDCl$_3$): δ 2.73 (s, 3H), 2.83 (t, J=8.1 Hz, 2H), 3.28 (t, J=8.1 Hz, 2H), 3.87-3.88 (m, 4H), 3.97 (s, 2H), 5.14-5.20 (m, 4H), 5.76-5.89 (m, 2H), 6.64 (dd, J 2.5, 8.2 Hz, 1H), 6.65 (s, 1H), 6.73 (s, 1H), 6.80 (d, J=8.2 Hz, 1H), 6.90 (d, J=2.5 Hz, 1H); $^{13}$C NMR (75 MHz, CDCl$_3$) δ 28.36, 36.03, 40.14, 52.72, 56.28, 110.85, 111.64, 115.92, 116.27, 123.06, 125.49, 126.11, 127.05, 128.05, 130.17, 130.68, 133.52, 148.13, 153.03; LRMS (ESI$^+$) 477 [M+H]$^+$ (3) Step (c)

N,N-diallyl-3-bromo-4-((6-bromo-1-methylindoline-5-yl)methyl) aniline (207 mg, 0.434 mmol) and anhydrous tetrahydrofuran (10 mL) were added to a dry, argon-substituted flask. The system was cooled to −78° C., 1M sec-butyl lithium (0.91 mL, 0.91 mmol) was added, and the system was stirred for 20 minutes. Dichlorodimethylsilane (112 mg, 0.868 mmol) was dissolved in 3 mL of anhydrous tetrahydrofuran and slowly added with the temperature unchanged. The system was restored to room temperature and stirred for one hour. The reaction was stopped using 2N hydrochloric acid and the system was neutralized using NaHCO$_3$. The mixture was extracted using dichloromethane and washed using a saline solution. The organic layer was dried using Na$_2$SO$_4$, and the solvent was distilled away under reduced pressure. The residue was dissolved in acetone (30 mL) and cooled to 0° C., KMnO$_4$ (295 mg, 1.74 mmol) was added over 2 hours in small amounts, and the system was stirred for one hour at the same temperature. Dichloromethane was added, the system was suction-filtered using filter paper, water was added thereafter, and the mixture was extracted using dichloromethane and washed using a saline solution. The organic layer was dried using Na$_2$SO$_4$, the solvent was distilled away under reduced pressure, and the residue was then refined using column chromatography (silica gel, 30% ethyl acetate/n-hexane) to obtain 8-(diallylamino-1,10,10-trimethyl-2,3-dihydro-1H-benzo[5,6]silino[3,2-f]indole-5 (10H)-one (30 mg, 0.0773 mmol, yield: 18%).

$^1$H NMR (300 MHz, CDCl$_3$): δ 0.43 (s, 6H), 2.90 (s, 3H), 3.05 (t, J=8.5 Hz, 2H), 3.47 (t, J=8.5 Hz, 2H), 4.02-4.03 (m, 4H), 5.18-5.23 (m, 4H), 5.82-5.94 (m, 2H), 6.50 (s, 1H), 6.80-6.86 (m, 2H), 8.21 (s, 1H), 8.34 (d, J=9.0 Hz, 1H); $^{13}$C NMR (100 MHz, CDCl$_3$) δ −1.17, 28.03, 34.55, 52.65, 54.79, 107.89, 107.93, 113.37, 114.65, 116.52, 120.40, 126.03, 129.98, 131.47, 131.59, 132.12, 133.04, 140.12, 140.27, 150.00, 154.80, 185.05; HRMS (ESI$^+$) Calcd for [M+H]$^+$, 389.2049. Found, 389.2069 (+2.0 mmu).

(4) Step (d)

8-(diallylamino-1,10,10-trimethyl-2,3-dihydro-1H-benzo[5,6]silino[3,2-f]indole-5(10H)-one (14 mg, 0.036 mmol) was dissolved in THF (5 mL), o-tolyl magnesium bromide (19% in THF) (3.6 mL, 3.6 mmol) was added, and the system was heated and allowed to reflux for 2.5 hours. Next, an aqueous solution of 2N hydrochloric acid was added to the reaction liquid to quench the reaction, a saturated aqueous solution of sodium hydrogencarbonate was added to neutralize the system, the mixture was extracted using dichloromethane, the organic layer was dried using Na$_2$SO$_4$, and the solvent was distilled away under reduced pressure. The residue was dissolved in MeOH (15 mL), NaBH$_4$ (1.5 mg, 40 μmol) was added, and the systems was stirred for 5 minutes as room temperature. The solvent was distilled away under reduced pressure, water was added, the mixture was extracted using dichloromethane, the organic layer was washed using a saline solution and dried using Na$_2$SO$_4$, and the solvent was distilled away under reduced pressure. The residue was dissolved in dichloromethane, 1,3-dimethylbarbituric acid (28 mg, 0.18 mmol) and tetrakis triphenylphosphine palladium (5.7 mg, 5.4 μmol) were added, and the system was stirred for 11 hours in an argon atmosphere at 35° C. A saturated aqueous solution of sodium hydrogencarbonate was added, the mixture was extracted using dichloromethane, the organic layer was dried using Na$_2$SO$_4$, the solvent was distilled away under reduced pressure, and the residue was then refined using column chromatography (silica gel, 20% ethyl acetate/n-hexane) to obtain 1,10,10-trimethyl-5-(o-tolyl)-2,3,5,10-tetrahydro-1H-benzo[5,6]silino[3,2-f]indole-8-amine (2.0 mg, 5.19 μmol, yield: 14%).

$^1$H NMR (300 MHz, CDCl$_3$): δ 0.41 (s, 3H), 0.56 (s, 3H), 2.29 (s, 3H), 2.81-2.85 (m, 5H), 3.26 (t, J=8.1 Hz, 2H), 5.56, (s, 1H), 6.56 (dd, J=2.7, 8.1 Hz, 1H), 6.71 (s, 1H), 6.77 (s, 1H), 6.81 (d, J=8.1 Hz, 1H), 6.91 (d, J=2.7 Hz, 1H), 7.05-7.13 (m, 4H)

(5) Step (e)

1,10,10-trimethyl-5-(o-tolyl)-2,3,5,10-tetrahydro-1H-benzo[5,6]silino[3,2-f]indole-8-amine (2.0 mg, 5.2 μmol) was dissolved in dichloromethane (5 mL), p-chloranil (2.6 mg, 10.4 μmol) was added, and the system was stirred for 2 hours at room temperature. The solvent was distilled away under reduced pressure, and the residue was then refined by neutral fractionation using HPLC to obtain the target fluorescent dye (Compound 5) (1.2 mg, 2.5 μmol, yield: 48%).

$^1$H NMR (300 MHz, CD$_2$Cl$_2$): δ 0.54 (s, 3H), 0.56 (s, 3H). 2.03 (s, 3H), 2.96 (t, J=8.0 Hz, 2H), 3.21 (s, 3H), 3.83 (t, J=8.0 Hz, 2H), 6.58 (d, J=8.7 Hz, 1H), 6.79 (s, 1H), 6.91 (s, 1H), 6.95 (d, J=8.7 Hz, 1H), 7.09 (d, J=7.2 Hz, 1H), 7.29-7.43 (m, 4H); HRMS (ESI$^+$) Calcd for [M]$^+$, 383.1944. Found, 383.1484 (+4.0 mmu).

Figure 3:
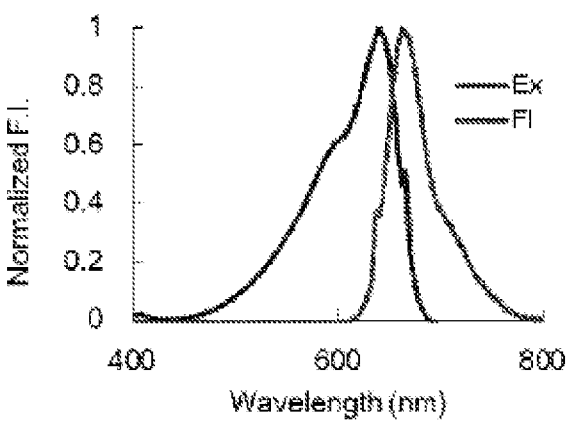
FIG. 3 Absorbance and fluorescence spectra of 2MeIndoSiR (Compound 5).

The absorbance and fluorescence spectra of the fluorescent dye 2MeIndoSiR (Compound 5) obtained in example 3 were measured. The results are shown in FIG. 3. The fluorescence wavelength was 665 nm and the wavelength of the excitation light was 637 nm.

The optical characteristic data of Compound 5 is summarized in Table 3. The measurement was carried out in an aqueous solution of 0.1 sodium phosphate having a pH 7.4 and containing 0.3% DMSO. Cy 5.5 ($\Phi_{Fl}$=0.23) in water was used as the fluorescence reference to determine the fluorescence quantum yield.

TABLE 3

Optical characteristics of Compound 5

|  | ε (M⁻¹cm⁻¹) | $\Phi_{fl}^c$ | $\lambda_{ex}$ (nm) | $\lambda_{em}$ (nm) |
|---|---|---|---|---|
| Compound 5 | 54000 | 0.18 | 641 | 665 |

Figure 4:
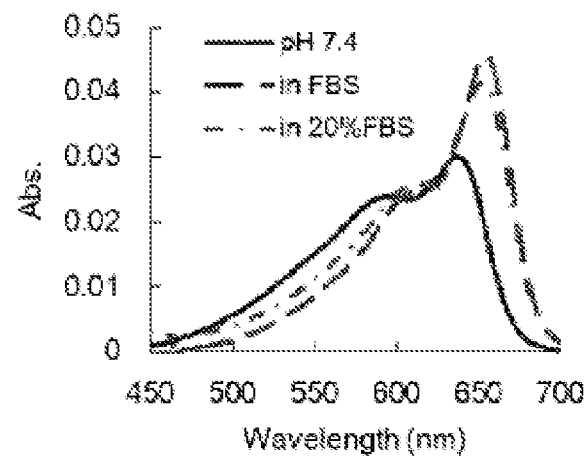
FIG. 4 Absorbance spectrum of 2MeIndoSiR (Compound 5) in FBS.

Next, the absorbance spectrum of Compound 5 in fetal bovine serum (FBS) was measured, and the results are shown in FIG. 4.

Measurement was performed in an aqueous solution of 0.1M sodium phosphate, an FBS solution, and an aqueous solution of 20% FBS sodium phosphate containing 1% DMSO.

Table 4 shows the fluorescence quantum yield of 2MeIndoSiR in various solvents. Cy 5.5 ($\Phi_{Fl}$=0.23) in water was used as the fluorescence reference to determine the fluorescence quantum yield.

TABLE 4

Fluorescence quantum yield of Compound 5 in various solvents

|  | CHCl₃ | MeOH | DMSO | DMF | CH₃CN | acetone | FBS | 20% FBS |
|---|---|---|---|---|---|---|---|---|
| $\Phi_{Fl}$ | 0.89 | 0.46 | 0.35 | 0.39 | 0.42 | 0.39 | 0.35 | 0.36 |

Figure 5:
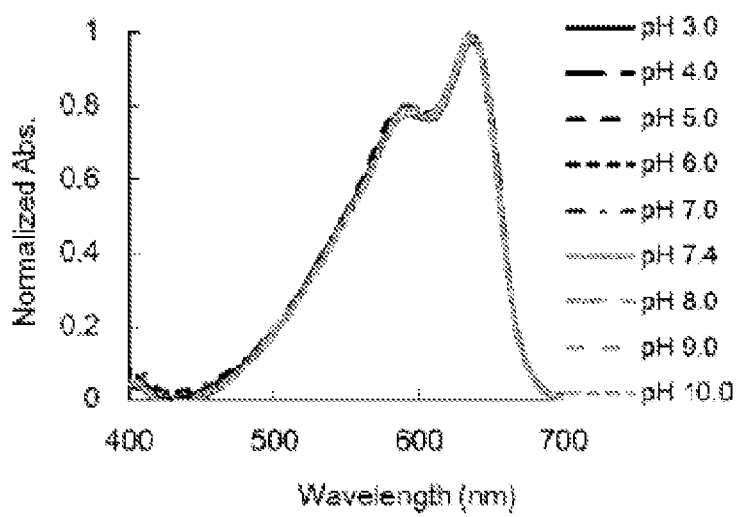
FIG. 5 pH profile of the absorbance spectrum of 2MeIndoSiR (Compound 5).
Figure 6:
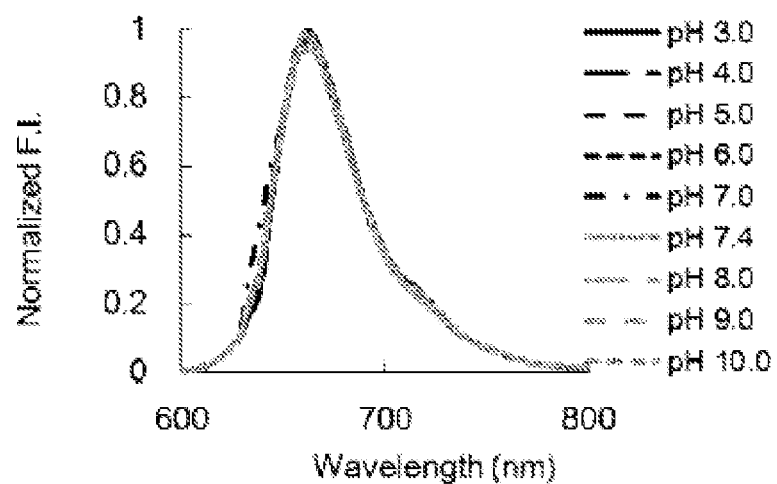
FIG. 6 pH profile of the fluorescence spectrum of 2MeIndoSiR (Compound 5).

Furthermore, the pH profile of the absorbance spectrum and fluorescence spectrum of Compound 5 was examined. The results thereof are shown in FIGS. 5 and 6. Measurement was carried out at various pH levels in a solution of 0.1M sodium phosphate containing 1% DMSO. The excitation wavelength was 637 nm.

Example 4

Compound 5 of the present invention was synthesized using the following different synthesis route.

Scheme 5

[Chemical Formula 41]

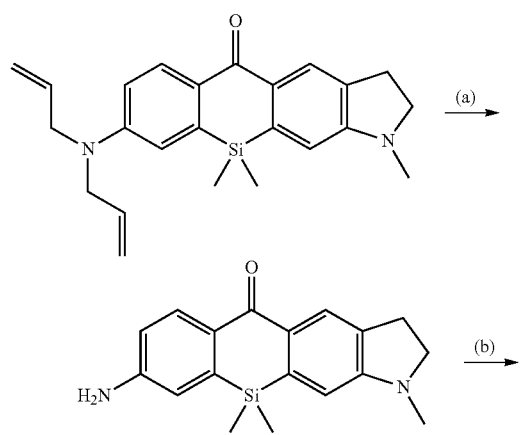

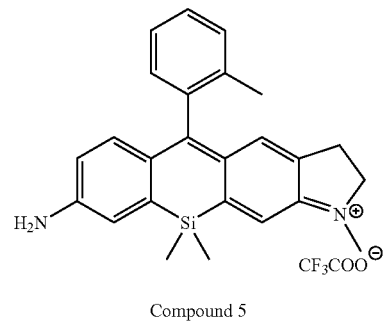

Compound 5

(a) Pd(PPh₂)₄, 1,3-dimethylbarbituric acid/CH₂Cl₂, 35° C.
(b) (i) o-tolyl MgBr/THF, r.t.→reflux (ii) 2N—HCl aq.

(1) Step (a)

8-(diallylamino-1,10,10-trimethyl-2,3-dihydro-1H-benzo[5,6]silino[3,2-f]indole-5(10H)-one (102 mg, 0.263 mmol) was dissolved in dichloromethane (15 mL), 1,3-dimethylbarbituric acid (206 mg, 1.32 mmol) and tetrakis triphenylphosphine palladium (42 mg, 0.0395 mmol) were added, and the system was stirred for 12 hours in an argon atmosphere at 35° C. A saturated solution of sodium hydrogencarbonate was added to the mixture, the mixture was extracted using dichloromethane, the organic layer was dried using Na₂SO₄, the solvent was distilled away under reduced pressure, and the residue was then refined using column chromatography (silica gel, 40% ethyl acetate/n-hexane) to obtain 8-amino-1,10,10-trimethyl-2,3-dihydro-1H-benzo[5,6]silino[3,2-f]indole-5(10H)-one (78 mg, 0.253 μmol, yield: 96%).

¹H NMR (300 MHz, CDCl₂): δ 0.43 (s, 6H), 2.90 (s, 3H), 3.04 (t, J=8.2 Hz, 2H), 3.47 (t, J=8.2 Hz, 2H), 6.49 (s, 1H), 6.76-6.82 (m, 2H), 8.20 (s, 1H), 8.31 (d, J=8.1 Hz, 1H); ¹³C NMR (75 MHz, CDCl₃) δ −1.28, 27.96, 34.44, 54.73, 107.79, 107.84, 116.12, 117.51, 126.10, 131.15, 131.84, 132.20, 140.12, 140.80, 148.83, 154.91, 185.13; HRMS (ESI⁺) Calcd for [M+H]⁺, 309.1423. Found, 389.1426 (+0.3 mmu).

(2) Step (b) 8-amino-1,10,10-trimethyl-2,3-dihydro-1H-benzo[5,6]silino[3,2-f]indole-5(10H)-one (8.7 mg, 0.0282 mmol) was dissolved in THF (5 mL), o-tolyl magnesium bromide (19% in THF) (2.82 mmol, 2.8 mL) was added, and the system was heated and allowed to reflux for 2 hours. An aqueous solution of 2N hydrochloric acid was added to the reaction liquid to quench the reaction, a saturated aqueous solution of sodium hydrogencarbonate was added to neutralize the system, the mixture was extracted using dichloromethane, the organic layer was dried using Na₂SO₄, and the solvent was distilled away under reduced pressure. The residue was refined by HPLC to obtain the target fluorescent dye (Compound 5) (5.3 mg, 38%).

¹H NMR (300 MHz, CD₂Cl₂): δ 0.54 (s, 3H), 0.56 (s, 3H). 2.03 (s, 3H), 2.96 (t, J=8.0 Hz, 2H), 3.21 (s, 3H), 3.83 (t, J=8.0 Hz, 2H), 6.58 (d, J=8.7 Hz, 1H), 6.79 (s, 1H), 6.91 (s, 1H), 6.95 (d, J=8.7 Hz, 1H), 7.09 (d, J=7.2 Hz, 1H), 7.29-7.43 (m, 4H); HRMS (ESL') Calcd for [M]⁺, 383.1944. Found, 383.1484 (+4.0 mmu).

Example 5

Compound 6 (Ac-IndoSiR) of the present invention was synthesized using the following scheme.

Scheme 6

[Chemical Formula 42]

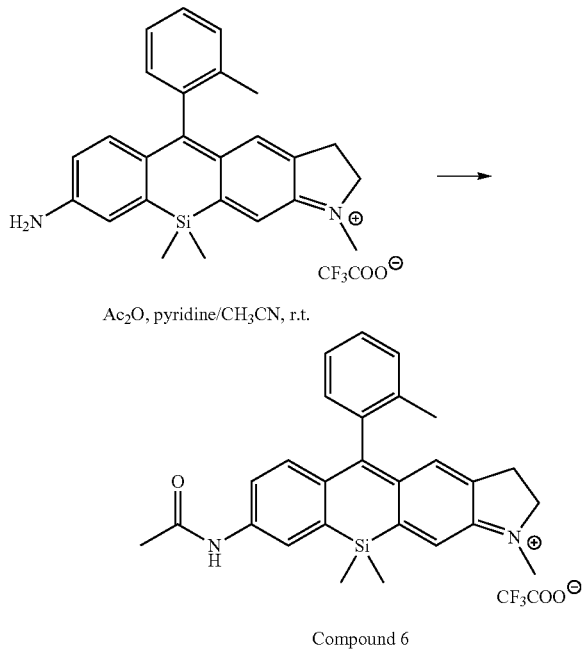

Compound 6

Compound 5 (0.7 mg, 1.41 μmol) obtained in example 3 or 4 was dissolved in acetonitrile (3 mL). Acetic anhydride (5 μL, 49 μmol) and pyridine (5 μL, 63.3 μmol) were added thereto, and the system was stirred for 71 hours at room temperature. An aqueous solution of 2N hydrochloric acid was added to the reaction solution, the mixture was extracted using dichloromethane, the organic layer was dehydrated using anhydrous sodium sulfate, and the solvent was distilled away under reduced pressure. The residue was refined by neutral fractionation by HPLC to obtain Ac-IndoSiR (Compound 6) (0.5 mg, 1.03 μmol, 73%).

$^1$H NMR (300 MHz, $CD_2Cl_2$): δ 0.43 (s, 3H), 0.48 (s, 3H). 2.12 (s, 3H), 2.67 (s, 3H) 2.76-2.81 (m, 5H), 3.24 (t, J=8.4 Hz, 2H), 6.53 (s, 1H), 6.78 (s, 1H), 6.87 (d, J=7.5 Hz, 1H), 7.01 (d, J=8.7 Hz, 1H) 7.12-7.39 (m, 3H), 7.69 (s, J=1.8 Hz, 1H), 8.33 (dd, J=8.7, 1.8 Hz, 1H); HRMS (ESI$^+$) Calcd for [M]$^+$, 425.2049. Found, 425.2090 (+4.1 mmu).

Figure 7:
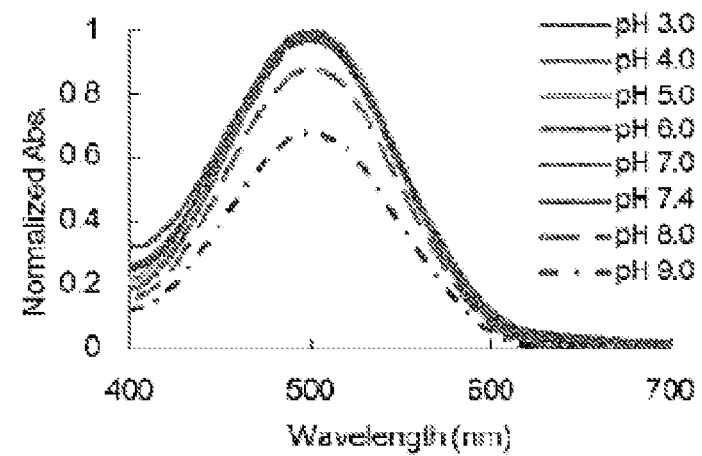
FIG. 7 pH profile of the absorbance spectrum of Ac-IndoSiR (Compound 6).
Figure 8:
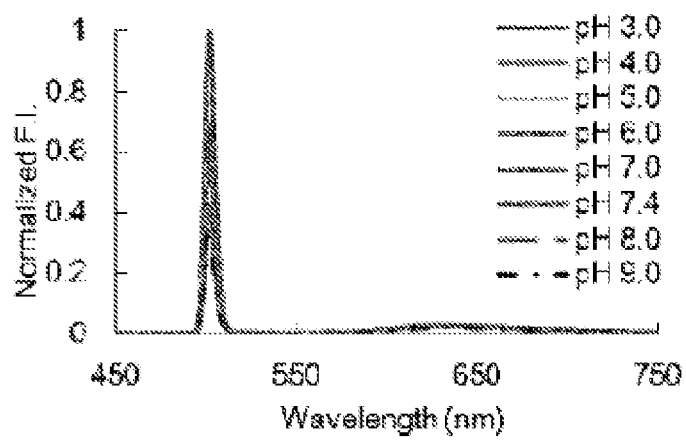
FIG. 8 pH profile of the fluorescence spectrum of Ac-IndoSiR (Compound 6).

The pH profile of the absorbance and fluorescence spectra of Compound 6 was examined. The results thereof are shown in FIGS. 7 and 8. Measurement was carried out at various pH in 0.1M sodium phosphate solution containing 1% DMSO. The excitation wavelength was 500 nm.

Figure 9:
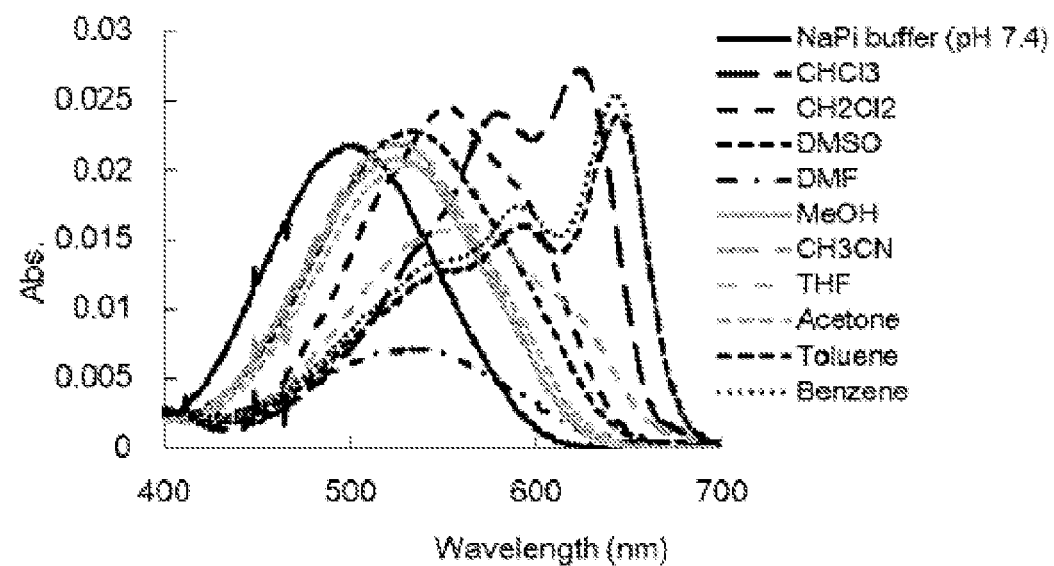
FIG. 9 Absorbance spectrum of Ac-IndoSiR (Compound 6) in various solvents.
Figure 10:
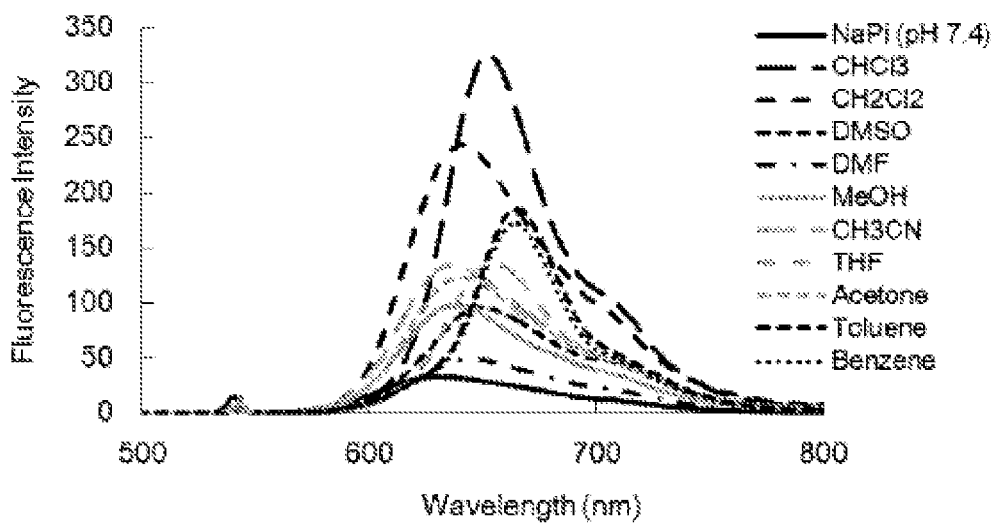
FIG. 10 Fluorescence spectrum of Ac-IndoSiR (Compound 6) in various solvents.

Next, the absorbance and fluorescence spectra of Ac-IndoSiR (Compound 6) in various solvents were measured. The results thereof are shown in FIGS. 9 and 10. The measured solvents were pH 7.4 NaPi buffer, chloroform, dichloromethane, DMSO, DMF, methanol, acetonitrile, tetrahydrofuran, acetone, toluene, and benzene, and all solvents contained 0.1% DMSO. The excitation wavelength was 540 nm.

The maximum absorbance fluorescence wavelength, molar absorbance coefficient, and fluorescence quantum yield of Compound 6 in various solvents are shown in Table 5. The fluorescence quantum yield ($\Phi_{Fl}$=0.44; determined using an absolute fluorescence quantum yield measurement device) of Compound 6 in chloroform was used as the fluorescence reference to determine the fluorescence quantum yield in various solvents.

TABLE 5

| | $\Phi_{Fl}$ | Abs$_{max}$ (nm) | Em$_{max}$ (nm) | ε ($M^{-1}cm^{-1}$) |
|---|---|---|---|---|
| NaPi buffer (pH 7.4) | 0.06 | 500 | 630 | 29,000 |
| $CHCl_3$ | 0.44 | 623 | 652 | 36,000 |
| $CH_2Cl_2$ | 0.27 | 552 | 641 | 33,000 |
| DMSO | 0.12 | 534 | 651 | 30,000 |
| DMF | 0.19 | 536 | 645 | 9,000 |
| MeOH | 0.10 | 526 | 637 | 27,000 |
| $CH_3CN$ | 0.16 | 529 | 636 | 29,000 |
| THF | 0.18 | 559 | 654 | 21,000 |
| Acetone | 0.15 | 532 | 641 | 27,000 |
| Toluene | 0.31 | 644 | 665 | 32,000 |
| Benzene | 0.26 | 644 | 665 | 34,000 |

Figure 11:
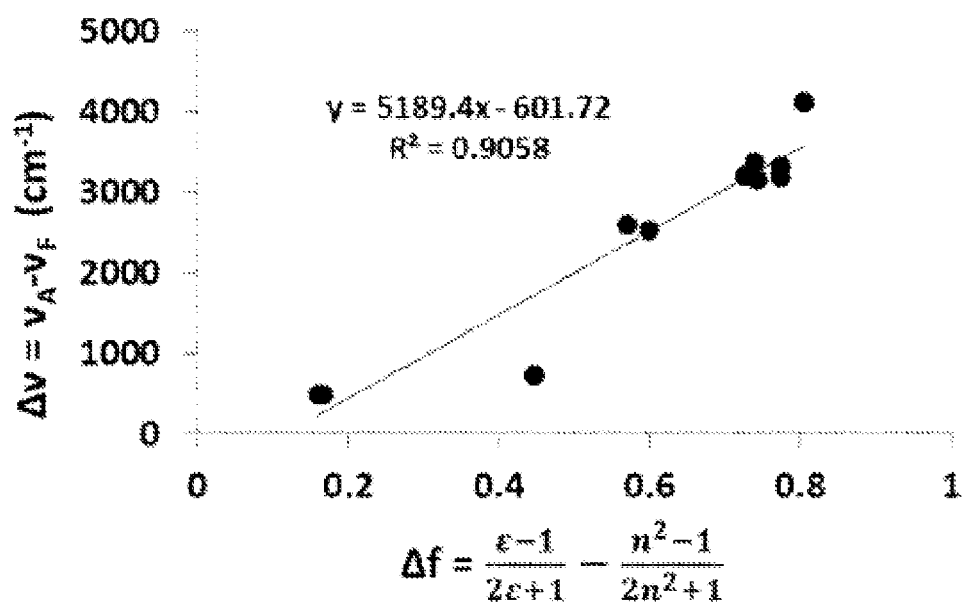
FIG. 11 Lippert-Mataga plot for Ac-IndoSiR (Compound 6).

A Lippert-Mataga plot was created with Stokes shift ΔV of Compound 6 in the solvents plotted in relation to the orientation polarizability Δf of the solvents shown in Table 5, and a linear relationship was found between the two (FIG. 11, ∈ is the dielectric constant of the solvents, and n is the refractivity of the solvents). Therefore, it is apparent that the solvent effect is an important factor in the spectral shift of Compound 6. In other words, Compound 6 is a fluorescent dye that exhibits environment sensitivity.

Compound 6 had an absorbance maximum wavelength of 500 nm in water, which is a polar solvent, and a low fluorescence quantum yield of 0.06. On the other hand, the absorbance maximum wavelength was an extended long-wavelength of 644 nm in toluene, which is a low-polarity solvent, and the fluorescence quantum yield was considerably higher at 0.31 (Table 5). Thus, Compound 6 has an extended long-wavelength and a higher fluorescence quantum yield in hydrophobic environments. Accordingly, shining an excitation light having a long-wavelength of 600 nm or greater allows visibilization of hydrophobic environments because only Compound 6 is excited in a hydrophobic environment and the emitted fluorescent light can be detected.

Environment-sensitive dyes that are fluorescent in a hydrophobic environment are used for simple detection of interaction between proteins and bonding of proteins and substrates. With this technique, an environment-sensitive dye is introduced into a researched protein, and change in hydrophobicity near the dye in accompaniment with substrate bonding or interaction between proteins is detected using fluorescent light. The present technique is advantageous in that protein present in a living cell can be observed in real time, and many examples of such utility have been reported in recent years (Review: Trends in Biotechnology, 2009, 28, 73-83). It is anticipated that Compound 6 will also have application to detection of interaction between proteins and bonding of proteins and substrates in the same manner as previously reported environment-sensitive dyes.

The absorbance wavelength of environment-sensitive fluorescent dyes in common use is a relatively short wavelength of 350 to 500 nm. On the other hand, Ac-IndoSiR has long-wavelength fluorophore Si Rhodamine as a mother nucleus, and the absorbance wavelength thereof is 500 to 650 nm (FIGS. 9 and 10, Table 5). Therefore, there are two advantages to using Ac-IndoSiR in living-cell imaging in comparison with existing environment-sensitive fluorescent dyes. First, cell damage due to excitation light is reduced. Cell damage due to short-wavelength excitation light is often a problem in living cell imaging, but the absorbance wavelength of Ac-IndoSiR is in the wavelength region of 500 nm or greater, resulting in low injury to living cells. Imaging using long-wavelength excitation light with low injury to living cells is therefore made possible. Second, there is high-sensitive imaging in which biomolecule-induced auto-fluorescence is inhibited. Biological tissue emits auto-fluorescence from fluorescent biomolecules due to excitation light emissions, and auto-fluorescence is reduced as the excitation wavelength is increased. Accordingly, high-sensitive imaging is anticipated because auto-fluorescence is inhibited by the use of Ac-IndoSiR, which has a long wavelength in comparison with existing environment-sensitive dyes.

Example 6

Compound 7 (Si-Rhodol) of the present invention was synthesized using the following scheme.

Scheme 7

[Chemical Formula 43]

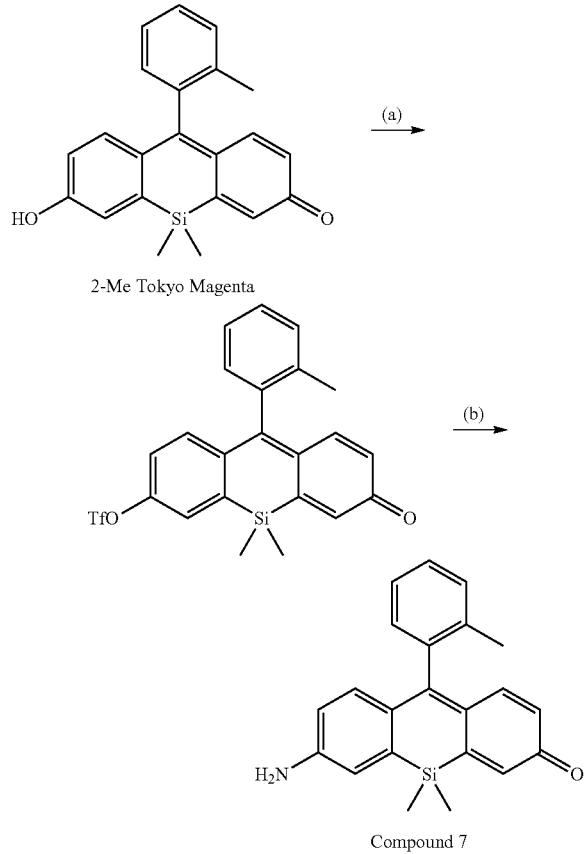

(a) $Tf_2O$, pyridine/$CH_2Cl_2$, −30° C.
(b) (i) $Pd_2(dba)_3CHCl_3$, xantphos, $Cs_2CO_3$, benzophenone imine/toluene, 100° C. (ii) 2N—HCl aq./THF, r.t.

(1) Step (a)

2-MeTM (52 mg, 0.15 mmol) was dissolved in dichloromethane (10 mL), pyridine was added thereto, and the system was cooled to −30° C. A solution in which $Tf_2O$ (49 µL, 0.3 mmol) had been dissolved in dichloromethane (3 mL) was dropped into the reaction liquid and the system was stirred for 10 minutes at room temperature. Water was added to the mixture and the resultant was extracted using dichloromethane. The organic layer was dried using $Na_2SO_4$, the solvent was distilled away under reduced pressure, and the residue was refined by column chromatography (silica gel, 30% ethyl acetate/n-hexane) to obtain TM-OTf (73 mg, 0.15 mmol, quant.).

$^1$H-NMR (300 MHz, $CDCl_3$): δ 0.52 (s, 3H), 0.54 (s, 3H), 2.06 (s, 3H), 6.27 (d, J=5.1 Hz 2H), 6.86 (s, 1H), 6.96-6.98 (m, 2H), 7.11-7.13 (m, 2H), 7.34-7.49 (m, 4H); $^{13}$C-NMR (75 MHz, $CDCl_3$) δ −1.78, −1.50, 19.47, 116.52, 122.61, 126.11, 126.31, 128.69, 128.81, 129.27, 130.45, 131.02, 134.54, 136.01, 137.93, 138.38, 140.84, 141.01, 141.18, 145.83, 149.52, 152.47, 184.18; HRMS (ESI$^+$) Calcd for [M+H]$^+$, 477.0804. Found, 477.0770 (−3.4 mmu).

(2) Step (b)

TM-OTf (7.3 mg, 15.67 µmol) was dissolved in toluene (8 mL), then $Pd_2(dba)_3CHCl_3$ (1.6 mg, 1.57 µmol), xantphos (2.4 mg, 4.14 µmol), $Cs_2CO_3$ (7.1 mg, 21.9 µmol), and benzophenone imine (3.4 µL, 18.8 µmol) were added thereto, and the system was stirred for 20 hours at 100° C. in an argon atmosphere. The reaction liquid was cooled to room temperature, dichloromethane was added, the system was filter through celite, and the solvent was distilled away under reduced pressure. THF (10 mL) and an aqueous solution of 2N hydrochloric acid (10 mL) were added to the residue and the system was stirred for 30 minutes at room temperature. A saturated aqueous solution of sodium hydrogencarbonate was added to neutralize the system, and the mixture was extracted using dichloromethane. The organic layer was dried using $Na_2SO_4$, the solvent was distilled away under reduced pressure, and the residue was refined by column chromatography (silica gel, 3% methanol/dichloromethane) to obtain Si-Rhodol (Compound 7) (6.9 mg, quant.).

$^1$H-NMR (400 MHz, $CD_3OD$): δ 0.37 (s, 3H), 0.38 (s, 3H), 1.94 (s, 3H), 6.12 (dd, J=9.4, 1.9 Hz, 1H), 6.36 (dd, J=9.6, 2.4 Hz, 1H), 6.66 (d, J=9.4 Hz, 1H), 6.77 (d, J=1.9 Hz, 1H), 6.88 (d, J=9.6 Hz, 1H), 6.96 (d, J=2.4 Hz, 1H), 6.98 (d, J=7.6 Hz, 1H), 7.21-7.33 (m, 3H); $^{13}$C-NMR (100 MHz, $CD_3OD$) δ −1.47, −1.24, 19.49, 115.75, 122.20, 125.67, 126.68, 127.23, 128.91, 129.51, 130.21, 131.12, 134.43, 137.02, 139.42, 140.89, 144.17, 144.99, 150.26, 154.42, 164.99, 184.72: HRMS (ESI$^-$) Calcd for [M]$^+$, 477.0804. Found, 477.0770 (−3.4 mmu).

Figure 12:
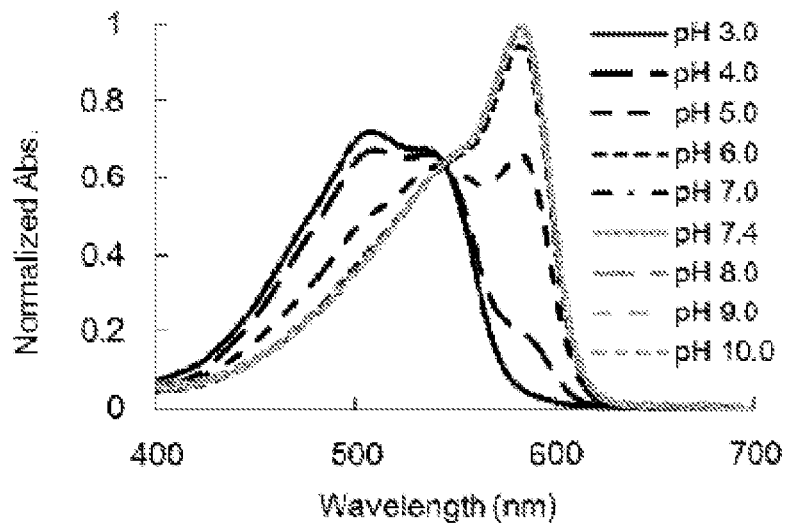
FIG. 12 pH profile of the absorbance spectrum of Si-Rhodol (Compound 7).
Figure 13:
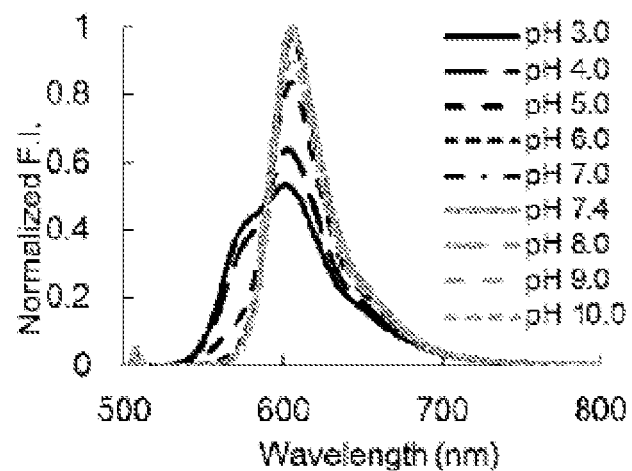
FIG. 13 pH profile of the fluorescence spectrum of Si-Rhodol (Compound 7) (excitation wavelength: 507 nm).
Figure 14:
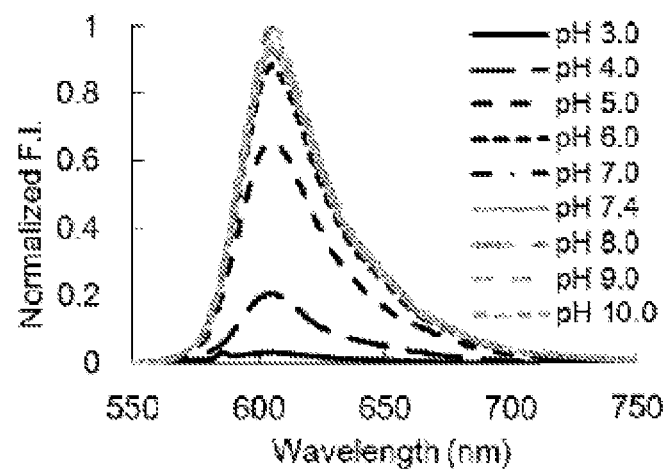
FIG. 14 pH profile of the fluorescence spectrum of Si-Rhodol (Compound 7) (excitation wavelength: 584 nm).

The pH profile of the absorbance and fluorescence spectra of Si-Rhodol (Compound 7) was examined. The results are shown in FIGS. 12 to 14. Measurement was carried out at various pH in 0.1M sodium phosphate solution containing 1% DMSO. The excitation wavelengths were 507 nm (FIG. 13) and 584 nm (FIG. 14).

The optical characteristics of Compound 7 are summarized in the following table.

| | ε ($M^{-1}cm^{-1}$) | $\Phi_{fl}{}^c$ | $\lambda_{abs}$ (nm) | $\lambda_{em}$ (nm) |
| --- | --- | --- | --- | --- |
| Compound 7 | 40,000 | 0.28 (pH: 3.0) 0.56 (pH: 7.4) | 507 (pH: 3.0) 584 (pH: 7.4) | 605 |

Example 7

A Si-Rhodol analogue was synthesized using the following scheme.

Scheme 8

[Chemical Formula 44]

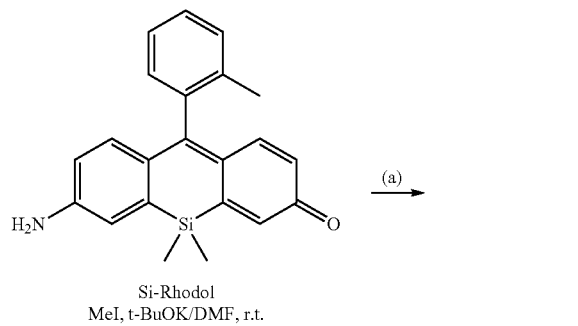

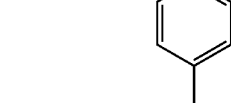

Si-Rhodol
MeI, t-BuOK/DMF, r.t.

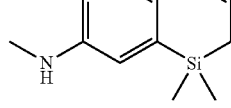

17%

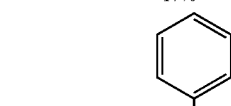

12%

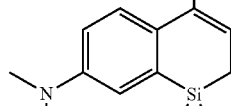

3%

Step (a)

Si-Rhodol (Compound 7) (6.9 mg, 20 μmol) was dissolved in DMF (6 mL), then MeI (1.75 μL, 28 μmol) and t-BuOK (3.4 mg, 30 μmol) were added thereto, and the system was stirred for 28 hours at room temperature. An aqueous solution of 2N hydrochloric acid was added to the mixture, the resultant was extracted using dichloromethane, the organic layer was dried using $Na_2SO_4$, the solvent was distilled away under reduced pressure, the residue was refined by HPLC to obtain N-MeSi-Rhodol (1.2 mg, 3.4 μmol, 17%), N-diMeSi-Rhodol (0.9 mg, 2.4 μmol, 12%), and O-MeSi-Rhodol (0.2 mg, 0.56 μmol, 3%).

[Chemical Formula 45]

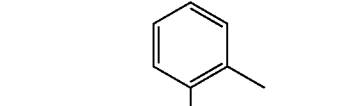

N—Me Si-Rhodol $^1$H-NMR (400 MHz, $CDCl_3$): δ 0.45 (s, 3H), 0.46 (s, 3H), 2.04 (s, 3H), 3.12 (s, 3H), 6.54 (d, J=9.1 Hz, 1H), 6.66 (d, J=9.1 Hz, 1H), 6.98 (s, 1H), 7.00 (s, 1H), 7.07 (m, 2H), 7.19 (d, J=7.8 Hz, 1H), 7.32 (d, J=7.2 Hz, 1H), 7.41 (t, J=7.8 Hz, 2H): HRMS (ESI$^+$) Calcd for [M+H]$^+$, 358.1627. Found, 358.1580 (+4.6 mmu).

[Chemical Formula 46]

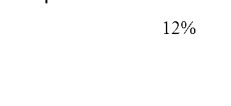

N-diMe Si-Rhodol $^1$H-NMR (400 MHz, $CDCl_3$): δ 0.52 (s, 3H), 0.53 (s, 3H), 2.05 (s, 3H), 3.23 (s, 6H), 6.54-6.60 (m, 2H), 7.01 (m, 4H), 7.13 (m, 1H), 7.33-7.52 (m, 3H): HRMS (ESL') Calcd for [M+H]$^+$, 372.1784. Found, 372.1768 (−1.5 mmu).

[Chemical Formula 47]

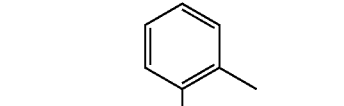

O-Me Si-Rhodol

HRMS (ESI$^+$) Calcd for [M]$^+$, 358.1627. Found, 358.1640 (+1.3 mmu).

The optical characteristics of the Si-Rhodol analogue synthesized above were as follows.

[Chemical Formula 48]

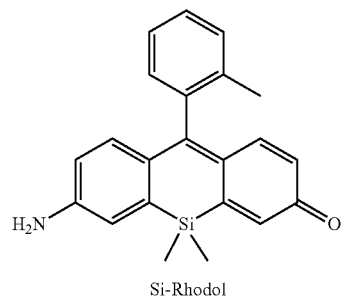

Si-Rhodol

λ$_{abs}$ = 507 nm (pH 3.0),
 584 nm (pH 7.4)
λ$_{em}$ = 605 nm
ε = 40,000
Φ$_{Fl}$ = 0.28 (pH 3.0)
 0.56 (pH 7.4)

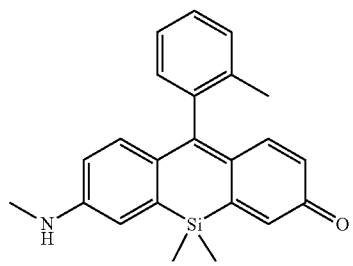

N-Me Si-Rhodol

λ$_{abs}$ = 513 nm (pH 3.0),
 598 nm (pH 7.4)
λ$_{em}$ = 619 nm
Φ$_{Fl}$ = 0.20 (pH 3.0)
 0.56 (pH 7.4)

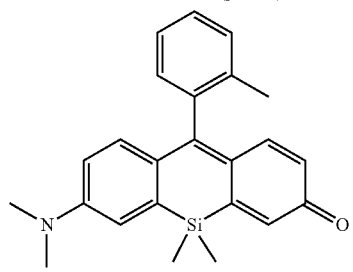

N-diMe Si-Rhodol

λ$_{abs}$ = 530 nm (pH 3.0),
 614 nm (pH 7.4)
λ$_{em}$ = 635 nm
Φ$_{Fl}$ = 0.05 (pH 3.0)
 0.16 (pH 7.4)

It is apparent from the above that Si-Rhodols can be endowed with longer absorbance and fluorescence wavelengths by alkylation of the amino group.

Figure 15:
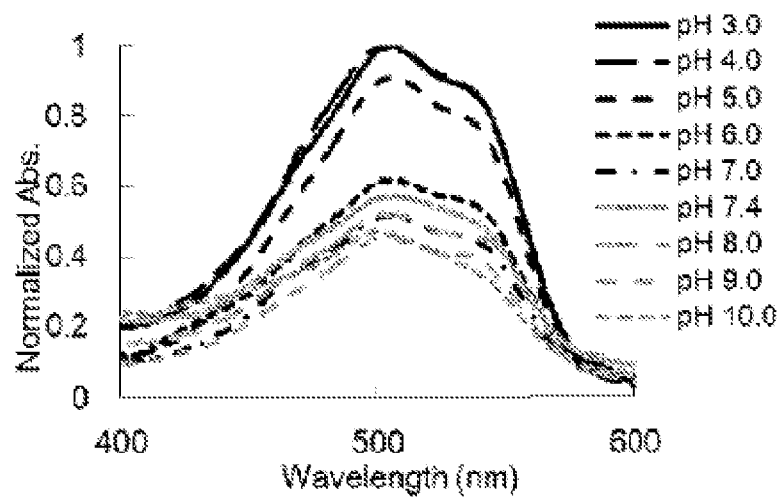
FIG. 15 pH profile of the absorbance spectrum of Compound 8.
Figure 16:
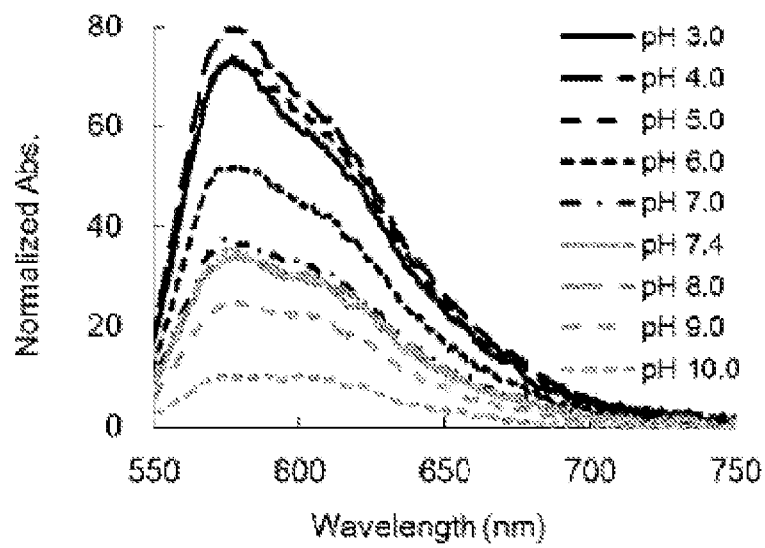
FIG. 16 pH profile of the fluorescence spectrum of Compound 8.

The pH profile of the absorbance and fluorescence spectra of O-Me-Si-Rhodol (Compound 8) was examined. The results thereof are shown in FIGS. 15 and 16. Measurement was carried out at various pH levels in 0.1M sodium phosphate solution containing 10% DMSO. The excitation wavelength was 503 nm.

The optical characteristics of Compound 8 are summarized below.

TABLE 7

| | Φ$_{FL}$$^c$ | λ$_{abs}$ (nm) | λ$_{em}$ (nm) |
|---|---|---|---|
| Compound 8 | 0.24 (pH: 3.0) 0.18 (pH: 7.4) | 503 | 580 |

Example 8

Compound 9 (N-AcSi-Rhodol) of the present invention was synthesized using the following scheme.

Scheme 9

[Chemical Formula 49]

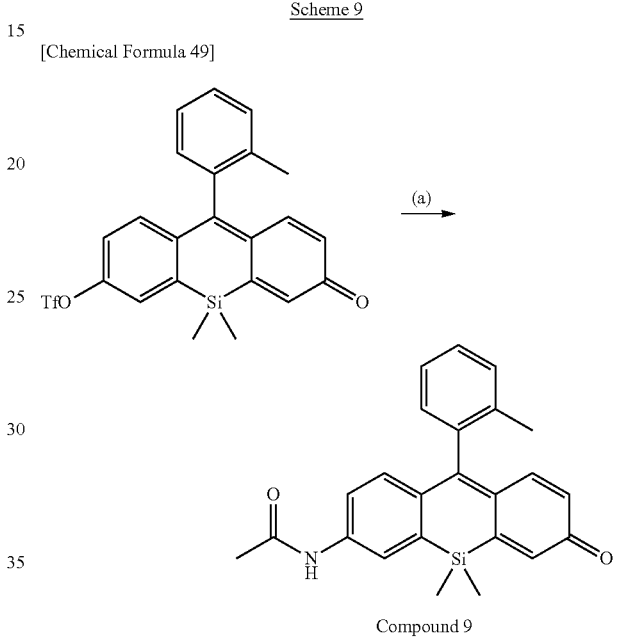

Compound 9

Pd$_2$(dba)$_3$CHCl$_3$, xantphos, Cs$_2$CO$_3$, and acetoamide/toluene, 100° C.

Step (a)

TM-OTf (18 mg, 38.6 μmol) was dissolved in toluene (10 mL), then Pd$_2$(dba)$_3$CHCl$_3$ (6 mg, 5.8 μmol), xantphos (8 mg, 13.8 μmol), Cs$_2$CO$_3$ (17.6 mg, 54 μmol), and acetoamide (5 mg, 84.7 μmol) were added thereto, and the system was stirred for 18 hours at 100° C. in an argon atmosphere. The reaction liquid was cooled to room temperature, after which dichloromethane was added, the system was filtered through celite, and the solvent was distilled away under reduced pressure. The residue was then refined by column chromatography (silica gel, 60% ethyl acetate/n-hexane) and further refined by HPLC to obtain N-AcSi-Rhodol (3.4 mg, 8.8 μmol, 23%).

$^1$H-NMR (300 MHz, CDCl$_3$): δ 0.49 (s, 3H), 0.50 (s, 3H), 2.05 (s, 3H), 2.21 (s, 3H), 6.28 (d, J=9.3 Hz, 1H), 6.86-6.89 (m, 2H), 6.99 (d, J=9.3 Hz, 1H), 7.09 (d, J=7.5 Hz, 1H), 7.32-7.34 (m, 2H), 7.37-7.45 (m, 3H): HRMS (ESI$^+$) Calcd for [M+H]$^+$, 415.1478. Found, 415.1453 (−2.5 mmu).

Figure 17:
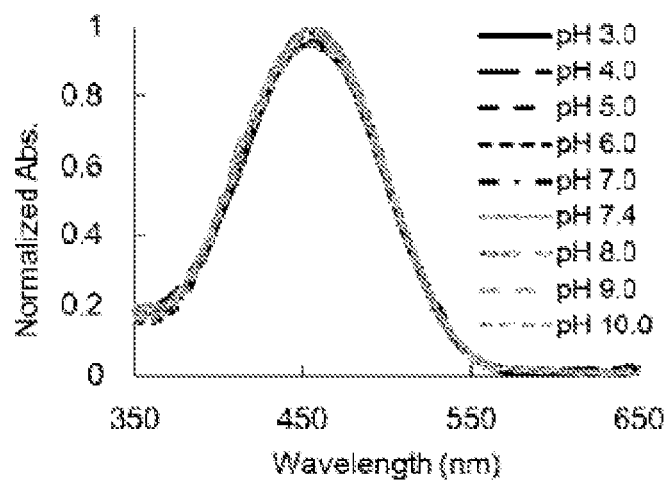
FIG. 17 pH profile of the absorbance spectrum of Compound 9.
Figure 18:
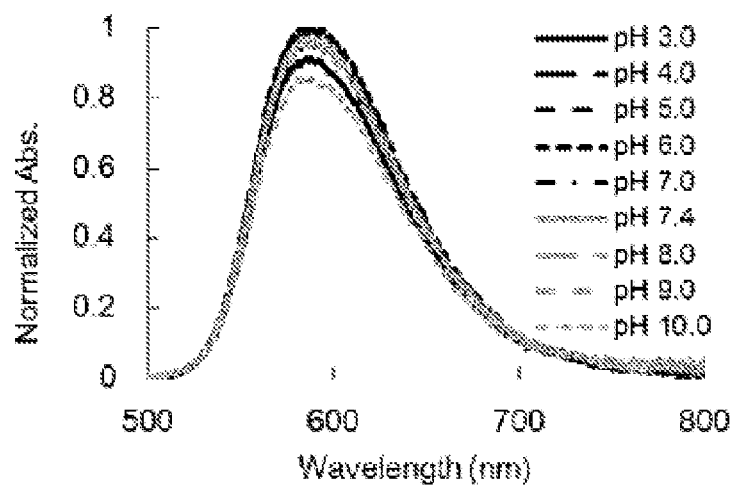
FIG. 18 pH profile of the fluorescence spectrum of Compound 9.

The pH profile of the absorbance and fluorescence spectra of N-AcSi-Rhodol (Compound 9) was examined. The results thereof are shown in FIGS. 17 and 18. Measurement was carried out at various pH in 0.1M sodium phosphate solution containing 10% DMSO. The excitation wavelength was 503 nm.

The optical characteristics of Compound 9 are summarized below.

TABLE 8

| | ε (M⁻¹cm⁻¹) | $\Phi_{FL}{}^c$ | $\lambda_{abs}$ (nm) | $\lambda_{em}$ (nm) |
|---|---|---|---|---|
| Compound 9 | 7000 (pH: 10.0) | 0.17 (pH: 7.4) | 455 | 590 |

Example 9

Compound 10 (2MeIndo-N-ethyl-phenol-SiR) of the present invention was synthesized using the following scheme.

Scheme 10

[Chemical Formula 50]

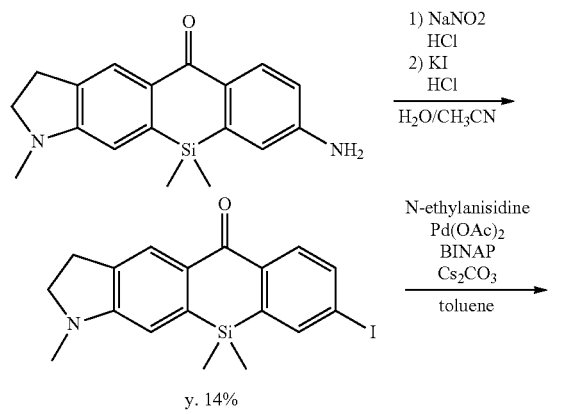

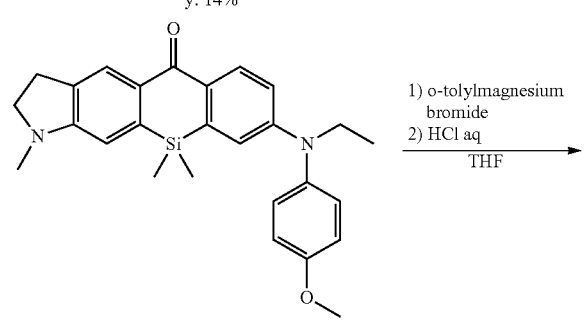

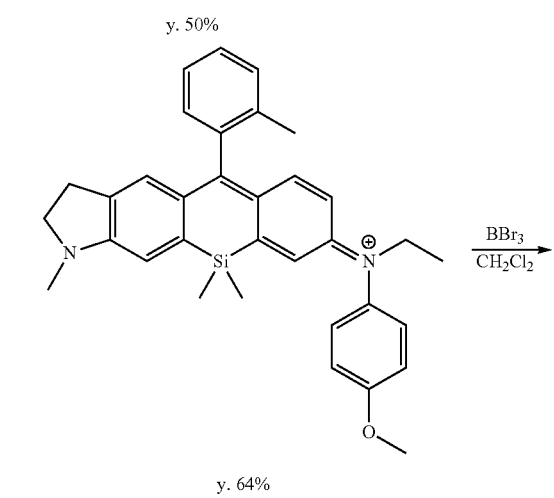

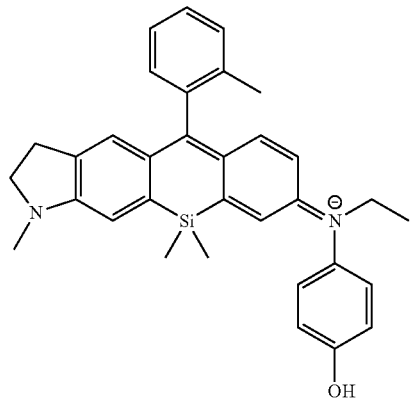

y. 75%
Compound 10

Synthesis of 8-iodo-1,10,10-trimethyl-2,3-dihydro-1H-benzo[5,6]silino[3,2-f]indole-5(10H)-one

[Chemical Formula 51]

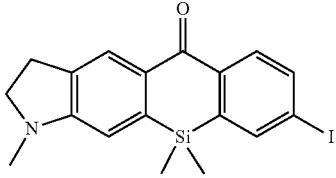

8-amino-1,10,10-trimethyl-2,3-dihydro-1H-benzo[5,6]silino[3,2-f]indole-5(10H)-one (308 mg, 1.0 mmol) was dissolved in an aqueous solution of 2N HCl (4 mL) and acetonitrile (4 mL), and the system was cooled to 0° C. above an ice bath. NaNO₂ (90 mg, 1.3 mmol) dissolved in water (1 mL) was dropped thereinto while being stirred. After 30 minutes of stirring, KI (800 mg, 5.0 mmol) dissolved in 2 mL of water was dropped while being vigorously stirred. After 1 hour of stirring, a saturated aqueous solution of sodium sulfite was added, the compound was extracted using CH₂Cl₂, solvent of the organic layer was removed, and the residue was refined by column chromatography (silica gel, CH₂Cl₂) to obtain 8-iodo-1,10,10-trimethyl-2,3-dihydro-1H-benzo[5,6]silino[3,2-f]indole-5(10H)-one (60 mg, yield: 14%).

¹H NMR (300 MHz, CDCl₂): δ 0.47 (s, 6H), 2.93 (s, 3H), 3.07 (t, J=8.70 Hz, 2H), 3.53 (t, J=8.10 Hz, 2H), 6.47 (s, 1H), 7.88 (dd, J=2.10, 8.70 Hz, 1H), 7.95 (d, J=2.40 Hz, 1H), 8.14 (d, J=8.70 Hz, 1H), 8.17 (s, 1H). ¹³C NMR (75 MHz, CDCl₂): d −1.41, 27.8, 34.1, 54.5, 100.2, 107.4, 107.5, 126.3, 130.2, 131.3, 132.5, 138.9, 140.2, 140.6, 141.4, 155.4, 185.3; HRMS (ESI⁺): Calcd for [M+H]⁺, 420.0281; found, 420.0329 (+4.8 mmu).

Synthesis of 8-(ethyl-p-methoxyphenyl)-1,10,10-trimethyl-2,3-dihydro-1H-benzo[5,6]silino[3,2-f]indole-5(10H)-one

[Chemical Formula 52]

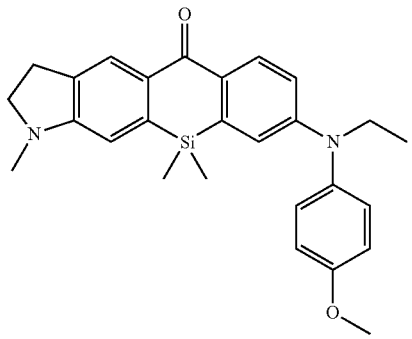

8-iodo-1,10,10-trimethyl-2,3-dihydro-1H-benzo[5,6]silino[3,2-f]indole-5(10H)-one (120 mg, 0.79 mmol) and N-ethyl-p-anisidine (21 mg, 0.05 mmol) were dissolved in toluene and added to a Schlenk flask, $Cs_2CO_3$ (260 mg, 0.80 mmol) was added, and deairing was carried out under Ar substitution. $Pd(OAc)_2$ (5.6 mg, 0.025 mmol) and BINAP (15.5 mg, 0.025 mmol) were added in an Ar atmosphere, and the system was heated and stirred for one night at 100° C. The system was filtered, the solvent was removed, and the residue was refined by column chromatography (silica gel, $CH_2Cl_2$) to obtain 8-(ethyl-p-methoxyphenyl)-1,10,10-trimethyl-2,3-dihydro-1H-benzo[5,6]silino[3,2-f]indole-5(10H)-one (11 mg, yield: 50%).

$^1$H NMR (300 MHz, $CDCl_3$): δ 0.43 (s, 6H), 1.31 (t, J=6.60 Hz, 3H), 2.95 (s, 3H), 3.10 (t, J=7.80 Hz, 2H), 3.52 (t, J=7.80 Hz, 2H), 3.84 (q, J=6.60 Hz, 2H), 3.91 (s, 3H), 6.53 (s, 1H), 6.79 (dd, J=3.00, 6.30 Hz, 1H), 6.83 (d, J=3.00 Hz, 1H), 7.01 (d, J=9.00H, 2H), 7.21 (d, J=9.00 Hz, 2H), 8.25 (s, 1H), 8.33 (d, J=8.70 Hz, 1H). HRMS (ESI$^+$): Calcd for [M+H]$^+$, 443.2155; found, 443.2109 (−4.6 mmu).

Synthesis of 2MeIndo-N-ethyl-anisoleSiR

[Chemical Formula 53]

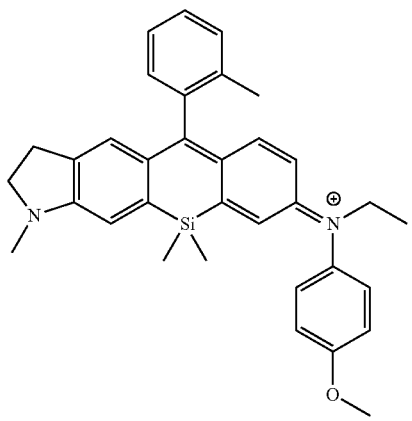

8-(ethyl-p-methoxyphenyl)-1,10,10-trimethyl-2,3-dihydro-1H-benzo[5,6]silino[3,2-f]indole-5(10H)-one (10 mg, 0.023 mmol) was dissolved in 5 mL of anhydrous THF, argon was substituted, and the system was heated and allowed to reflux at 80° C. 1 mL of a solution of 1M o-tolylmagnesium bromide in THF (1 mmol) was added and the system was heated and allowed to reflux for three hours at 80° C. The system was then restored to room temperature, 2N HCl was added, and the system was stirred for 15 minutes. The system was eluted using $CH_2Cl_2$, the solvent was removed, and the residue was refined by HPLC to obtain 2MeIndo-N-ethyl-anisoleSiR (8 mg, yield: 64%).

$^1$H NMR (300 MHz, $CDCl_3$): δ 0.49 (s, 3H), 0.51 (s, 3H), 1.30 (t, J=7.50 Hz, 3H), 2.06 (s, 3H), 2.98 (br, 2H), 3.37 (br, 2H), 3.82-3.96 (m, 8H), 6.42 (dd, J=2.10, 9.00 Hz, 1H), 6.75 (s, 1H), 6.86 (d, 9.00 Hz, 1H), 6.95-7.13 (m, 7H) 7.31-7.40 (m, 3H). HRMS (ESI$^+$): Calcd for [M]$^+$, 516.2675; found, 516.2630 (−4.6 mmu).

Synthesis of Compound 10: 2MeIndo-N-ethyl-phenol-SiR

[Chemical Formula 54]

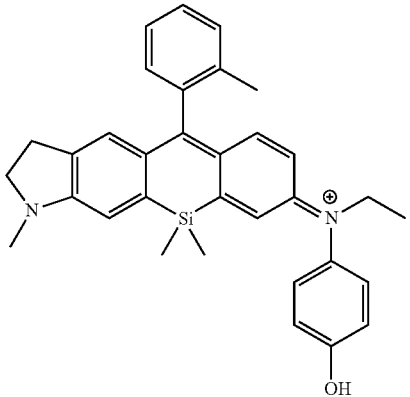

2MeIndo-N-ethyl-anisoleSiR (8 mg, 0.016 mmol) was dissolved in $CH_2Cl_2$, 16 μL of a 1M $BBr_3$ $CH_2Cl_2$ solution was added, and the system was stirred for 2 hours. Water was added, the organic layer was thereafter recovered by a separating operation, the solvent was removed, and the residue was refined by HPLC to obtain 2MeIndo-N-ethyl-phenol-SiR (6 mg, yield: 75%).

$^1$H NMR (300 MHz, $CDCl_3$): δ 0.45 (s, 3H), 0.47 (s, 3H), 1.27 (t, J=6.60 Hz, 3H), 2.05 (s, 3H), 2.99 (br, 2H), 3.29 (s, 3H), 3.82-3.91 (m, 4H), 6.52 (d, J=9.00 Hz, 1H), 6.76 (s, 1H), 6.91-6.96 (m, 5H), 7.04-7.09 (m, 3H), 7.33-7.44 (m, 3H); HRMS (ESI$^+$): Calcd for [M]$^+$, 503.2519; found, 503.2483 (−3.5 mmu).

Figure 19:
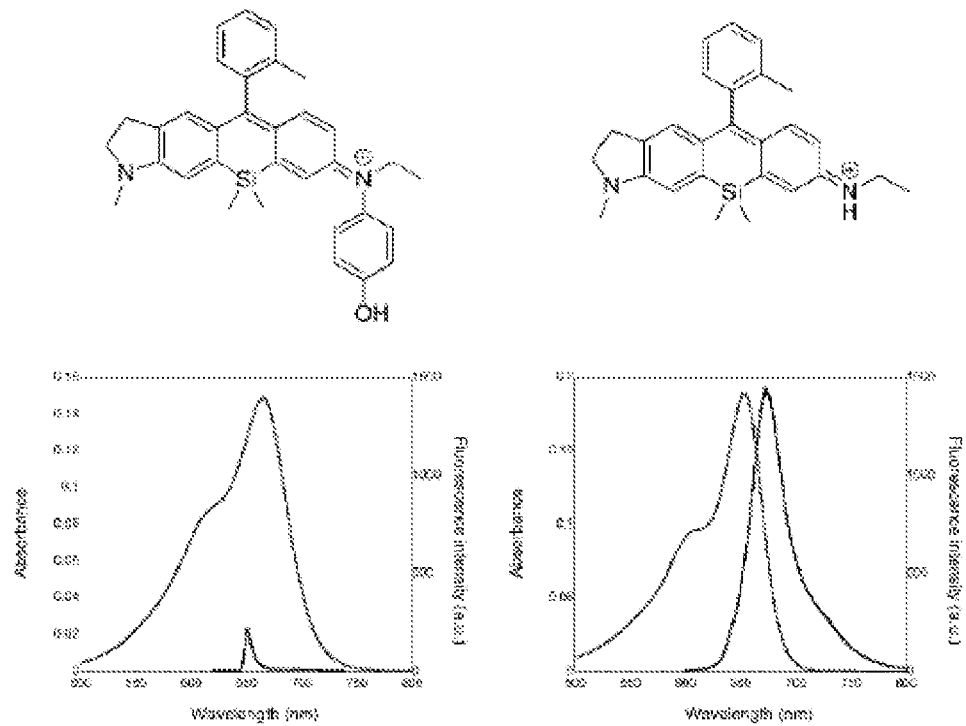
FIG. 19 Absorbance and fluorescence spectra of Compound 10 and compounds predicted to be generated after Compound 10 has reacted with active oxygen.

(1) Optical Characteristics of Compound 10 and Predicted Compounds Following the Reaction with Active Oxygen The absorbance and fluorescence spectra (left side of FIG. 19) of 1 μM of compound 10 in PBS (pH 7.4) containing 0.1% DMF as a cosolvent, the absorbance and fluorescence spectra (right side of FIG. 19) of the compound predicted to be generated following a reaction of compound 10 and 1 μM active oxygen, and the optical characteristics of each compound were measured (Table 9).

TABLE 9

|  | Abs$_{max}$ (nm) | Em$_{max}$ (nm) | $\Phi_{fl}$ |
| --- | --- | --- | --- |
| Compound 10 | 670 | n.d. | <0.001 |
| Predicted compound after reaction | 654 | 672 | 0.24 |

Compound 10 had a fluorescence quantum yield of not more than 0.001 and was without fluorescence. On the other hand, the fluorescence quantum yield of the reactant generated by the reaction with ROS was 0.24, which is sufficiently high in the near-infrared region. It is thereby anticipated that a fluorescence increase superior to that of existing active-oxygen probes will be exhibited.

Next, an analysis was carried out using the HPLC of a reaction induced by an active-oxygen-species.

Figure 20:
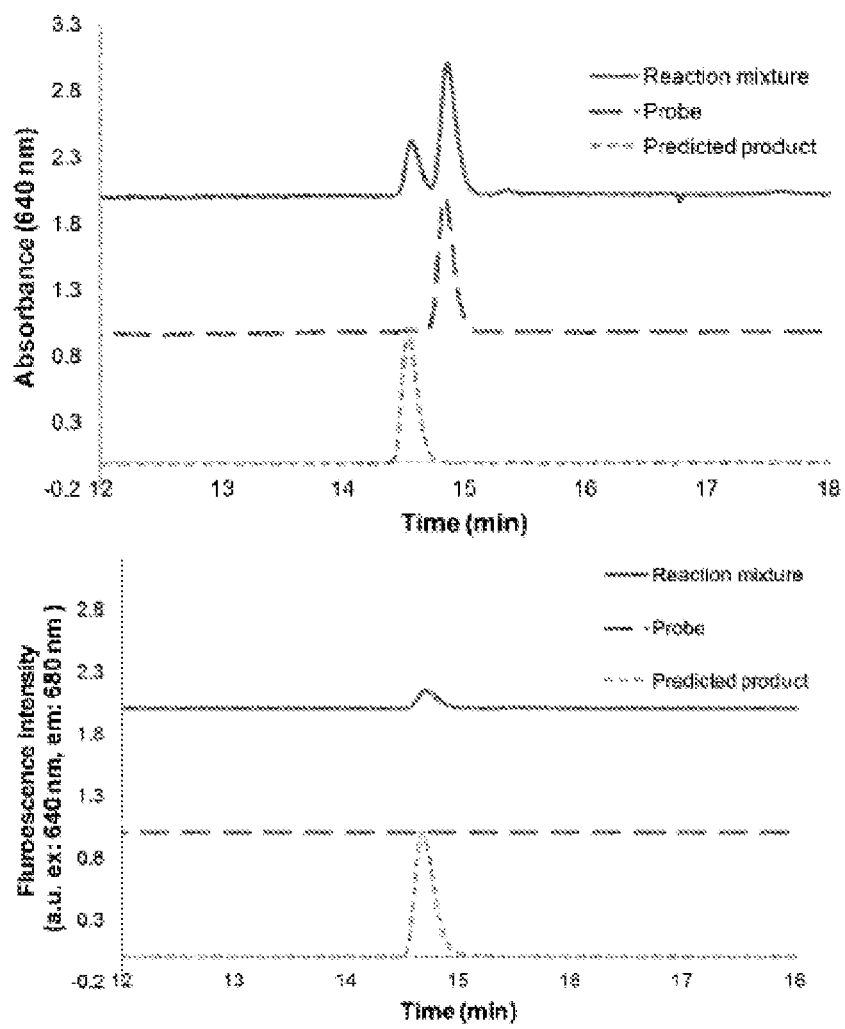
FIG. 20 HPLC chromatograph of the reaction mixture of ⁻OCl and Compound 10, Compound 10, and compounds predicted to follow a reaction of Compound 10 and ⁻OCl.

FIG. 20 shows a HPLC chromatograph of the reaction mixture (upper graph) composed of $^-$OCl and Compound 10, and the compound (lower graph) predicted after the reaction between Compound 10 and $^-$OCl. A sample was subjected to HPLC linear gradient elution (eluate: A/B=60/40—10 minutes—0/100; flow rate=1.0 mL/minute). The results are shown in FIG. 20.

Compound 10 reacted with $^-$OCl to produce the predicted reactant, and fluorescence had increased. When an analysis by HPLC was carried out, a compound having the same holding time as the predicted reactant was observed from the reaction liquid. Also, an ESI-MS measurement was carried out, and observation of the predicted mass spectrum of the reactant was also confirmed.

(2) Selectivity of Active-Oxygen Species

Next, the selectivity of active-oxygen species of compound 10 was examined. The conditions of various active-oxygen species were as follows.

$H_2O_2$: $H_2O_2$ was added to achieve final concentrations of 0, 1, 2, and 3 µM.
$^-$OCl: $^-$OCl was added to achieve final concentrations of 0, 1, 2.5, and 5 µM.
ONOO$^-$: ONOO$^-$ was added to achieve final concentrations of 0, 1, 2.5, and 5 µM.
$O_2^-$: A $KO_2$ solution was added to achieve final concentrations of 0, 1, 2.5, and 5 µM.
Hydroxy radical: $H_2O_2$ (final 1 mM) and $FeClO_4$ (final 100 µM) were added.

Figure 21:
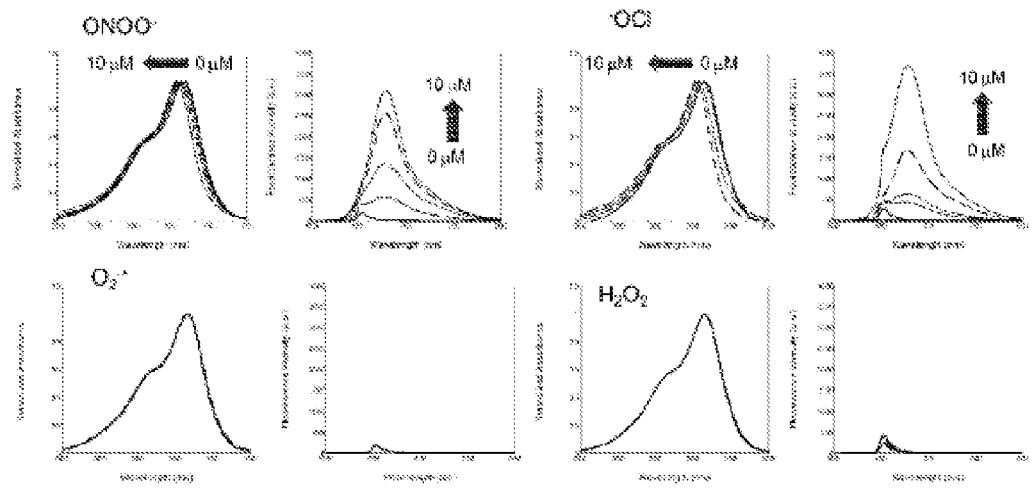
FIG. 21 Experiment results of the reactivity between Compound 10 and each active oxygen species.
Figure 22:
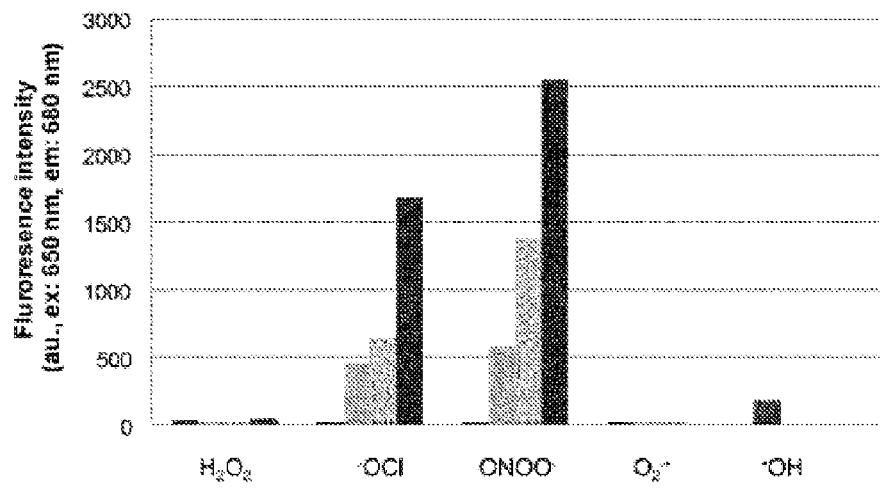
FIG. 22 Fluorescence intensity following a reaction between Compound 10 and each active oxygen species.

FIG. 21 shows the results of the examination of the reactivity between Compound 10 and each active-oxygen species. The left side in each drawing shows the absorbance spectrum and the right side shows the fluorescence spectrum. FIG. 22 shows the fluorescence intensity of each active-oxygen species.

Compound 10 reacted selectively with $^-$OCl and ONOO$^-$ and exhibited an increase in fluorescence. The increase in fluorescence was shown to be a value 100 times greater, and the increase in fluorescence was exhibited to be greater than existing near-infrared active-oxygen probes.

(3) Cell-Imaging Experiment Using HL60 Cells

A cell-imaging experiment using HL60 cells by Compound 10 was carried out using the following procedure.

Figure 23:
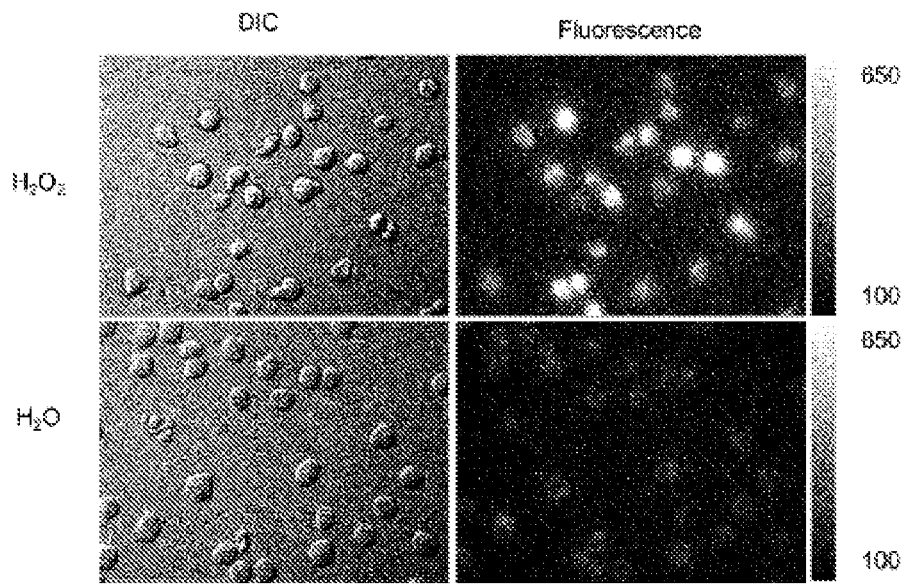
FIG. 23 Cell imaging using HL60 cells obtained using Compound 10.

HL60 cells were cultured. Compound 10 (containing 0.1% DMF as a cosolvent, the final concentration being 1 µM) was added to the cultured sample and culturing was allowed to proceed for 15 minutes. 1 mM of $H_2O_2$ was added to the sample, and culturing was allowed to proceed for 45 minutes. The fluorescence image was observed thereafter. The results are shown in FIG. 23. The left side of FIG. 23 shows the DIC and the right side shows the fluorescence image.

A probe was administered to the HL60 cells and stimulated by $H_2O_2$, and an increase in fluorescence was observed from inside the cells. Fluorescence had increased by about four times in 45 minutes after stimulation relative to when no stimulation was provided. This is thought to be caused by production of $^-$OCl by MPO, which is an enzyme in HL60 cells. This reacts with Compound 10 and an increase of fluorescence is observed. This suggests that the probe of the present invention is capable of detecting active oxygen even inside cells.

Example 10

Compound 11 (2MeazoSiR650) of the present invention was synthesized using the following scheme.

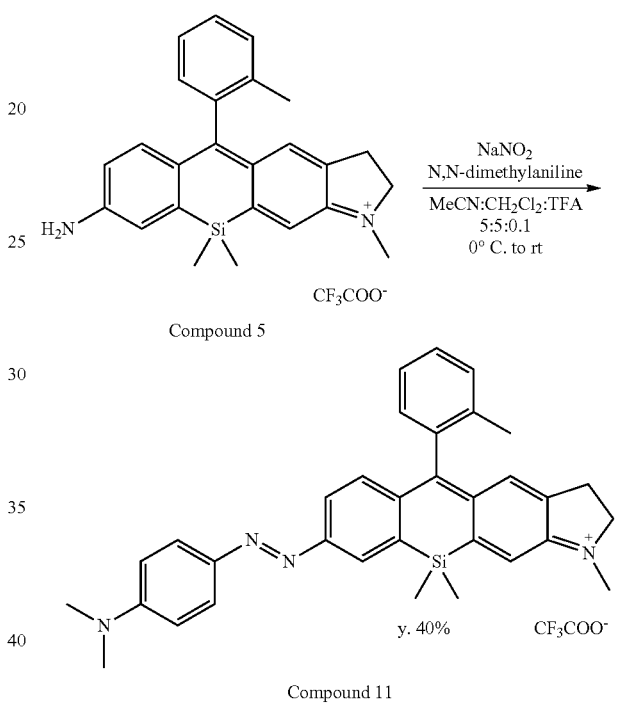

Synthesis of Compound 11 (2MeazoSiR650)

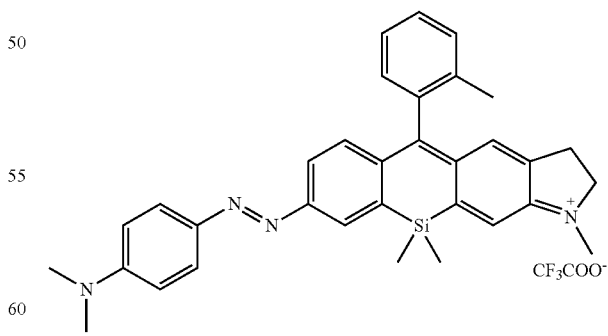

Compound 5 (12.3 mg, 24.8 µmol) obtained in Example 3 or 4 was dissolved in a mixed solvent (10 mL) composed of 1:1 MeCN/CH$_2$Cl$_2$ including 1% TFA, NaNo$_2$ (3.4 mg, 49.3 µmol) was added, and the system was stirred for 2 minutes in an argon atmosphere at 0° C. N,N-dimethylaniline (58 µL, 747 µmol) dissolved in MeCN (1 mL) was added thereafter. The system was stirred for an hour and a half while gradually being restored to room temperature, water was then added to the reaction liquid, and the resultant was extracted using CH₂Cl₂. The organic layer was dried using Na₂SO₄, and the solvent was removed to obtain 2MeazoSiR650 (8.3 mg, 10.0 µmol, 40%) by HPLC refining.

$^1$H NMR (300 MHz, CD₃OD): δ 0.64 (s, 3H), 0.69 (s, 3H), 2.07 (s, 3H), 3.04 (t, J=6.6 Hz, 2H), 3.15 (s, 6H), 3.57 (s, 3H), 4.14 (t, J=6.6 Hz, 2H), 6.86 (d, J=9.6, 2H), 6.92 (s, 1H), 7.13 (d, J=8.7, 1H), 7.19 (d, J=7.2, 1H), 7.40-7.51 (m, 3H), 7.66-7.70 (m, 2H), 7.88 (d, 9.6H), 8.22 (d, J=2.1, 1H). $^{13}$C NMR (75 MHz, CD₃OD): −1.8, −1.4, 19.6, 26.4, 35.4, 40.4, 58.1, 112.8, 122.1, 124.7, 127.1, 127.3, 129.7, 130.3, 130.3, 131.7, 134.0, 135.1, 137.1, 137.1, 139.3, 140.1, 141.5, 141.9, 145.5, 154.7, 155.2, 159.0, 161.4, 163.4. HRMS (ESI⁺): Calcd for [M]⁺, 515.2646. Found, 515.2631 (1.6 mmu).

Example 11

Compound 14 (diMeazoSiR650) was synthesized using the following scheme.

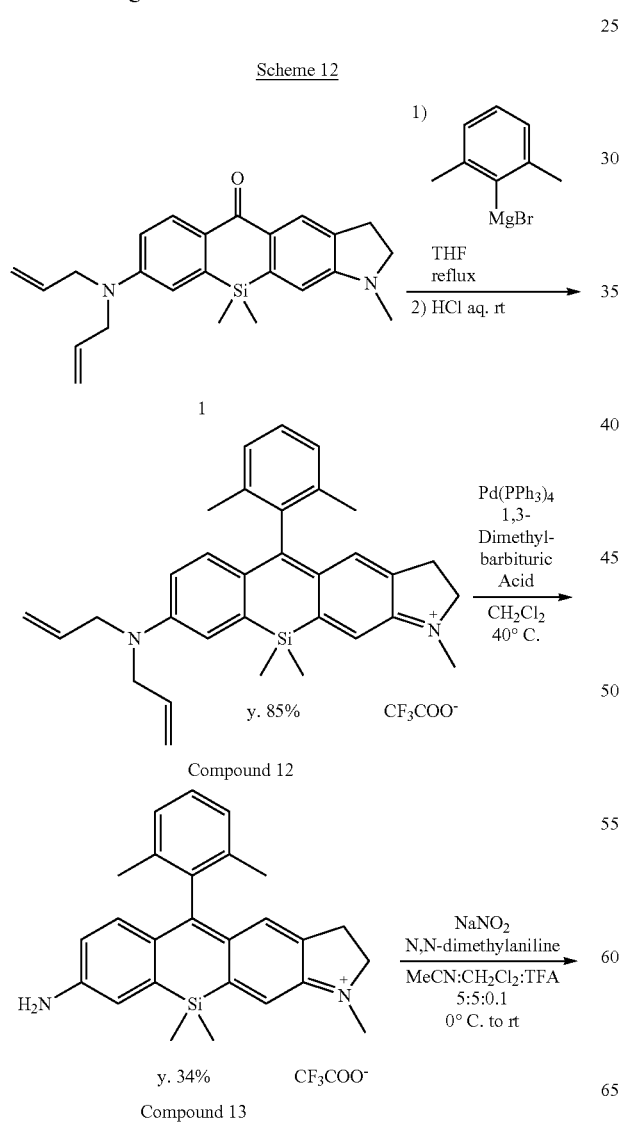

Scheme 12

Compound 12 y. 85% CF₃COO⁻

Compound 13 y. 34% CF₃COO⁻

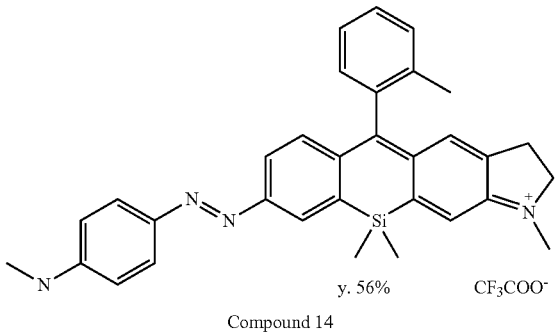

Compound 14 y. 56% CF₃COO⁻

Synthesis of Compound 12

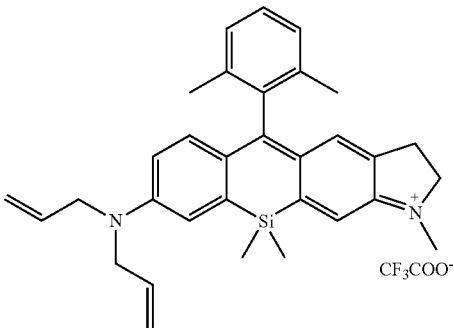

8-(diallylamino)-1,10,10-trimethyl-2,3-dihydro-1H-benzo[5,6]silino[3,2-f]indole-5(10H)-one (160 mg, 0.412 mmol) was dissolved in THF (20 mL), 2,6-dimethylphenyl magnesium bromide (1.0 M in THF) (4.1 mL, 4.1 mmol) was added, and the system was heated and allowed to reflux for 2 hours. 2,6-dimethylphenyl magnesium bromide (1.0 M in THF) (2.0 mL, 2.0 mmol) was additionally added, and the system was heated and allowed to reflux for 5 hours. An aqueous solution of 2N hydrochloric acid was thereafter added to the reaction liquid to quench the reaction, the mixture was extracted using dichloromethane, the organic layer was dried using Na₂SO₄, and the solvent was distilled away under reduced pressure. The residue was refined by HPLC to obtain Compound 12 (206.2 mg, 349.0 µmol, 85%).

$^1$H NMR (400 MHz, CD₃OD): δ 0.55 (s, 6H), 1.99 (s, 6H), 2.99 (t, J=7.2 Hz, 2H), 3.21 (s, 3H), 3.97 (t, J=7.2 Hz, 2H), 4.10 (d, J=4.8 Hz, 4H), 5.20 (d, J=17.2 Hz, 2H), 5.29 (d, J=10.4 Hz, 2H), 5.85 (m, 2H), 6.52 (dd, J=9.6, 2.8 Hz, 1H), 6.75 (s, 1H), 6.93 (d, J=9.6 Hz, 1H), 7.04 (d, J=2.8 Hz, 1H), 7.14 (s, 1H), 7.17 (d, J=7.6 Hz, 2H), 7.32 (t, J=7.6 Hz, 1H).

$^{13}$C NMR (75 MHz, CD₃OD): −1.5, 19.7, 25.9, 34.2, 53.2, 55.3, 113.8, 116.6, 117.8, 119.6, 127.4, 127.6, 128.5, 128.9, 131.1, 132.9, 134.5, 135.6, 138.3, 138.6, 145.3, 151.9, 154.4, 158.6, 167.2.

LRMS (ESI⁺): [M]⁺, 477.

Synthesis of Compound 13 (diMeSiR650)

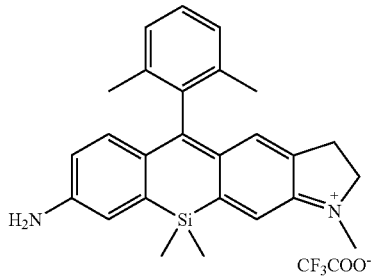

Compound 12 (83.6 mg, 0.142 mmol) was dissolved in 20 mL of dichloromethane, then 1,3-dimethylbarbituric acid (81.9 mg, 0.525 mmol) and tetrakis triphenylphosphine palladium (202.0 mg, 0.175 µmol) were added, and the system was stirred for 17 hours in an argon atmosphere at 40° C. Water was added to the mixture, the resultant was extracted using dichloromethane, the organic layer was dried using $Na_2SO_4$, the solvent was distilled away under reduced pressure, and the residue was thereafter refined by HPLC to obtain diMeSiR650 (24.2 mg, 47.4 µmol, 34%).

$^1$H NMR (300 MHz, $CDCl_3$): δ 0.53 (s, 6H), 1.98 (s, 6H), 2.97 (t, J=8.1 Hz, 2H), 3.24 (s, 3H), 3.85 (t, J=8.1 Hz, 2H), 6.53 (dd, J=9.0, 2.4 Hz, 1H), 6.75 (s, 1H), 6.89 (s, 1H), 6.92 (d, J=9.0 Hz, 1H), 7.16 (d, J=7.6 Hz, 2H), 7.22 (d, J=2.4 Hz, 1H), 7.32 (t, J=7.6 Hz, 1H).

$^{13}$C NMR (75 MHz, $CDCl_3$): −1.7, 19.6, 26.3, 33.7, 54.7, 114.3, 116.7, 123.8, 127.4, 127.6, 128.4, 128.5, 132.4, 133.2, 135.5, 138.7, 140.9, 147.7, 152.7, 155.6, 157.6, 168.8.

HRMS (ESI$^+$): Calcd for [M]$^+$, 397.2100. Found, 397.2055 (−4.5 mmu).

Synthesis of Compound 14 (diMeazoSiR650)

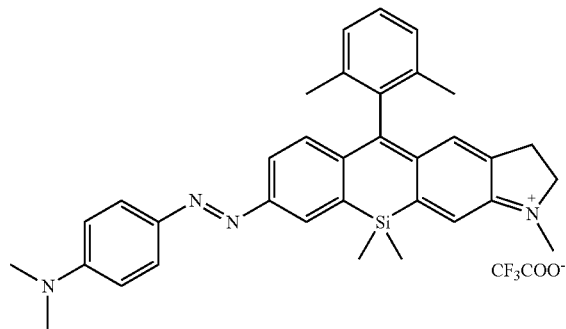

Compound 13 (13.0 mg, 25.4 µmol) was dissolved in a mixed solvent (10 mL) composed of 1:1 MeCN/$CH_2Cl_2$ including 1% TFA, $NaNo_2$ (3.6 mg, 52.2 µmol) was added, and the system was stirred for 2 minutes in an argon atmosphere at 0° C. N,N-dimethylaniline (58.8 µL, 756.8 µmol) dissolved in MeCN (1 mL) was added thereafter. The system was stirred for an hour and a half while gradually being restored to room temperature, water was then added to the reaction liquid, and the resultant was extracted using $CH_2Cl_2$. The organic layer was dried using $Na_2SO_4$, and the solvent was removed to obtain diMeazoSiR650 (8.9 mg, 14.2 µmol, 56%) by HPLC refining.

$^1$H NMR (300 MHz, $CD_3OD$): δ 0.67 (s, 6H), 2.02 (s, 6H), 3.06 (m, 2H), 3.15 (s, 6H), 3.58 (s, 3H), 4.15 (t, J=6.6 Hz, 2H), 6.87 (d, J=9.6 Hz, 2H), 6.91 (s, 1H), 7.15 (d, J=8.7 Hz, 1H), 7.28 (d, J=7.2 Hz, 2H), 7.40 (t, J=7.2 Hz, 1H), 7.68-7.72 (m, 2H), 7.89 (d, J=9.6 Hz, 2H), 8.25 (d, J=2.1 Hz, 1H). HRMS (ESI$^+$): Calcd for [M]$^+$, 529.2788. Found, 529.2743 (−4.4 mmu).

Example 12

(1) Optical Characteristics of Compounds 11, 13, and 14

Figure 24:
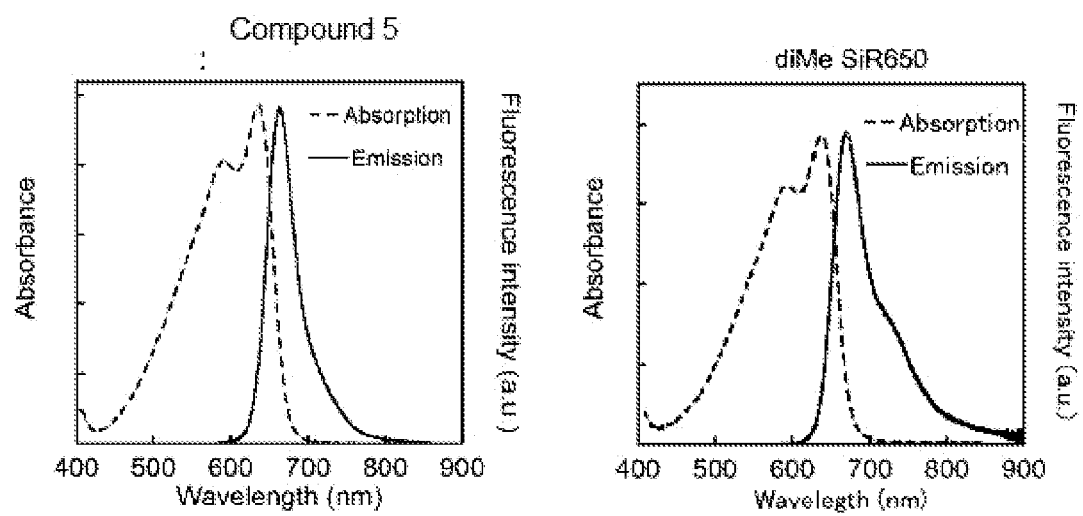
FIG. 24 Absorbance and fluorescence spectra of compounds 5 and 13.
Figure 25:
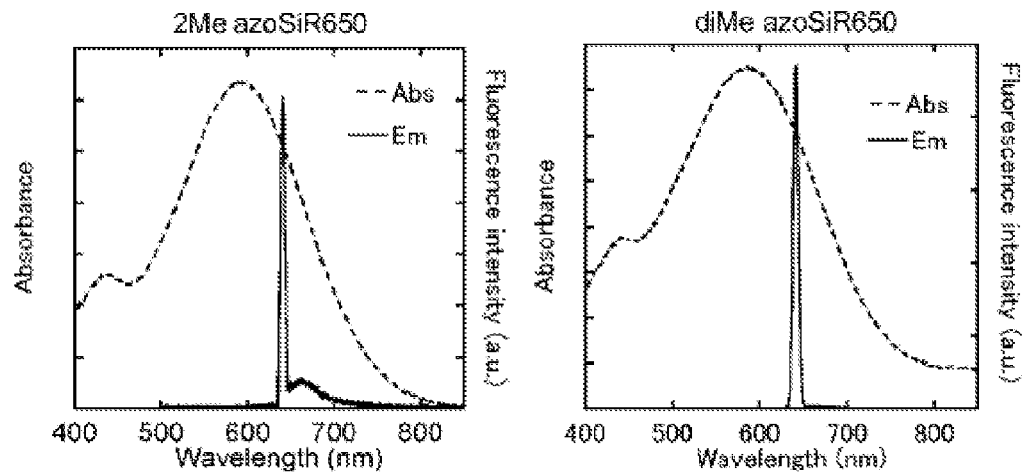
FIG. 25 Absorbance and fluorescence spectra of compounds 11 and 14.

FIG. 24 shows the absorbance and fluorescence spectra of compounds 5 and 13. FIG. 25 shows the absorbance and fluorescence spectra of compounds 11 and 14. The measurements were carried out in a phosphate buffered saline of pH 7.4.

Also, the optical characteristics of these compounds are summarized in the table below.

TABLE 9

Optical characteristics of dyes in a phosphate buffered saline of pH 7.4

| | $\lambda_{abs.\ max}$ (nm) | $\lambda_{fl.\ max}$ (nm) | $\Phi_n{}^b$ |
|---|---|---|---|
| Compound 5 | 637 | 664 | 0.14 |
| diMe SiR650 | 637 | 670 | 0.15 |
| 2Me azoSiR650 | 590 | N.D.$^a$ | <0.001 |
| diMe azoSiR650 | 587 | N.D. | 0.002 |

Figure 26:
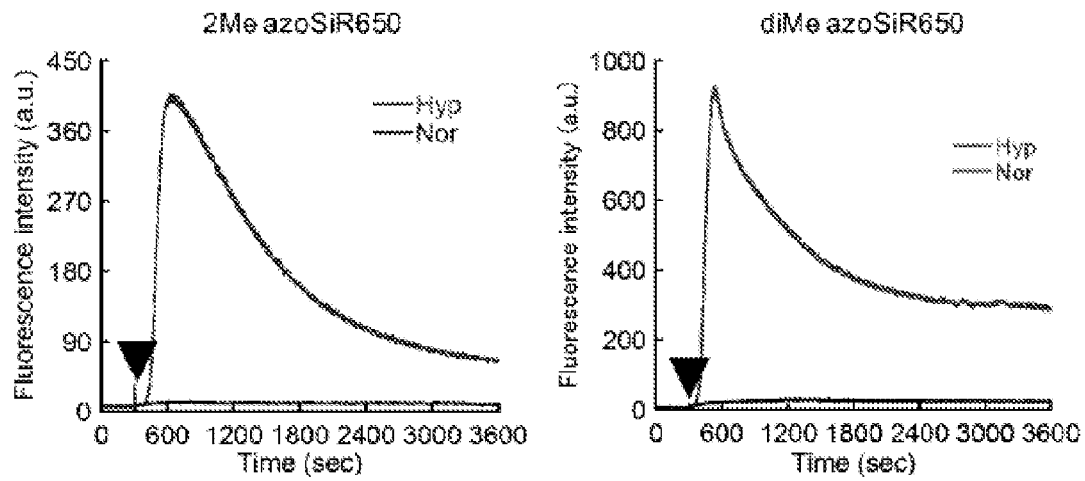
FIG. 26 Result of in vitro experiment using rat liver microsomes using compounds 11 and 14.

$^a$Not measurable.
$^b$Absolute fluorescence quantum yield measured using integrating spheres (2) In Vitro Experiment Using Rat Liver Microsomes 1 µM of Compound 11 or 14 and 226 µg of rat liver microsomes were added to 3 mL of a solution of potassium phosphoric acid. The change in fluorescence increase after 5 minutes was observed when 50 µM of NADPH as an electron donor was added (arrow head). The results are shown in FIG. 26.

The excitation wavelength was 640 nm and the fluorescence wavelength was 660 nm. In FIG. 26, Hyp is the measurement result for hypoxia and Nor is the measurement result for normal oxygen level. A dramatic increase in fluorescence intensity in a hypoxic environment was observed in for both compounds 11 and 14.

(3) Living Cell Experiment Using a Fluorescent Probe

Figure 27:
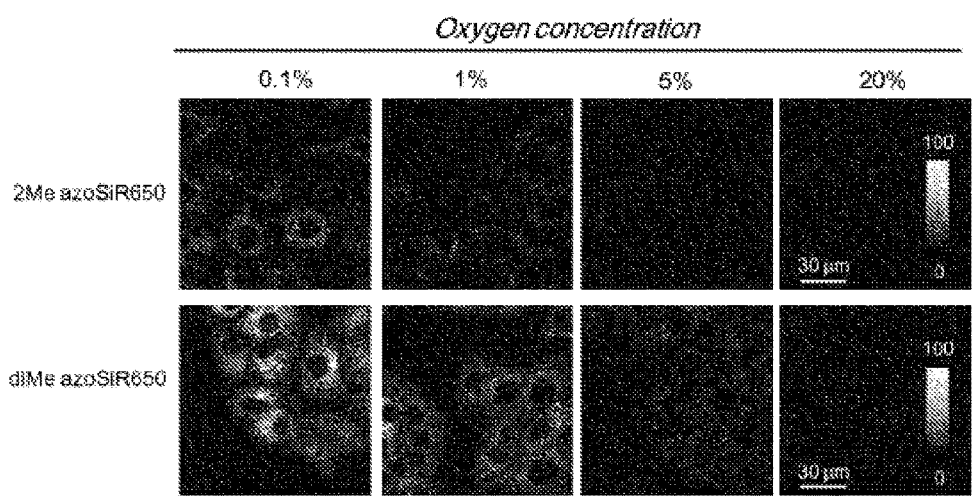
FIG. 27 Result of live cell experiment using compounds 11 and 14.

Compounds 11 and 14 were each added in 1 µM to A549 cells. The mixtures were cultivated for 6 hours under various oxygen concentration conditions and observed using a confocal fluorescence microscope. The results are shown in FIG. 27.

The excitation wavelength was 640 nm and the detection wavelength was 660 to 750 nm.

(4) Visibilitization Experiment of an Ischemic Organ in a Mouse

100 µM of Compound 14 was administered intravenously to a mouse, laparotomy was performed, and imaging was carried out until 32 minutes had elapsed. The portal vein, renal vein, and renal artery were thereafter tied off to produce liver and kidney ischaemia, and imaging was carried out until 18 minutes after ligature. A photograph was taken using Maestro (registered trademark) under the following conditions. Red filter used, exposure time: 300 ms, detection wavelength: 700 nm.

Figure 28:
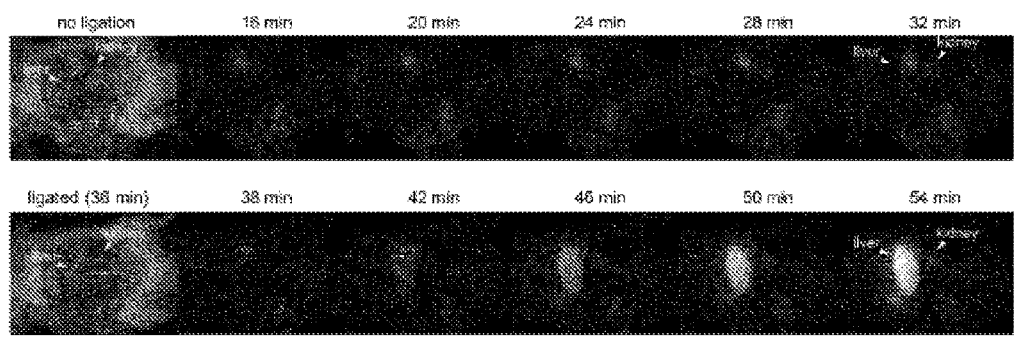
FIG. 28 Result of visibilitization of an ischemic organ in a mouse using Compound 14.

The results are shown in FIG. 28.

Application Example (1) Functionalizing the Hydroxyl Group of a Xanthene Ring

[Chemical Formula 55]

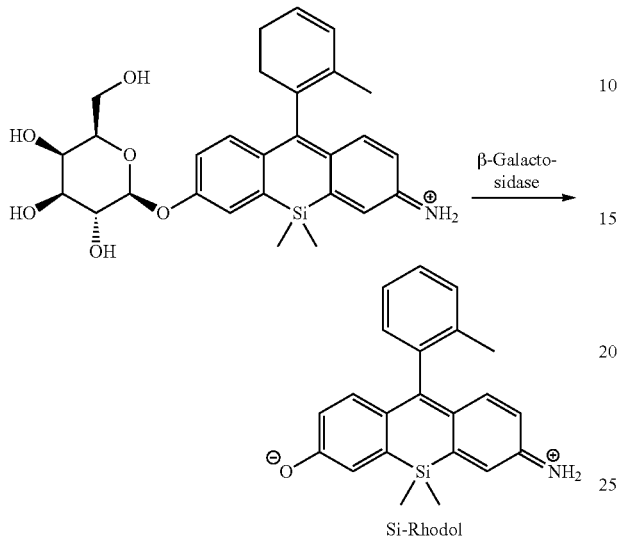

O-MeSi-Rhodol in which the phenolic hydroxyl group of Si-Rhodol has been methylized has an absorption maximum near 500 nm (FIG. 15), and Si-Rhodol has an absorption maximum near 580 nm (FIG. 12). Both compounds have an absorption maximum near 600 nm (FIGS. 14 and 16). Accordingly, β-Gal, being a substrate of β-galactosidase, is predicted to function as a β-galactosidase probe having two-wavelength excitation and single-wavelength fluorescent light by being bonded to the hydroxyl group of Si-Rhodol.

(2) Functionalizing the Amino Group of a Xanthene Ring

[Chemical Formula 56]

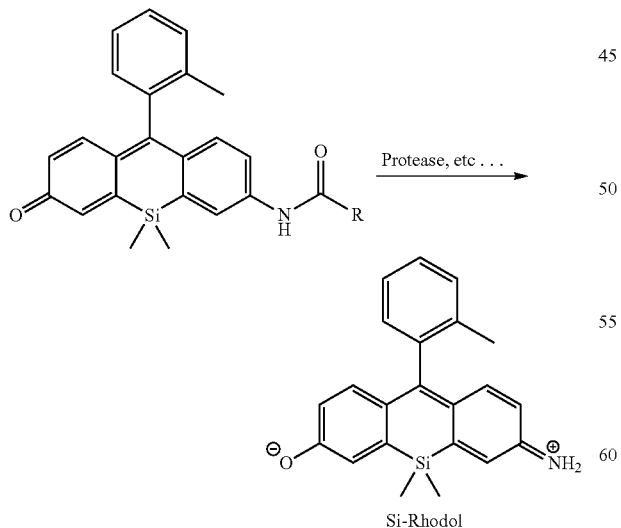

N-AcSi-Rhodol has (Compound 9) has an absorbance maximum near 450 nm, which is considerably distant from the absorbance maximum of 580 nm of Si-Rhodol, and it is therefore possible to selectively excite only Si-Rhodol by selection of the excitation wavelength. Accordingly, it is anticipated that N-AcSi-Rhodol will function as an Off/On-type protease probe, β-lactamase probe, and thiol probe by binding a specific peptide sequence that serves as a protease substrate, a β-lactam ring that serves as a β-lactamase matrix, a disulfide that reacts with in vivo thiol, and the like, to the amino group of Si-Rhodol.

The invention claimed is:

1. A compound of formula (I) below or a salt thereof

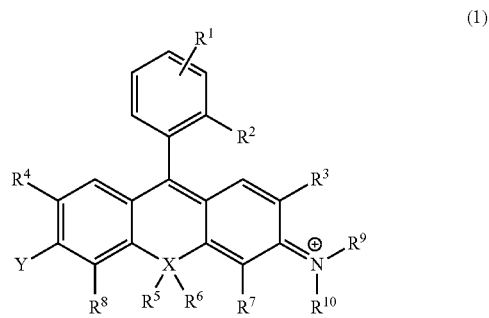

where:
$R^1$ is a hydrogen atom or 1-4 of the same or different monovalent substituents present on a benzene ring;
$R^2$ is a monovalent substituent;
$R^3$ and $R^4$ are, each independently, a hydrogen atom, $C_{1-6}$ alkyl group, or halogen atom;
$R^5$ and $R^6$ are, each independently, a $C_{1-6}$ alkyl group or aryl group;
$R^7$ and $R^8$ are, each independently, a hydrogen atom, $C_{1-6}$ alkyl group, or halogen atom;
$R^9$ and $R^{10}$ are, each independently, a hydrogen atom, $C_{1-6}$ alkyl group, or monovalent substituent cleaved by contact with a measured substance;
$R^9$ or $R^{10}$ optionally forms, together with $R^3$ or $R^7$, a 5-7-member heterocyclyl or heteroaryl containing a nitrogen atom to which $R^9$ or $R^{10}$ binds, and optionally contains 1-3 additional heteroatoms selected from the group consisting of oxygen atoms, nitrogen atoms, and sulfur atoms as ring-constituting members; the heterocyclyl or heteroaryl optionally being substituted by a $C_{1-6}$ alkyl, $C_{2-6}$ alkenyl, $C_{2-6}$ alkynyl, $C_{6-10}$ aralkyl, or $C_{6-10}$ alkyl-substituted alkenyl group;
Y is selected from
(1) $NR^{11}R^{12}$
(2) $OR^{13}$ or
(3) —N=N—$R^{14}$
where:
$R^{11}$ is a hydrogen atom, $C_{1-6}$ alkyl group, or monovalent substituent cleaved by contact with a measured substance;
$R^{12}$ is a hydrogen atom, $C_{1-6}$ alkyl group, or acyl group;
$R^{11}$ and $R^{12}$ optionally form a 5-7-member heterocyclyl containing a nitrogen atom to which $R^{11}$ and $R^{12}$ bind, and optionally contain 1-3 additional heteroatoms selected from the group consisting of oxygen atoms, nitrogen atoms, and sulfur atoms as ring-constituting members; the heterocyclyl optionally being substituted by a $C_{1-6}$ alkyl group;
$R^{13}$ is a hydrogen atom or monovalent substituent cleaved by contact with a measured substance; and
$R^{14}$ is an aryl group; and
X is a silicon, germanium, or tin atom;
when Y is —$NR^{11}R^{12}$, (i) $R^9$ and $R^{10}$ are not monovalent substituents cleaved by contact with a measured substance, and (ii) at least one of $R^9$ and $R^{10}$ differs from at least one of $R^{11}$ and $R^{12}$; provided that a compound wherein $R^9$ and $R^{10}$ are hydrogen, $R^{12}$ is a hydrogen, and $R^{11}$ is a monovalent substituent cleaved by contact with a measured substance, is excluded;

when Y is $-OR^{13}$ and $R^{13}$ is a hydrogen atom, $R^9$ or $R^{10}$ is optionally a monovalent substituent cleaved by contact with a measured substance; and when Y is $-N=N-R^{14}$, $R^9$ and $R^{10}$ are not a monovalent substituent cleaved by contact with a measured substance.

2. The compound or salt thereof according to claim 1 having the structure of formula (Ia) below, Y being $-NR^{11}R^{12}$

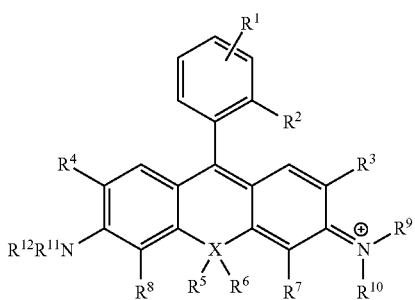

(Ia)

where:
$R^1$ to $R^{12}$ and X are as defined in formula (I), but (i) $R^9$ and $R^{10}$ are not monovalent substituents cleaved by contact with a measured substance, and (ii) when $R^{11}$ and $R^{12}$ are hydrogen atoms, $R^9$ and $R^{10}$ are not both hydrogen atoms.

3. The compound or salt thereof according to claim 2, wherein $R^9$ or $R^{10}$ forms, together with $R^3$ or $R^7$, a 5-7-member heterocyclyl or heteroaryl containing a nitrogen atom to which $R^9$ or $R^{10}$ binds; wherein the heterocyclyl or heteroaryl optionally contains 1-3 additional heteroatoms selected from the group consisting of oxygen atoms, nitrogen atoms, and sulfur atoms as ring-constituting members; the heterocyclyl or heteroaryl optionally being substituted by a $C_{1-6}$ alkyl, $C_{2-6}$ alkenyl, $C_{2-6}$ alkynyl, $C_{6-10}$ aralkyl group, or $C_{6-10}$ alkyl-substituted alkenyl group.

4. The compound or salt thereof according to claim 3, wherein $R^9$ forms, together with $R^3$, a 5-7-member heterocyclyl or heteroaryl containing a nitrogen atom to which $R^9$ binds.

5. The compound or salt thereof according to claim 4, having the structure of formula (Ia-1) below

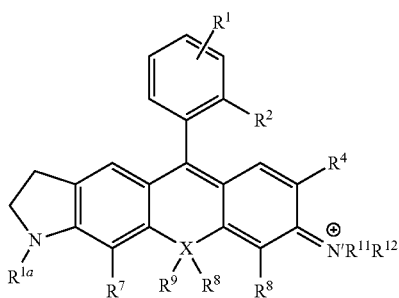

(Ia-1)

where $R^1$-$R^2$, $R^4$-$R^8$, $R^{10}$-$R^{12}$, and X are as defined in formula (Ia).

6. The compound or salt thereof according to claim 2, wherein $R^{11}$ and $R^{12}$ form a 5-7-member heterocyclyl containing a nitrogen atom to which $R^{11}$ and $R^{12}$ bind; wherein the heterocyclyl optionally contains 1-3 additional heteroatoms selected from the group consisting of oxygen atoms, nitrogen atoms, and sulfur atoms as ring-constituting members; the heterocyclyl optionally being substituted by a $C_{1-6}$ alkyl group.

7. A compound of formula (Ia) below or a salt thereof

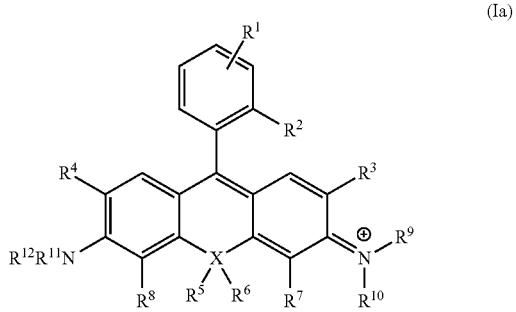

(Ia)

where:
$R^1$ is a hydrogen atom or 1-4 of the same or different monovalent substituents present on a benzene ring;
$R^2$ is a monovalent substituent;
$R^3$ and $R^4$ are, each independently, a hydrogen atom, $C_{1-6}$ alkyl group, or halogen atom;
$R^5$ and $R^6$ are, each independently, a $C_{1-6}$ alkyl group or aryl group;
$R^7$ and $R^8$ are, each independently, a hydrogen atom, $C_{1-6}$ alkyl group, or halogen atom;
$R^9$ and $R^{10}$ are, each independently, a hydrogen atom, $C_{1-6}$ alkyl group, or monovalent substituent cleaved by contact with a measured substance;
$R^9$ or $R^{10}$ optionally forms, together with $R^3$ or $R^7$, a 5-7-member heterocyclyl or heteroaryl containing a nitrogen atom to which $R^9$ or $R^{10}$ binds, and optionally contains 1-3 additional heteroatoms selected from the group consisting of oxygen atoms, nitrogen atoms, and sulfur atoms as ring-constituting members; the heterocyclyl or heteroaryl optionally being substituted by a $C_{1-6}$ alkyl, $C_{2-6}$ alkenyl, $C_{2-6}$ alkynyl, $C_{6-10}$ aralkyl, or $C_{6-10}$ alkyl-substituted alkenyl group;
X is a silicon, germanium, or tin atom;
$R^9$ and $R^{10}$ are not monovalent substituents cleaved by contact with a measured substance; and
$R^{11}$ and $R^{12}$ form a piperazine ring together with a nitrogen atom to which $R^{11}$ and $R^{12}$ bind.

8. The compound or salt thereof according to claim 7, having the structure of formula (Ia-2) below

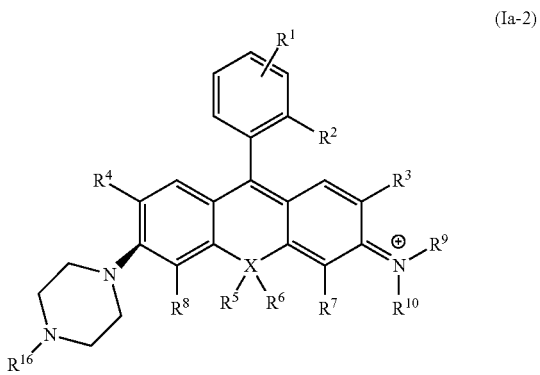

(Ia-2)

where $R^1$-$R^{10}$ and X are as defined in formula (Ia), and $R^{15}$ is a $C_{1-6}$ alkyl group.

9. A compound of formula (I) below or a salt thereof

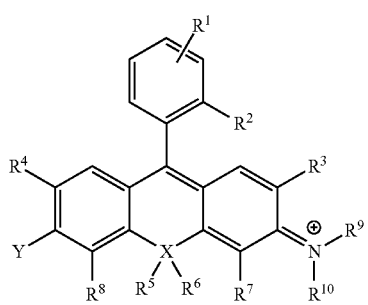

(I)

where:

R$^1$ is a hydrogen atom or 1-4 of the same or different monovalent substituents present on a benzene ring;

R$^2$ is a monovalent substituent;

R$^3$ and R$^4$ are, each independently, a hydrogen atom, C$_{1-6}$ alkyl group, or halogen atom;

R$^5$ and R$^6$ are, each independently, a C$_{1-6}$ alkyl group or aryl group;

R$^7$ and R$^8$ are, each independently, a hydrogen atom, C$_{1-6}$ alkyl group, or halogen atom;

R$^9$ and R$^{10}$ are, each independently, a hydrogen atom, C$_{1-6}$ alkyl group, or monovalent substituent cleaved by contact with a measured substance;

R$^9$ or R$^{10}$ optionally forms, together with R$^3$ or R$^7$, a 5-7-member heterocyclyl or heteroaryl containing a nitrogen atom to which R$^9$ or R$^{10}$ binds, and optionally contains 1-3 additional heteroatoms selected from the group consisting of oxygen atoms, nitrogen atoms, and sulfur atoms as ring-constituting members; the heterocyclyl or heteroaryl optionally being substituted by a C$_{1-6}$ alkyl, C$_{2-6}$ alkenyl, C$_{2-6}$ alkynyl, C$_{6-10}$ aralkyl, or C$_{6-10}$ alkyl-substituted alkenyl group;

Y is —NR$^{11}$R$^{12}$ where:

R$^{11}$ is a monovalent substituent cleaved by contact with an enzyme selected from the group consisting of peptidase, protease, lactamase, glycohydrolase, transferase, and oxidoreductase;

R$^{12}$ is a hydrogen atom, C$_{1-6}$ alkyl group, or acyl group;

X is a silicon, germanium, or tin atom; and

R$^9$ and R$^{10}$ are not monovalent substituents cleaved by contact with a measured substance.

10. The compound or salt thereof according to claim 9, wherein R$^{11}$ is a monovalent substituent cleaved by contact with an enzyme selected from the group consisting of peptidase, protease, and lactamase.

11. The compound or salt thereof according to claim 9, wherein the peptidase or protease is an enzyme selected from the group consisting of caspase, prostate-specific antigen, leucine aminopeptidase, and γ-glutamyl transpeptidase.

12. The compound or salt thereof according to claim 2, wherein R$^{11}$ is an aromatic ring and R$^3$ and R$^9$ together form a 5-7-member heterocyclyl or heteroaryl containing a nitrogen atom to which R$^9$ binds; and R$^{12}$ is a C$_{1-6}$ alkyl group.

13. A compound of formula (Ia-3) below or a salt thereof

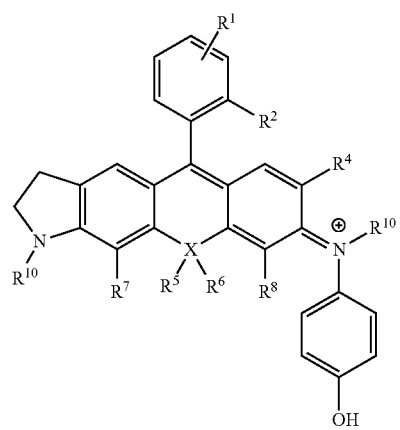

(Ia-3)

where:

R$^1$ is a hydrogen atom or 1-4 of the same or different monovalent substituents present on a benzene ring;

R$^2$ is a monovalent substituent;

R$^4$ is a hydrogen atom, C$_{1-6}$ alkyl group, or halogen atom;

R$^5$ and R$^6$ are, each independently, a C$_{1-6}$ alkyl group or aryl group;

R$^7$ and R$^8$ are, each independently, a hydrogen atom, C$_{1-6}$ alkyl group, or halogen atom;

R$^{10}$ is a hydrogen atom or C$_{1-6}$ alkyl group;

R$^{12}$ is a hydrogen atom, C$_{1-6}$ alkyl group, or acyl group; and

X is a silicon, germanium, or tin atom.

14. The compound or salt thereof according to claim 13, having the structure of formula (1) below

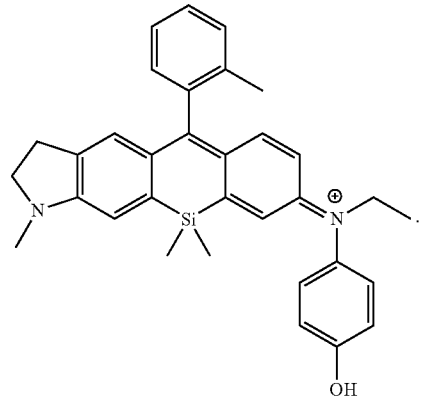

(I)

15. A compound of formula (Ib) below or a salt thereof

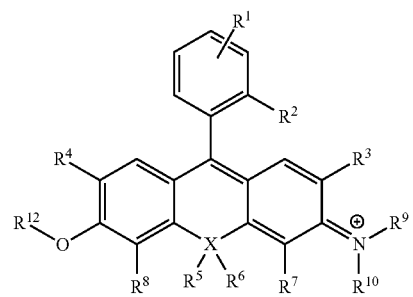

(Ib)

where:

R$^1$ is a hydrogen atom or 1-4 of the same or different monovalent substituents present on a benzene ring;

$R^2$ is a monovalent substituent;
$R^3$ and $R^4$ are, each independently, a hydrogen atom, $C_{1-6}$ alkyl group, or halogen atom;
$R^5$ and $R^6$ are, each independently, a $C_{1-6}$ alkyl group or aryl group;
$R^7$ and $R^8$ are, each independently, a hydrogen atom, $C_{1-6}$ alkyl group, or halogen atom;
$R^9$ and $R^{10}$ are, each independently, a hydrogen atom, $C_{1-6}$ alkyl group, or monovalent substituent cleaved by contact with a measured substance;
$R^9$ or $R^{10}$ optionally forms, together with $R^3$ or $R^7$, a 5-7-member heterocyclyl or heteroaryl containing a nitrogen atom to which $R^9$ or $R^{10}$ binds, and optionally contains 1-3 additional heteroatoms selected from the group consisting of oxygen atoms, nitrogen atoms, and sulfur atoms as ring-constituting members; the heterocyclyl or heteroaryl optionally being substituted by a $C_{1-6}$ alkyl, $C_{2-6}$ alkenyl, $C_{2-6}$ alkynyl, $C_{6-10}$ aralkyl, or $C_{6-10}$ alkyl-substituted alkenyl group;
$R^{13}$ is a hydrogen atom or monovalent substituent cleaved by contact with a measured substance; and
X is a silicon, germanium, or tin atom; and
when $R^{13}$ is a hydrogen atom, $R^9$ or $R^{10}$ are optionally a monovalent substituent cleaved by contact with a measured substance.

16. The compound or salt thereof according to claim 15, wherein $R^{13}$, $R^9$, or $R^{10}$ is a monovalent substituent cleaved by contact with an enzyme selected from the group consisting of peptidase, protease, lactamase, glycohydrolase, transferase, and oxidoreductase.

17. The compound or salt thereof according to claim 16, wherein $R^{13}$, $R^9$, or $R^{10}$ is a monovalent substituent cleaved by contact with an enzyme selected from the group consisting of peptidase, protease, and lactamase.

18. The compound or salt thereof according to claim 17, wherein the monovalent substituent is cleaved by a peptidase or protease selected from the group consisting of caspase, prostate-specific antigen, leucine aminopeptidase, and γ-glutamyl transpeptidase.

19. A compound of formula (Ic) below or a salt thereof

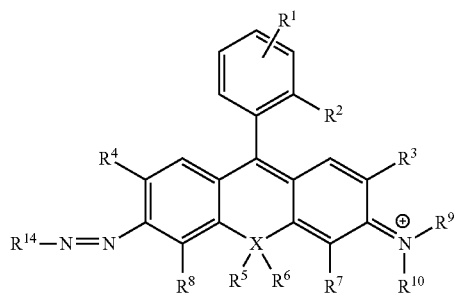

(Ic)

where:
$R^1$ is a hydrogen atom or 1-4 of the same or different monovalent substituents present on a benzene ring;
$R^2$ is a monovalent substituent;
$R^3$ and $R^4$ are, each independently, a hydrogen atom, $C_{1-6}$ alkyl group, or halogen atom;
$R^5$ and $R^6$ are, each independently, a $C_{1-6}$ alkyl group or aryl group;
$R^7$ and $R^8$ are, each independently, a hydrogen atom, $C_{1-6}$ alkyl group, or halogen atom;
$R^9$ and $R^{10}$ are, each independently, a hydrogen atom, $C_{1-6}$ alkyl group, or monovalent substituent cleaved by contact with a measured substance;
$R^9$ or $R^{10}$ optionally forms, together with $R^3$ or $R^7$, a 5-7-member heterocyclyl or heteroaryl containing a nitrogen atom to which $R^9$ or $R^{10}$ binds, and optionally contains 1-3 additional heteroatoms selected from the group consisting of oxygen atoms, nitrogen atoms, and sulfur atoms as ring-constituting members; the heterocyclyl or heteroaryl optionally being substituted by a $C_{1-6}$ alkyl, $C_{2-6}$ alkenyl, $C_{2-6}$ alkynyl, $C_{6-10}$ aralkyl, or $C_{6-10}$ alkyl-substituted alkenyl group;
$R^{14}$ is an aryl group;
X is a silicon, germanium, or tin atom; and
$R^9$ and $R^{10}$ are not a monovalent substituent cleaved by contact with a measured substance.

20. The compound or salt thereof according to claim 19, wherein the aryl group of $R^{14}$ is a monocyclic aromatic group or a condensed aromatic group, and the aryl group has a substituent selected from an amino group and a dimethyl amino group.

21. A fluorescent probe containing the compound defined in claim 1.

22. An active-oxygen-detecting fluorescent probe containing the compound of claim 12.

23. A low-oxygen-environment-detecting fluorescent probe containing the compound of claim 19.

24. A method for manufacturing the compound of formula (Ia) of claim 2 wherein $R^1$-$R^{12}$ and X are as defined above, or salt thereof, wherein the method comprises:
(a) reacting a 3-halo-N,N-diallyl aniline of formula (II), where $R^{16}$ represents a halogen atom, manufactured from a 3-halogenated aniline and an allyl halide, and a 3-halobenzene amine compound of formula (III), in the presence of formamide, to produce a compound of formula (IV) below;

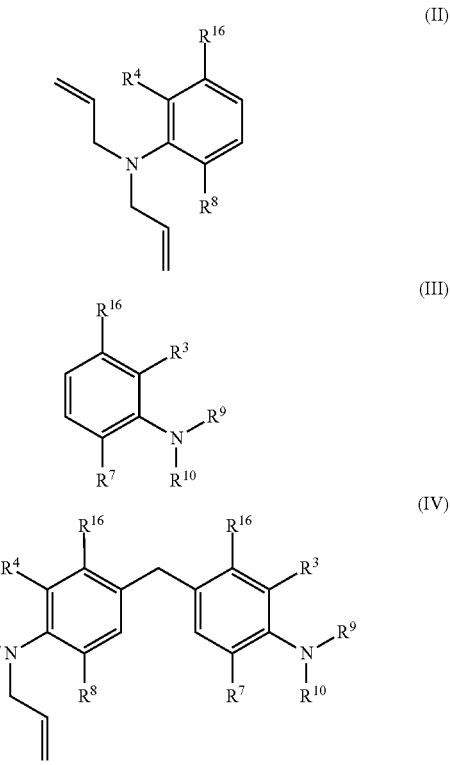

(b) reacting the compound of formula (IV) and X(Halo)₂ (R⁵)(R⁶), where Halo is a chlorine atom or a bromine atom; and X, R⁵, R⁶ are as defined above, and subsequently producing a compound of formula (V) below by oxidation;

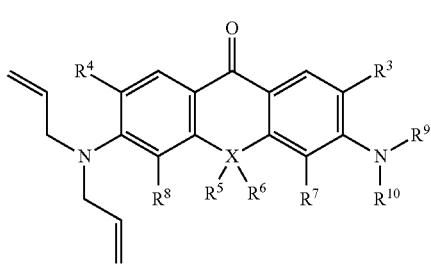

(V)

(c) manufacturing a compound of formula (VI) below from a halobenzene derivative and the compound of formula (V); and

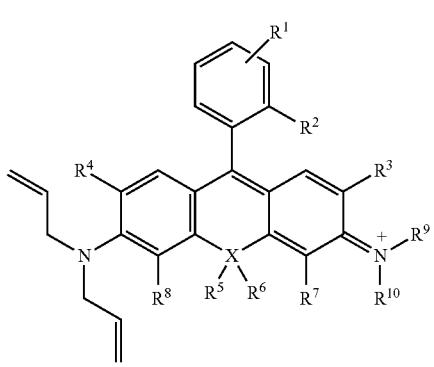

(VI)

(d) de-allylating the compound of formula (VI), and manufacturing a compound in which R¹¹ and R¹² in formula (Ia) are hydrogen atoms, wherein when a protecting group is introduced into R¹ and R² to manufacture the compound of formula (VI), the protecting group may be deprotected before, after, or simultaneously with step (d).

25. The method according to claim 24, further comprising introducing, as R¹¹, a monovalent substituent cleaved by contact with a measured substance.

26. A method for manufacturing the compound of formula (Ia) of claim 2, wherein R¹-R¹² and X are as defined above, or salt thereof, wherein the method comprises:
(1) reacting a 3-halo-N,N-diallyl aniline of formula (VII), where R¹⁶ represents a halogen atom, manufactured from a 3-haloaniline and an allyl halide in the presence of phosphorus oxychloride under basic conditions to manufacture a 3-halo-N,N-diallyl-4-hydroxymethylaniline of formula (VIII);

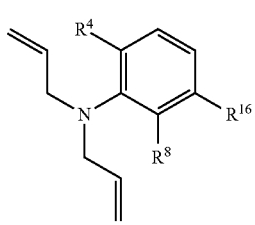

(VII)

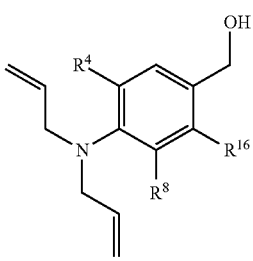

(VIII)

(2) reacting the 3-halo-N,N-diallyl-4-hydroxymethyl aniline and a 3-halobenzene amine compound of formula (IX) to manufacture a compound of formula (X);

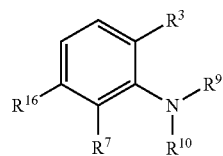

(IX)

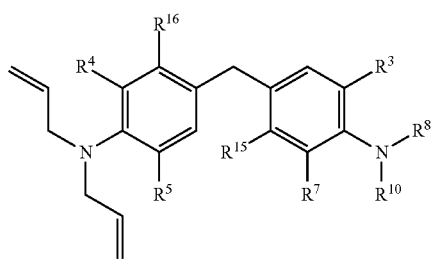

(X)

(3) reacting the compound of formula (X) and X(Halo)₂ (R⁵)(R⁶), wherein Halo is a chlorine atom or a bromine atom; and X, R⁵, and R⁶ are as defined above, and subsequently manufacturing, by oxidation, N,N-diallylamino-N',N'-dialkylamino-X-xanthone of formula (V) below;

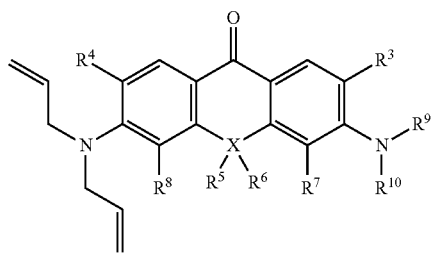

(V)

(4) manufacturing a compound of formula (VI) below from the N,N-diallylamino-N',N'-dialkylamino-X-xanthone and a halobenzene derivative; and

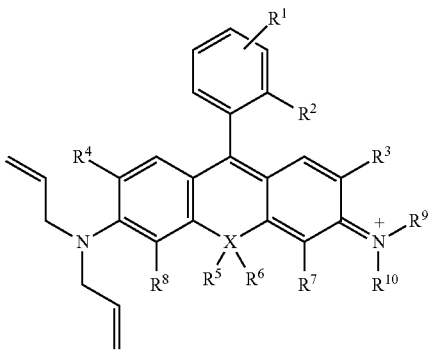

(VI)

(5) de-allylating the compound of formula (VI), and manufacturing a compound in which $R^{11}$ and $R^{12}$ in formula (Ia) are hydrogen atoms, wherein when a protecting group is introduced into $R^1$ and $R^2$ to manufacture the compound of formula (VI), the protecting group may be deprotected before, after, or simultaneously with step (4).

27. The method according to claim 26, further comprising introducing, as $R^{11}$, a monovalent substituent cleaved by contact with a measured substance.

28. A method for manufacturing the compound or salt thereof of formula (Ib) of claim 15, wherein the method comprises:
    (1) reacting a compound of formula (XI) below, under basic conditions, with trifluoromethanesulfonic anhydride ($Tf_2O$) to manufacture a compound of general formula (XII) below;

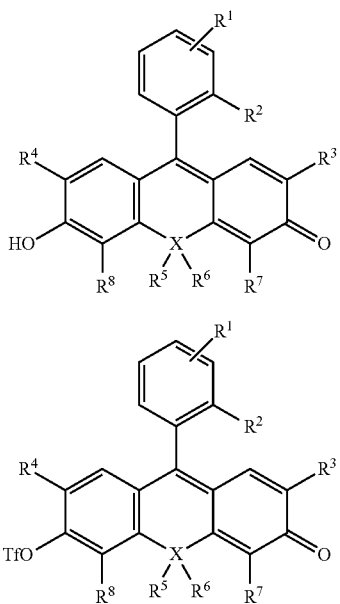

(2) reacting the compound of formula (XII) with an imine compound, and thereby manufacturing a compound of formula (XIII); and

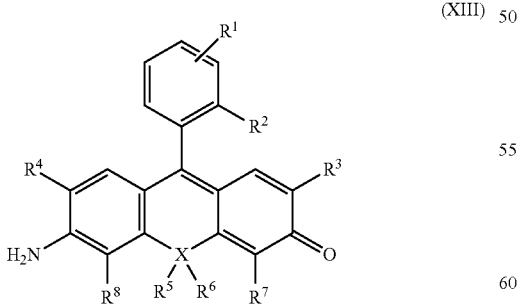

(3) optionally reacting the compound of formula (XIII) with an alkyl halide.

29. A method for manufacturing the compound or salt thereof of formula (Ia-3) of claim 13, wherein the method comprises:

(1) reacting a compound of formula (XIV) with potassium iodide, and thereby manufacturing a compound of formula (XV);

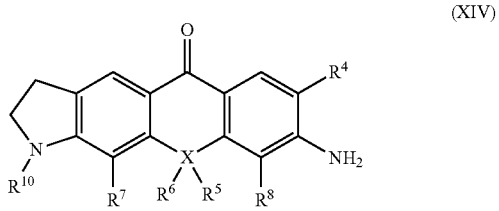

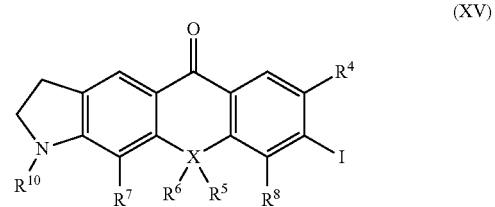

(2) reacting the compound of formula (XV) with N-alkyl-p-anisidine, in which the alkyl group has 1-6 carbons, and thereby manufacturing a compound of formula (XVI);

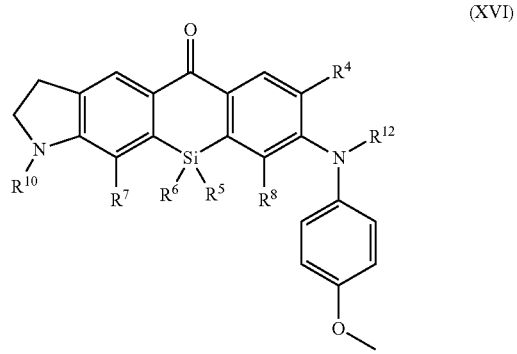

(3) reacting the compound of (XVI) with o-tolylmagnesium bromide, and subsequently adding an acid to manufacture a compound of formula (XVII); and

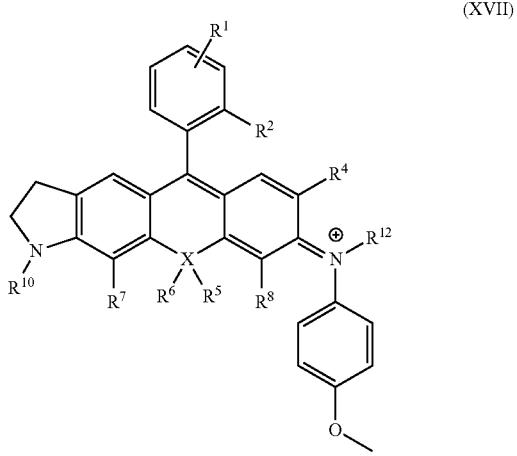

(4) reacting the compound of formula (XVII) with boron tribromide, and thereby manufacturing a compound of formula (Ia-3).

* * * * *

UNITED STATES PATENT AND TRADEMARK OFFICE
CERTIFICATE OF CORRECTION

PATENT NO.        : 9,714,260 B2                                  Page 1 of 1
APPLICATION NO.   : 14/759306
DATED             : July 25, 2017
INVENTOR(S)       : T. Nagano et al.

It is certified that error appears in the above-identified patent and that said Letters Patent is hereby corrected as shown below:

In the Claims

At Column 66, Line 48, (Claim 1, Line 25), please change "(1) $NR^{11}R^{12}$" to
--(1) —$NR^{11}R^{12}$--.

At Column 66, Line 49, (Claim 1, Line 26), please change "(2) $OR^{13}$ or" to
--(2) —$OR^{13}$ or--.

At Column 69, Line 65, (Claim 12, Line 27), please change "aromatic ring and" to
--aromatic ring; and--.

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*